(12) United States Patent
Defaye et al.

(10) Patent No.: US 7,781,417 B2
(45) Date of Patent: Aug. 24, 2010

(54) CYCLODEXTRIN DIMERS AND DERIVATIVES THEREOF, METHODS FOR PREPARING THEM AND THEIR USE, IN PARTICULAR, FOR THE SOLUBILIZING PHARMACOLOGICALLY ACTIVE SUBSTANCES

(75) Inventors: Jacques Defaye, Saint Ismier (FR); Carmen Ortiz-Mellet, Sevilla (ES); José Manuel Garcia-Fernandez, Sevilla (ES); Juan M. Benito, Bollulos M. (ES); Marta Gomez-Garcia, Sevilla (ES); Jian-Xin Yu, Dallas, TX (US)

(73) Assignees: Centre National de la Recherche Scientifique, Paris (FR); Universite Joseph Fourier, Saint Martin d'Heres (FR); Consejo Superior de Investigaciones Cientificas (CSIC), Madrid (ES); Universidad de Sevilla, Sevilla (ES)

( * ) Notice: Subject to any disclaimer, the term of this patent is extended or adjusted under 35 U.S.C. 154(b) by 0 days.

(21) Appl. No.: 10/580,856

(22) PCT Filed: Nov. 24, 2004

(86) PCT No.: PCT/FR2004/002998

§ 371 (c)(1),
(2), (4) Date: Nov. 21, 2006

(87) PCT Pub. No.: WO2005/054303

PCT Pub. Date: Jun. 16, 2005

(65) Prior Publication Data

US 2007/0082867 A1    Apr. 12, 2007

(30) Foreign Application Priority Data

Nov. 26, 2003 (FR) .................................. 03 13873

(51) Int. Cl.
*A61K 31/724* (2006.01)
*C08B 37/16* (2006.01)
(52) U.S. Cl. ......................................... 514/58; 536/103
(58) Field of Classification Search .................... 514/58
See application file for complete search history.

(56) References Cited

U.S. PATENT DOCUMENTS 5,684,169 A * 11/1997 Hamada et al. ............. 549/510
6,642,214 B1 * 11/2003 Moser ......................... 514/58

FOREIGN PATENT DOCUMENTS

| EP | 0 639 380 A | 2/1995 |
| WO | WO 90/02141 A | 3/1990 |
| WO | WO 95/21870 A | 8/1995 |
| WO | WO 97/33919 A | 9/1997 |
| WO | WO 01/51524 A | 7/2001 |
| WO | WO 03/052060 A | 6/2003 |

OTHER PUBLICATIONS

Benito et al. Journal of the American Chemical Society, 2004, 126, p. 10355-10363.*
Ortiz-Mellet et al. Chem. Eur. J. 2002, 8(9), p. 1982-1990.*
Kotter et al. J. Chem. Soc., Perkin Trans. 1, 1998, p. 2193-2200.*
Charbonnier et al. Tetrahedron Letters, 1999, 40, p. 6581-6583.*
Baussanne et al., "Synthesis and Comparative Lectin-Binding Affinity of Mannosyl-Coated Beta-cyclodextrin-dendrimer constructs,"Chem. Commun., 2000, pp. 1489-1490, xp 008032689.

* cited by examiner

*Primary Examiner*—Shaojia Anna Jiang
*Assistant Examiner*—Jonathan S Lau
(74) *Attorney, Agent, or Firm*—Young & Thompson

(57) ABSTRACT

The invention relates to a compound according to the following general formula (I), in which: m represents an integer equal to 5, 6 or 7; n and $n^1$ represent an integer from 1 to 5; the A groups represent, in particular, a hydrogenated atom; X represents O or S; Y represents, in particular, a group $NR_1$, $R_1$, representing, in particular, a hydrogenated atom; W represents CH or N; and Z represents, in particular, a hydrogenated atom.

6 Claims, No Drawings

CYCLODEXTRIN DIMERS AND DERIVATIVES THEREOF, METHODS FOR PREPARING THEM AND THEIR USE, IN PARTICULAR, FOR THE SOLUBILIZING PHARMACOLOGICALLY ACTIVE SUBSTANCES

The present invention relates to novel cyclodextrin dimer derivatives, as well as their preparation methods. The present invention also relates to the use of these novel derivatives for the solubilization of pharmacologically active substances in an aqueous medium.

The cyclodextrins, or cyclomaltooligosaccharides, are cyclic oligosaccharides which are known for their ability to include in their cavity various molecules, of a size suited to that of the host structure. The generally apolar character of these associations leads preferentially to the inclusion of hydrophobic-type molecular structures, allowing in particular the solubilization in water and biological media of compounds which are only slightly or not at all soluble in these media and optionally to improve their stabilization. These properties are currently used in particular for the transport of medicaments.

The relatively low solubility in water of the cyclodextrins, and in particular of the more economically accessible of them, β-cyclodextrin (18 g/l, or 15 mmol/l, at 25° C.) however limits their use for this purpose. On the other hand, as cyclodextrins possess no recognition ability vis-à-vis biological receptors in the organism, these entities cannot be used for the targeting and vectoring of active ingredients.

In order to remedy this situation, cyclodextrins have been chemically modified in order to improve their solubility in water on the one hand and, on the other hand, in order to incorporate cell recognition signals in their structure. Thus, the international applications WO 95/19994, WO 95/21870 and WO 97/33919 and the European patent application EP 0 403 366 describe cyclodextrin derivatives, one or more primary alcohol functions of which are substituted by monosaccharide or oligosaccharide groups via an oxygen or sulphur atom or via a thiourea group, as well as their use. These branched cyclodextrins are in particular capable of serving as a host for taxol and its derivatives, in particular Taxotere®, which are antineoplastic and antiparasitic agents, as described by P. Potier in *Chem. Soc. Rev.*, 21, 1992, pp. 113-119. Thus inclusion complexes are obtained, which makes it possible to solubilize these antineoplastic agents in water. By way of example, the solubility in water of Taxotere® which is 0.004 g/L, can be increased to 6.5 g/L by adding 6$^I$-S-α-maltosyl-6$^I$-thiocyclomaltoheptaose to its aqueous suspension, as described in the document WO 95/19994.

The document EP-A-0 605 753 describes inclusion complexes of taxol using branched cyclodextrins such as the maltosyl-cyclodextrins, in order to increase the solubility of this diterpene in water.

Cyclodextrin derivatives comprising one or more glycosyl or maltosyl substituents linked to the cyclodextrin by a sulphur atom are also described by V. Laine et al. in *J. Chem. Soc., Perkin Trans.*, 2, 1995, pp. 1479-1487. These derivatives have been used in order to solubilize an anti-inflammatory agent such as prednisolone.

The document WO 97/33919 describes methods for preparing thioureido-cyclodextrins by coupling of the 6$^I$-amino-6$^I$-deoxycyclodextrins or also of the corresponding peramine derivatives with alkyl isothiocyanates or mono- or oligosaccharides.

The incorporation of glucide substituents on the cyclodextrins leads to derivatives provided with a solubility in water which is much higher if compared with the starting cyclodextrin. At the same time, this approach makes it possible to confer upon the cyclodextrin a particular affinity for certain biological sites, as the glucide substituents are well known as cell recognition markers. Thus, this type of modification of the cyclodextrin can allow the targeting and vectoring of an active ingredient included in the cavity of the cyclodextrin.

The affinity of a glucide marker for a specific cell membrane receptor (lectin) is low as a general rule. In order to achieve affinities which are useful for targeting and vectoring, a multiple and simultaneous presentation of the ligand must be envisaged. In the case of cyclodextrin derivatives monosubstituted in primary alcohol position (i.e. cyclodextrins in which only one of the OH groups of the corona of the primary alcohols is substituted), this problem can be partially resolved by the incorporation of glycodendritic structures, as described by I. Baussanne et al. in *Chem. Commun*, 2000, pp. 1489-1490 and by J. M. Benito et al. in *Chem. Eur. J.*, 2003, in the press. However, the method for preparing such compounds is complicated.

Moreover, the recent results described by I. Baussanne et al. in *ChemBioChem* 2001, pp. 777-783 show that the β-cyclodextrin derivatives comprising glycosylthioureido-type substituents, obtained from the corresponding per-(C-6)-amine, do not exhibit sufficient affinity vis-à-vis the complementary lectins. Nevertheless, the solubilization ability of these derivatives vis-à-vis antineoplastic agents of the paclitaxel family, such as docetaxel (Taxotere®) remains lower than that observed in the case of the cyclodextrin derivatives monosubstituted in primary alcohol position.

In all the examples of mono- or polysubstituted cyclodextrin derivatives commented on, it is observed that the molar proportion of cyclodextrin:antineoplastic agent solubilized in water is significantly less than 1:1. In fact, the presence of two aromatic cycles in the derivatives of Taxol and Taxotere®, capable of inclusion in the hydrophobic cavity of cyclodextrin, makes it possible to assume a character ditopic for these molecules and, consequently, a tendency towards the formation of sandwich-type complexes with the cyclodextrin derivatives.

At present, no cyclodextrin derivative exists which is obtained by a simple method, making it possible to increase the solubilization of pharmacologically active ditopic substances and also having a sufficient affinity vis-à-vis the complementary biological receptors.

One of the purposes of the present invention is to provide novel cyclodextrin dimer derivatives comprising two sub-units of cyclodextrin linked in primary alcohol position, not only being useful for the solubilization of the active ingredients, in particular of the antineoplastic agents of the taxol family such as Taxotere®, but also having a strong affinity vis-à-vis specific membrane receptors, which makes it possible to envisage, by means of these, efficient and selective transport of the active ditopic substance towards target organs.

Another objective of the invention is to provide a preparation method which is simple to implement, and making it possible to obtain novel cyclodextrin dimer derivatives with a good yield, of the order of at least 50%, and preferably 70%, without having to carry out long and complicated purification methods.

The present invention relates to a compound corresponding to the following general formula:

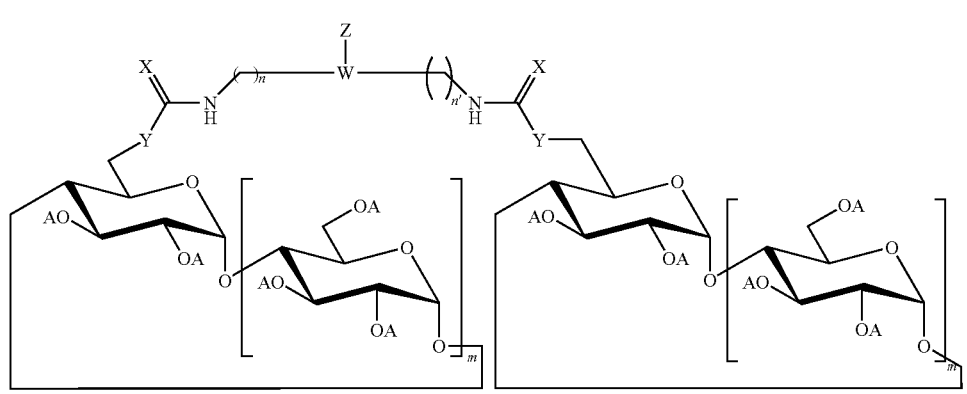
(I)

in which:

m represents an integer equal to 5, 6 or 7;

n and n' represent an integer from 1 to 5, n and n' being able to be identical or different;

the A groups, identical or different, represent a hydrogen atom, an acyl, alkyl, hydroxyalkyl or sulphoalkyl group of 1 to 16 carbon atoms, X represents O or S, Y represents a substituent with an amine function which forms part of a urea function (case where X=O) or of a thiourea function (case where X=S), such as:

an $—NR_1—$ group, $R_1$ representing a hydrogen atom or an alkyl group comprising from 1 to 6 carbon atoms, or an amide group of formula $—NH—CO—(CH_2)_q—NR_1—$, q representing an integer from 1 to 5 and $R_1$ being as defined above, or a cysteaminyl group of formula $—S—(CH_2)_r—NR_1—$, r representing an integer from 2 to 5 and $R_1$ being as defined above, W represents CH or N;

Z represents:

a hydrogen atom or a carbamate substituent of formula

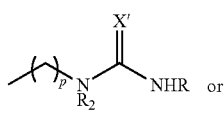

an amine substituent of formula

a quaternary ammonium group of formula

a urea or thiourea substituent of formula

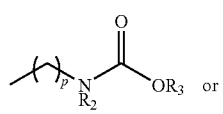

a group of formula

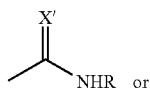

a group of the form $C(=O)OR_3$, a group of the form $C(=O)R_2$ or a group carrying the amine, ammonium quaternary urea or thiourea functionalities, of respective formulae

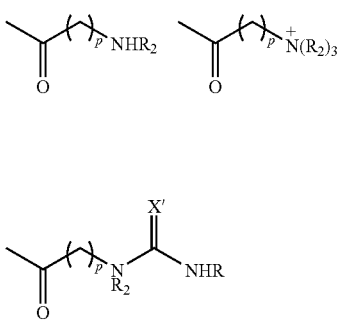

p representing an integer from 0 to 5, when W represents CH,
and from 2 to 5, when W represents N, X' representing O or S, R$_2$ representing a hydrogen atom or an alkyl group comprising from 1 to 6 carbon atoms, and being in particular a methyl, ethyl, propyl or butyl group, R$_3$ representing a substituent allowing the hydrolysis of the carbamate group in order to release the amine function, such as the tert-butyl, 9-fluorenylmethyl, benzyl, allyl or 2,2,2-trichloroethyl groups, and R representing a hydrogen atom, a linear or branched alkyl group of 1 to 12 carbon atoms, or an aromatic group such as the phenyl, benzyl or naphthyl group, or derivatives of these groups carrying substituents on the aromatic ring such as the methyl, ethyl, chlorine, bromine, iodine, nitro, hydroxyl, methoxyl or acetamido substituents, or R representing a biological recognition element such as an amino acid derivative, a peptide, a monosaccharide, an oligosaccharide, a multiplication element with several branchings, which branchings comprise glucide groups which can be identical or different, or also a fluorescent or radioactive visualization or detection probe.

The expression "biological recognition element" designates a complementary molecular structure of a biological receptor, capable of being recognized by the latter and leading to a specific response: induction and regulation of the biosynthesis of an enzyme, inhibition of the activity of an enzyme by binding to its active site, induction of an immune response following a bacterial infection, inhibition of an inflammatory method by blocking of the active site of a selectin, etc.

The expression "multiplication element with several branchings" designates in particular a branched carbon chain comprising either a tetrasubstituted quaternary carbon such as the derivatives of tris(2-aminomethyl)methylamine (TRIS) and of pentaerythritol, or a trisubstituted nitrogen atom such as tris(2-aminoethyl)amine (TREN). These multiplication elements can also be incorporated in combination with a second branching element comprising, in particular, a tertiary nitrogen atom such as the derivatives of tris(2-aminoethyl)amine (TREN).

The expression "fluorescent or radioactive visualization or detection probe" designates a molecular structure allowing the detection of a system by a physicochemical technique, such as fluorescence or radioactivity. Among the fluorescent probes, there can in particular be mentioned the derivatives of fluorescein, dansyl (5-(dimethylamino)-1-naphthalenesulphonyl) or coumarin. Among the radioactive probes, there can be mentioned the products labelled by a radioactive isotope.

The abovementioned formula (I) relates to both symmetrical and non-symmetrical cyclodextrin dimer derivatives. The symmetrical compounds correspond to formula (I) in which n and n' are equal and the non-symmetrical compounds correspond to the formula (I) in which n and n' are different.

In these novel derivatives, it has been noted that the dimer character is useful, in particular for increasing the effectiveness of complexation and solubilization in water of ditopic molecules, in particular the derivatives of paclitaxel, of docetaxel and steroids. The expression "dimerization element" designates a derivative possessing two groups capable of undergoing a coupling reaction with amine-type functionalities situated on the cyclodextrin precursor, in particular two isocyanate or isothiocyanate groups. A useful feature of the present invention is that the dimerization element can be, at the same time, a multiplication element as defined above comprising, in particular, a carbon or trisubstituted nitrogen atom. Two of the substituents on this trisubstituted atom carry the isocyanate or isothiocyanate reactive groups, the third substituent being able to be variable and very diverse in nature. By way of an example of a dimerization element with a trisubstituted carbon atom, there can be mentioned the derivatives of 1,2,3-propanetriamine and, more generally, alkanetriamines, two of the amine groups of which are converted to isocyanate or isothiocyanate. By way of an example of a dimerization element with a trisubstituted nitrogen atom, there can be mentioned the derivatives of tris(2-aminoethyl)amine (TREN), bis(5-aminopentyl)amine and, more generally, of tris and bis(ω-aminoalkane)amines, two of the amine groups of which are converted to isocyanate or isothiocyanate. The coupling reaction of the dimerization element with one of the abovementioned cyclodextrin precursors leads to a cyclodextrin dimer derivative corresponding to the general formula (I) in which W represents CH, when the trisubstituted atom in the dimerization element is a carbon atom, and in which W represents N when it is a nitrogen atom.

A useful feature of the present invention is that the dimerization element can carry a third substituent which can generate a reactive group in a stage subsequent to the dimerization reaction, in particular a carbamate group which can be hydrolyzed in order to generate a free amine group. Optionally, the amine group can carry an alkyl substituent such as a methyl, ethyl, propyl or butyl group. This amine group makes it possible to combine the cyclodextrin dimer with a hydrophilic and cell recognition unit such as a glucide derivative, or also an amino acid or a peptide, by amide, urea and thiourea-type bonds which are very stable and produce well-defined structures. The bond urea or thiourea is created in a last stage and makes it possible to couple the cyclodextrin with numerous substituents, in particular substituents comprising a multiplication element with several branchings, said branchings carrying various glucide units or also a fluorescent or radioactive visualization or detection probe.

The ureido-, thioureido- ureidocysteaminyl- and thioureidocysteaminyl-cyclodextrin dimers corresponding to formula (I) given above in which W represents CH or N and Z represents a substituent carrying an amine functionality of the $NHR_1$ type ($R_1$=H or alkyl substituent), and in all cases where Z represents N, can be isolated in the form of ammonium salt or free base. They are always isolated in the form of ammonium salt when Z comprises a quaternary ammonium group, positively charged, of the $^+N(R_2)_3$ type ($R_2$=alkyl substituent). In the case of the salt, the counter-ion is a monovalent anion, in particular a halide such as chloride, bromide or iodide. The compounds of formula (I), in which W represents CH or N, and Z represents a substituent carrying an amine group of the $NHR_1$ type, or W represents N and Z represents H, can be used as precursors for the incorporation of novel substituents on the cyclodextrin dimer, in particular by formation of a novel urea or thiourea bond. When Z in formula (I) carries an $NH_2$ group, the ureas and thioureas obtained are N,N'-disubstituted, whereas, when Z carries an $NHR_2$ group, $R_2$ representing an alkyl substituent, such as methyl, ethyl, propyl or butyl, or when W=N and Z=H, the ureas and thioureas obtained are N,N'N''-trisubstituted.

In the case of the ureido-, thioureido-, ureidocysteaminyl- and thioureidocysteaminyl-cyclodextrin dimers of formula (I), in which Z represents a substituent comprising a thiourea group of the $NR_2C(=X')NHR$ type, the R substituents can be of various types. Thus, R can represent a hydrogen atom, an alkyl substituent with 1 to 12 carbon atoms, linear or branched, or an aromatic group such as phenyl, benzyl, naphthyl or derivatives of these groups carrying substituents on the aromatic ring, said substituents being as defined previously. R can also represent, in particular, groups derived from amino acids, peptides, monosaccharides or oligosaccharides, optionally substituted. By way of examples of groups derived from monosaccharides, there can be mentioned those derived from glucose, mannose and galactose, in α or β anomeric configuration. In the case where the group derived from the monosaccharide is substituted, one or more of the hydroxyl groups of the monosaccharide can be replaced by alkoxy groups of 1 to 16 carbon atoms, acyloxy groups such as the acetoxy group, amine and amide groups. The groups derived from oligosaccharides can be the maltosyl, maltotriosyl, lactosyl groups, or also tri- or tetrasaccharides cell affinity markers of the Lewis X or sialyl Lewis X type, or also the oligosaccharides derived from heparin. They can also be substituted by alkoxy, acyloxy groups, amine, sulphates or phosphate groups.

According to the invention, R can also represent a group comprising a branched multiplication element, for example a group derived from tris(2-hydroxymethyl)methylamine (TRIS), pentaerythritol or tris(2-aminoethyl)amine (TREN), comprising in the branchings groups derived from mono- or oligosaccharides which can be identical or different. By way of examples, there can be mentioned the groups derived from mono- or oligosaccharides already mentioned previously, which can also comprise oxygenated or aminated substituents. These glucide groups can be linked to the multiplication element by an oxygenated, sulphur-containing or aminated bond. In the case where R comprises a branching element, one of the branchings can also carry a probe of fluorescent type, in particular a fluorescein derivative or also a radioactive probe. These multiplication elements can also be incorporated in combination with a second branching element comprising, in particular, a tertiary nitrogen atom such as the derivatives of the tris(2-aminoethyl)amine (TREN).

An advantageous compound according to the present invention is a compound as defined above, characterized in that n and n' are equal.

Such a compound is a symmetrical compound and is therefore more readily accessible and more easily characterizable by the standard physico-chemical methods than a non-symmuetrical compound.

Such a compound corresponds to the following formula (A):

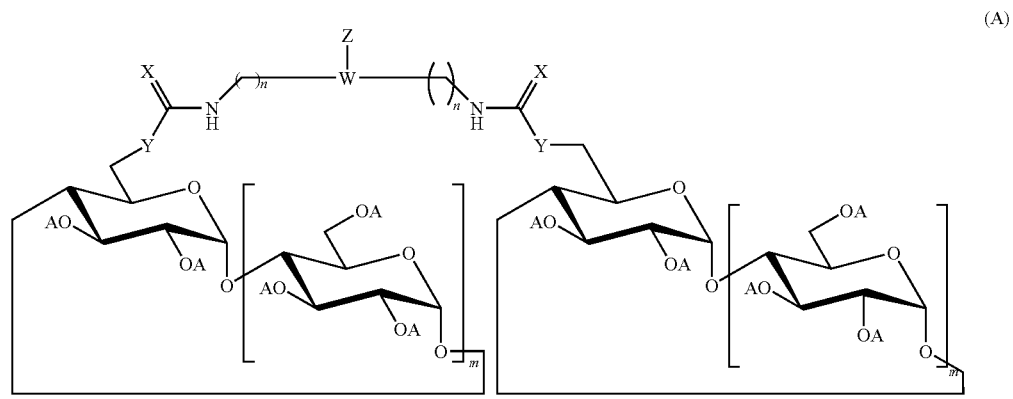

in which m, n, A, X, Y, W and Z are as defined above.

An advantageous compound according to the present invention is a compound as defined above, characterized in that all the A groups represent a hydrogen atom.

Such compound corresponds to the following formula (B):
in which m, n, X, Y, W and Z are as defined above.

The present invention also relates to a compound as defined above, characterized in that Y represents either an $NR_1$ group, or an —NH—CO—$(CH_2)_q$—$NR_1$— group, or an —S—$(CH_2)_r$—$NR_1$— group, and corresponding to one of the following formulae respectively:

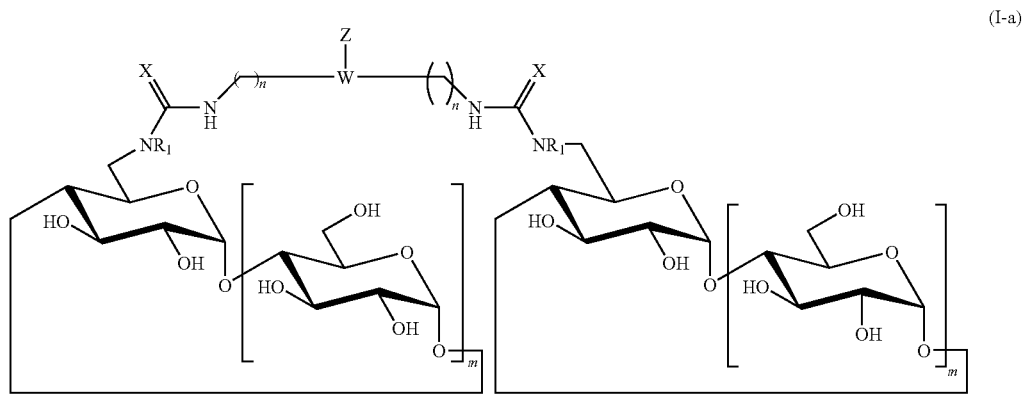

(I-a)

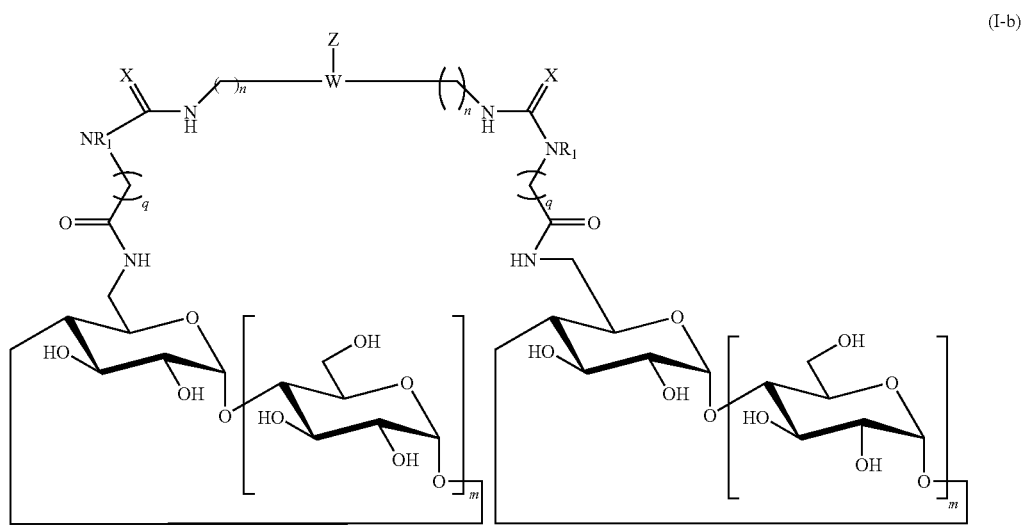

(I-b)

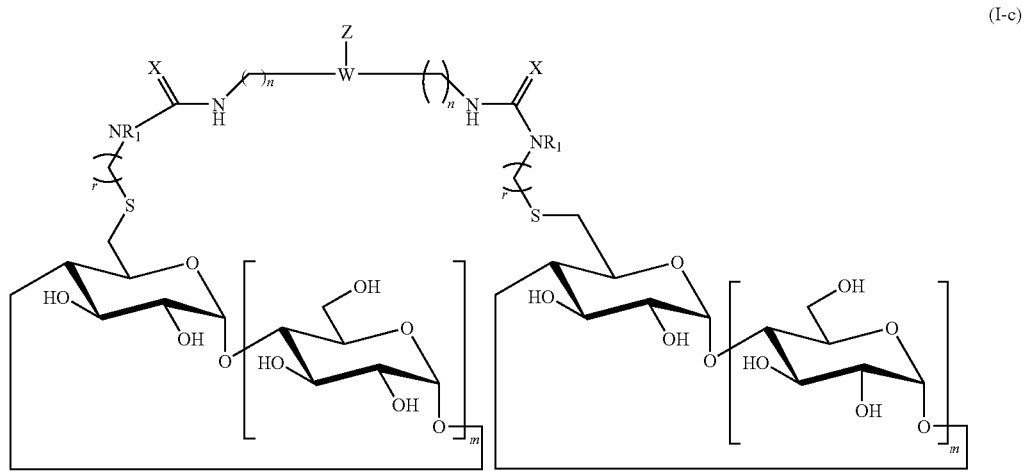

(I-c)

in which n, m, q, r, X, W, Z and $R_1$ are as defined above.

The abovementioned compounds are compounds monosubstituted on each cyclodextrin ring. In this type of compound, access to the cavity of the cyclodextrin is less obstructed than in the case of polysubstituted derivatives. Moreover, the dimer character can provide better complexation abilities for certain ditopic guest molecules.

The compounds of formula (I-a) and (I-b) are dimer compounds derived from cyclodextrin, named ureido- and thioureido-cyclodextrin dimers. The compounds of formula (I-c) are dimer compounds derived from cyclodextrin, named ureidocysteaminyl- and thioureidocycteaminyl-cyclodextrin dimers.

An advantageous compound according to the present invention is characterized in that Z represents either a $-(CH_2)_p-NHR_2$ group, or a $-(CH_2)_p-N(R_2^+)_3$ group, or a group of formula

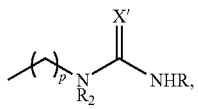

in which X' represents a sulphur atom, and corresponding to one of the following formulae respectively:

in which n, m, p, X, W, Y, R and $R_2$ are as defined above.

These compounds are particularly useful to the extent that they provide access to a range of products with physico-chemical properties which can be varied with respect in particular to solubility, neutral or charged character, useful for membrane interactions, or also properties of recognition vis-à-vis biological receptors.

An advantageous compound according to the present invention is a compound as defined above, characterized in (I-d)

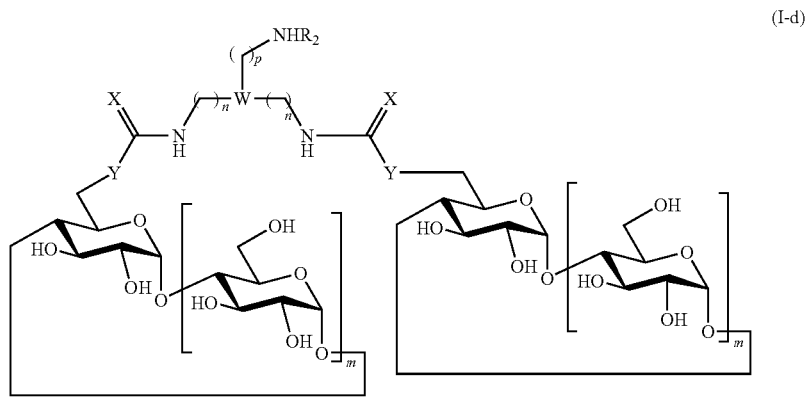

(I-e)

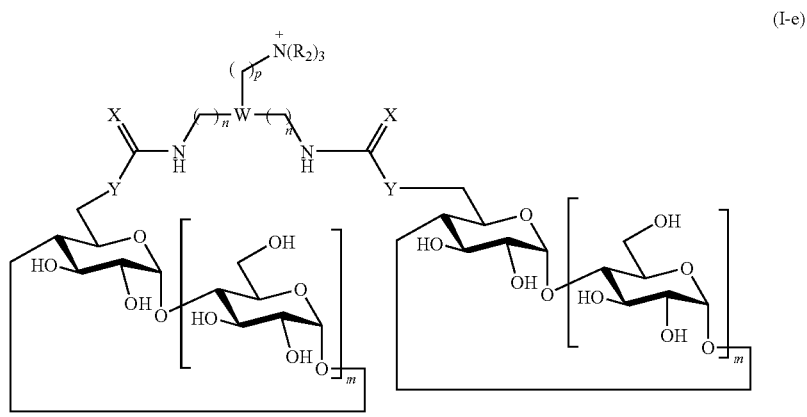

(I-f)

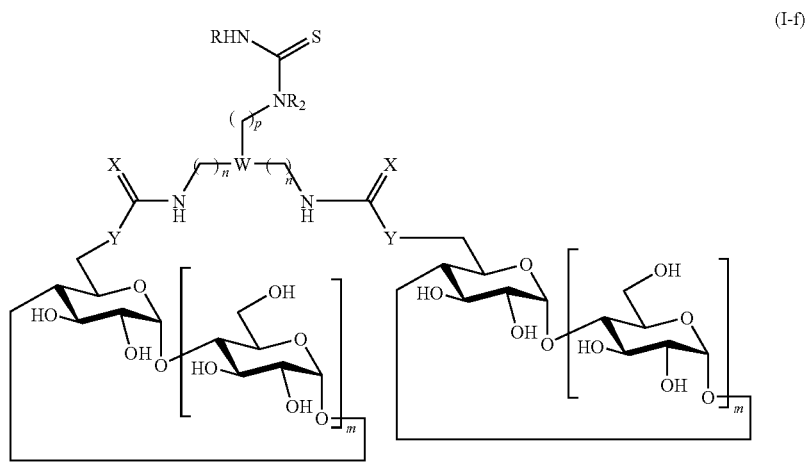

that W represents a nitrogen atom and in that Z represents either a group of formula —CO—(CH$_2$)$_p$—NHR$_2$, or a group of formula —CO—(CH$_2$)$_p$—N$^+$(R$_2$)$_3$, or a group of formula
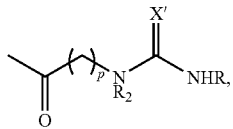
in which X' represents a sulphur atom, or a group of formula
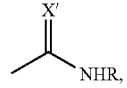
in which X' represents a sulphur atom and corresponding to one of the following formulae respectively:
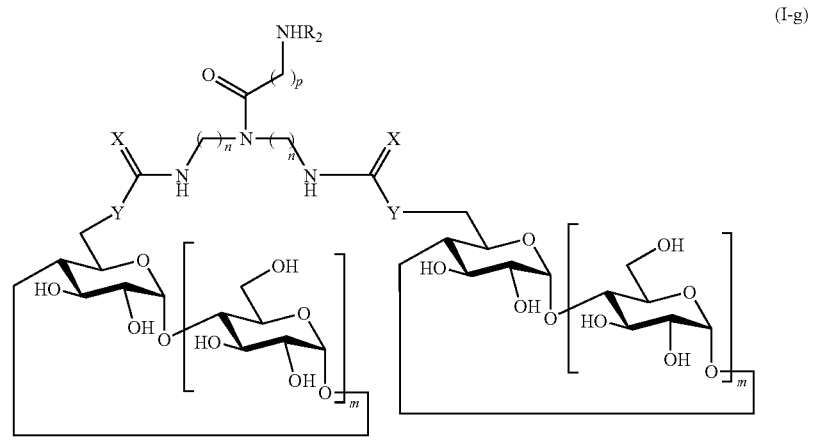
(I-g)
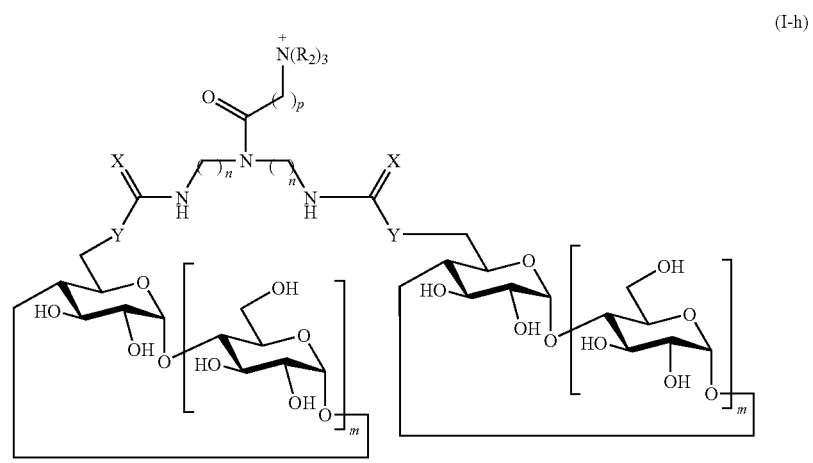
(I-h)

-continued

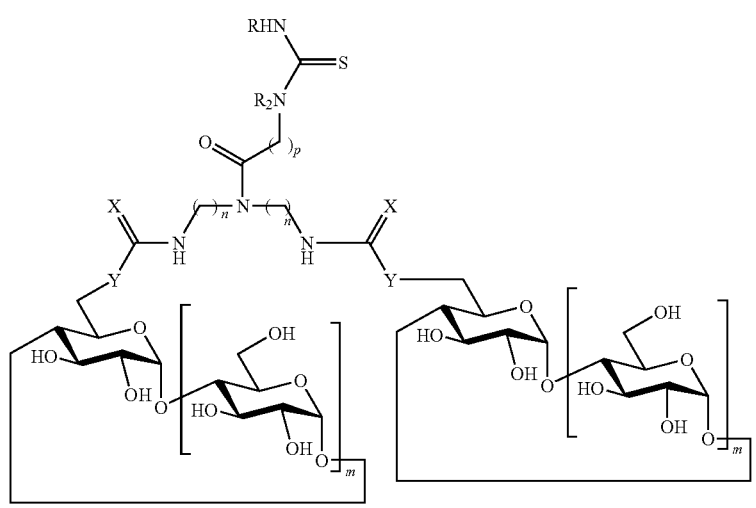
(I-i)

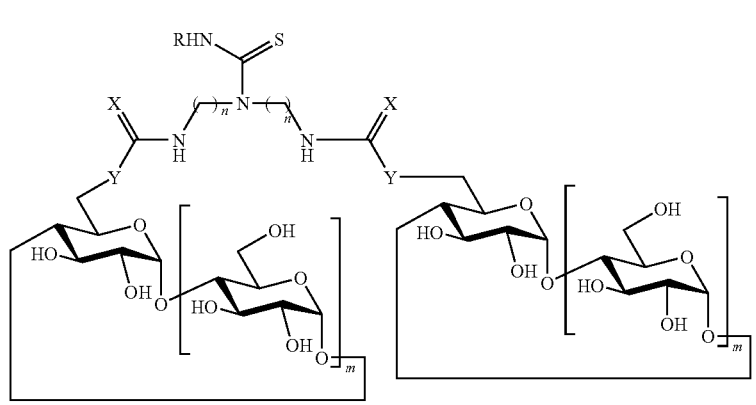
(I-j)

in which n, m, p, X, Y, R and $R_2$ are as defined above.

A preferred compound according to the present invention is a compound as defined above, of formula (I), characterized in that n is equal to 2, X represents a sulphur atom, W represents a nitrogen atom and Y represents an NH group.

Such a compound corresponds to the following formula (C):

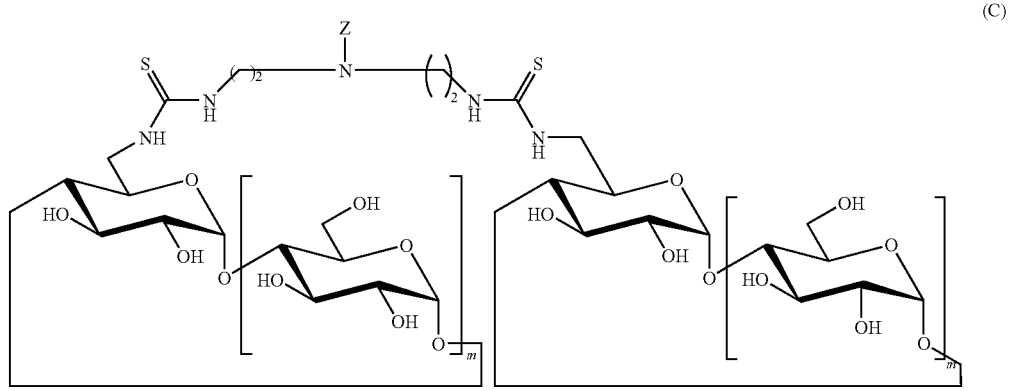
(C)

in which m and Z are as defined above.

Such a compound has a non-charged character and is readily accessible in few stages from a large variety of commercial base units.

A preferred compound -according to the present invention is a compound as defined above, of formula (C), characterized in that Z represents one of the following groups: —(CH$_2$)$_2$—NH$_2$, —(CH$_2$)$_2$—NH—CS—NHR or —(CH$_2$)$_2$—NHBoc (Boc=tert-butoxycarbonyl), R being as defined above, and corresponding to one of the following formulae:

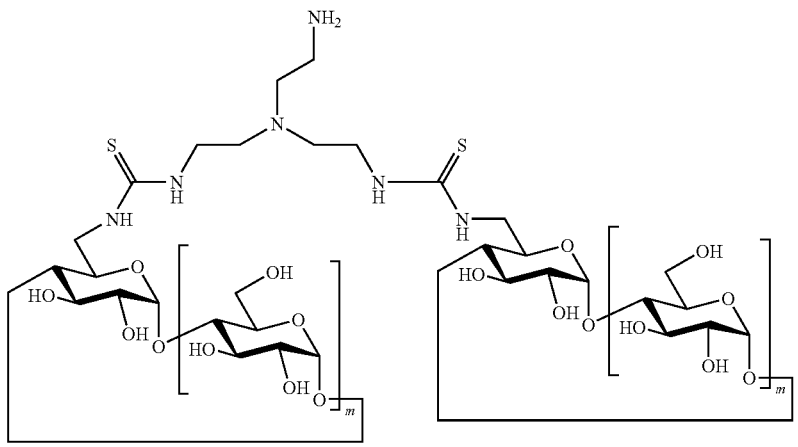

(D)

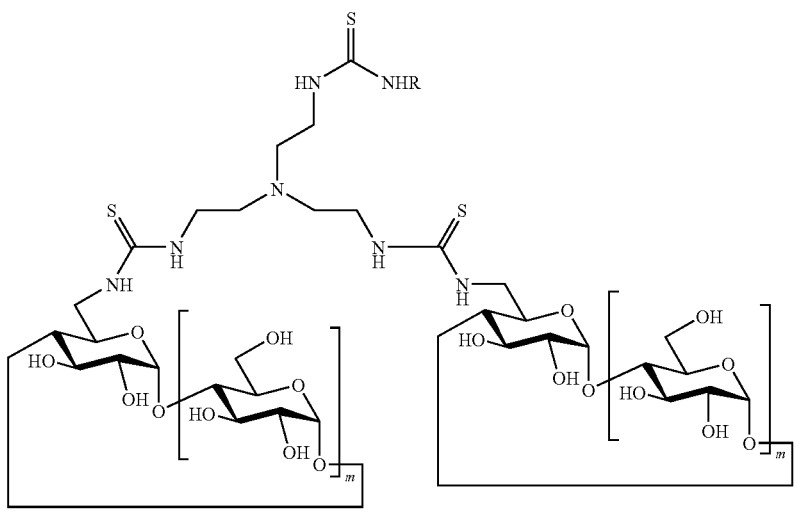

(E)

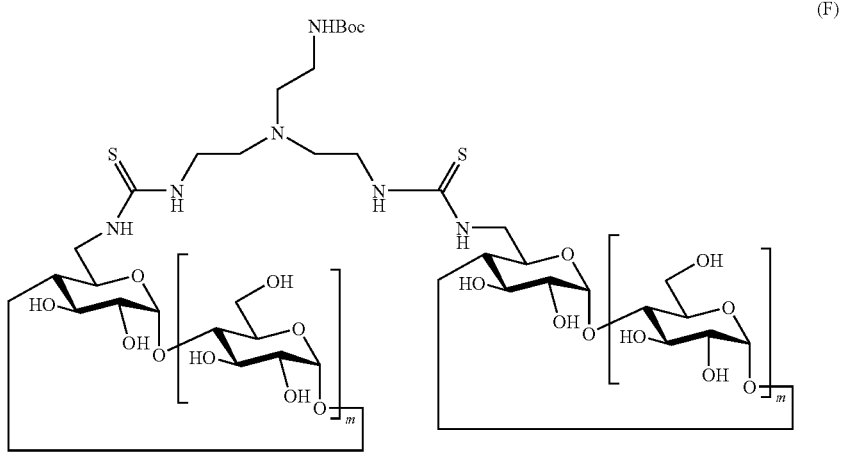

(F)

m being as defined above.

The abovementioned compounds of formulae (D), (E) and (F) have a clearly basic character and can optionally be protonated in the form of salts. They can be useful for targeting entities with an acid character.

According to an advantageous embodiment, the compounds of the invention are characterized in that R is chosen from the following groups:
- an alkyl group of 1 to 12 carbon atoms, linear or branched, and preferably being the methyl group;
- an aromatic group such as phenyl, benzyl, naphthyl or derivatives of these groups carrying substituents on the aromatic ring, and preferably being the phenyl group;
- the α-D-mannopyranosyl group, of the following formula (III):

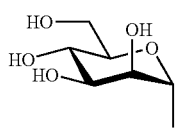

(III)

the β-lactosyl group, of the following formula (III-a):

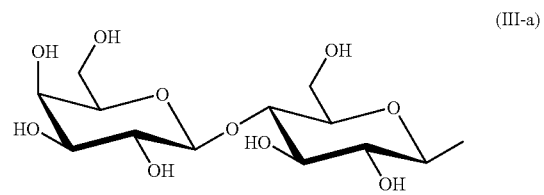

(III-a)

the group derived from Lewis X trisaccharide or sialyl Lewis X tetrasaccharide, of the following formulae (III-b) and (III-c) respectively:

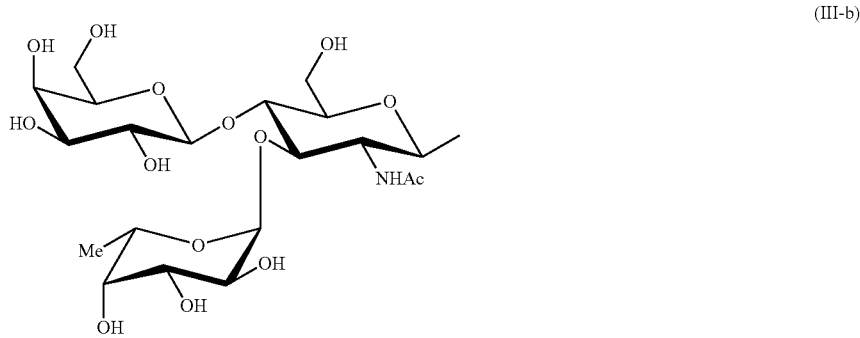

(III-b)

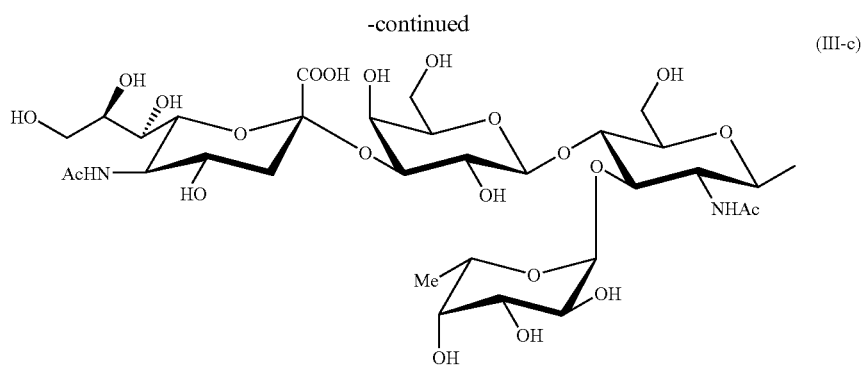
an oligosaccharide derived from heparin, of the following formula (III-d):
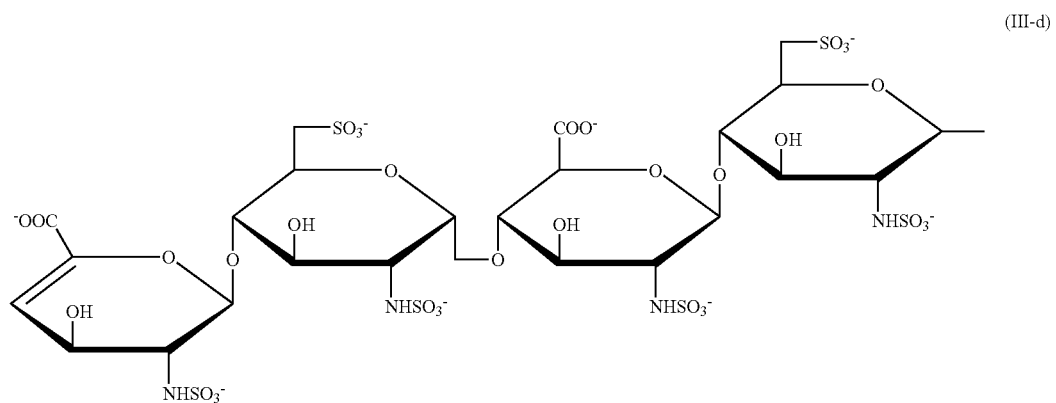
Thus, the present invention relates in particular to the compounds corresponding to one of the following formulae:
compound of formula (E) in which R represents the methyl group:
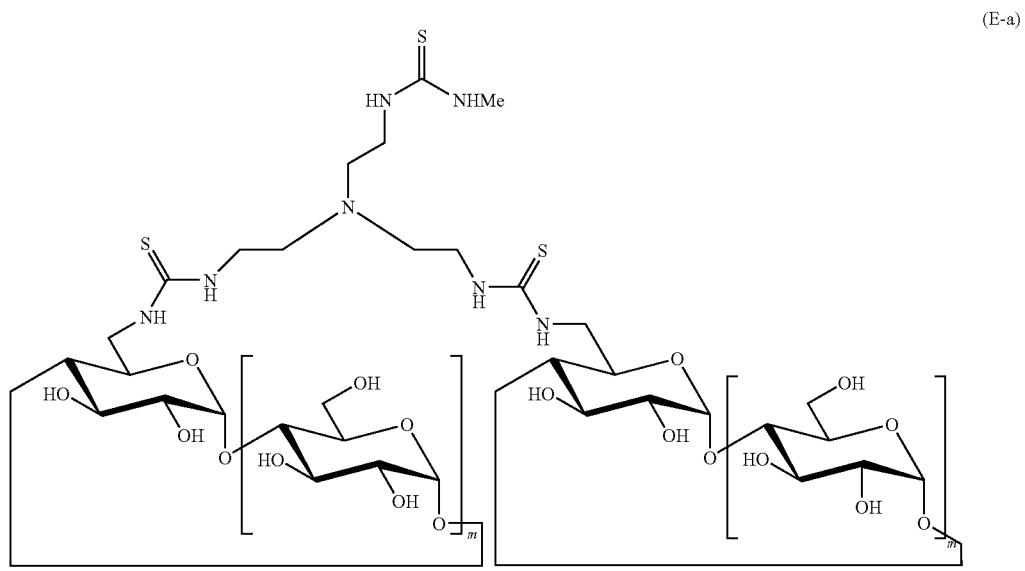

compound of formula (E) in which R represents the phenyl group:
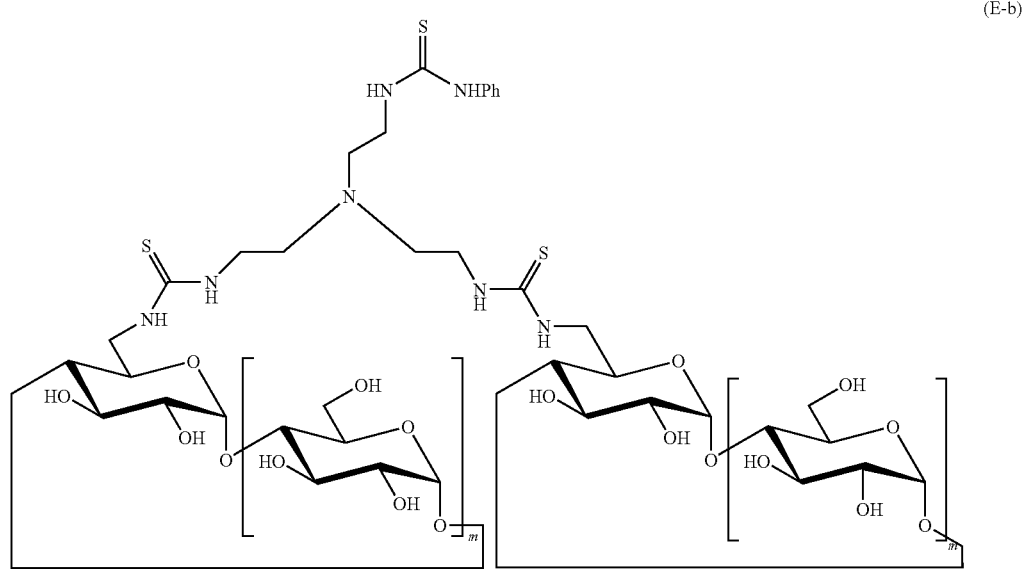
(E-b)
compound of formula (E) in which R represents the α-D-mannopyranosyl group of the abovementioned formula (III):
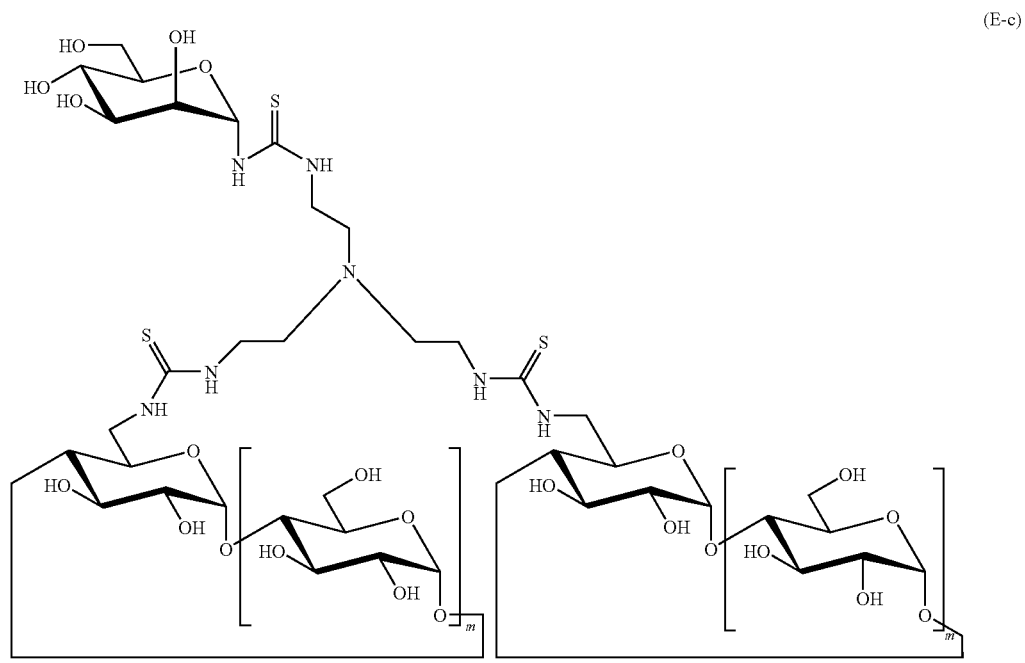
(E-c)

compound of formula (E) in which R represents the β-lactosyl group of the abovementioned formula (III-a):
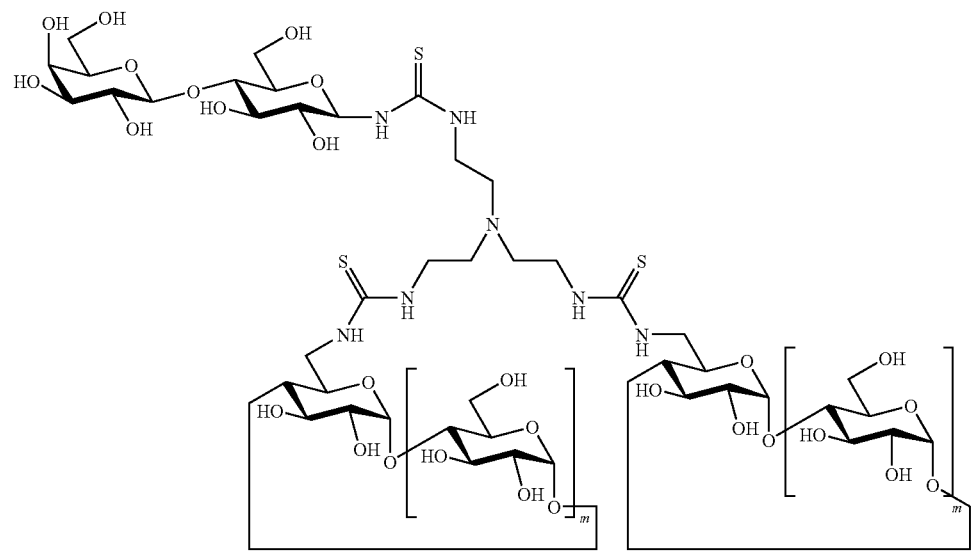
(E-d)
compound of formula (E) in which R represents the group derived from the Lewis X trisaccharide of the abovementioned formula (III-b):
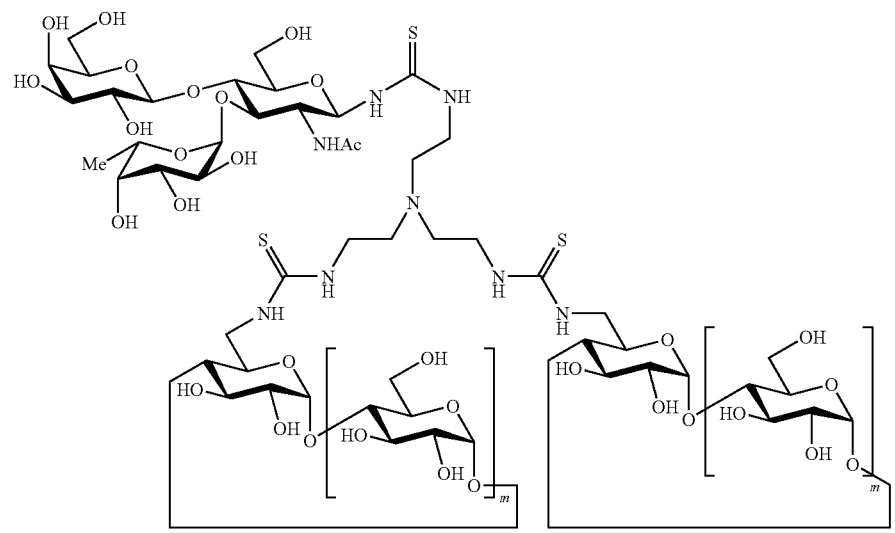
(E-e)

compound of formula (E) in which R represents the group derived from the sialyl Lewis X tetrasaccharide of the abovementioned formula (III-c):
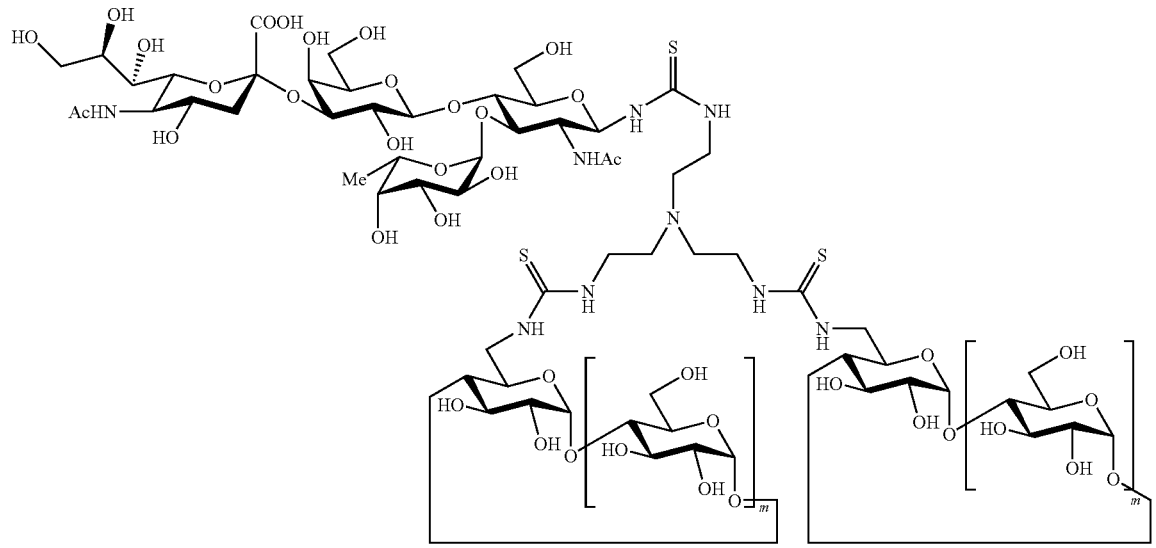
(E-f)
compound of formula (E) in which R represents an oligosaccharide derived from heparin, such as the oligosaccharide of the abovementioned formula (III-d):
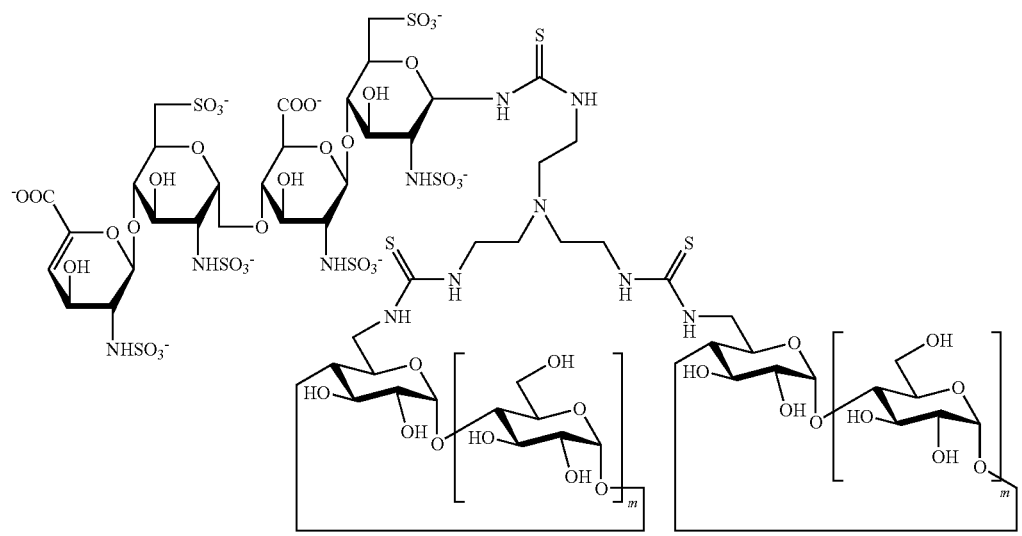
(E-g)

The present invention also relates to a compound as defined above, in particular of formula (I), characterized in that R comprises a branching element derived from tris(2-hydroxymethyl)methylamine, and represents one of the following groups:

the tris(α-D-mannopyranosyloxymethyl)methyl group, of the following formula (IV):

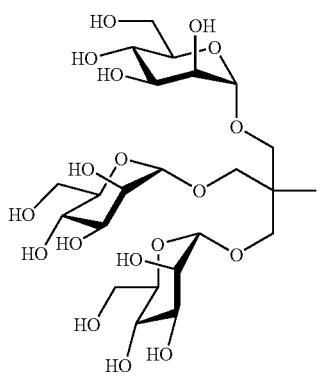

(IV)

the tris(β-lactosyloxymethyl)methyl group, of the following formula (IV-a):

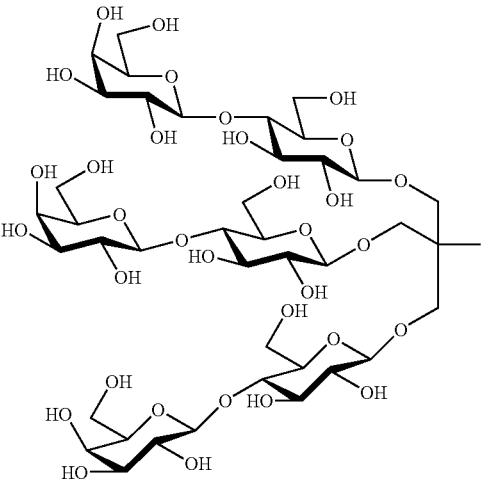

(IV-a)

Thus, the present invention relates in particular to the compounds corresponding to one of the following formulae:
compound of formula (E) in which R represents the tris(α-D-mannopyranosyloxymethyl)methyl group, of the abovementioned formula (IV):

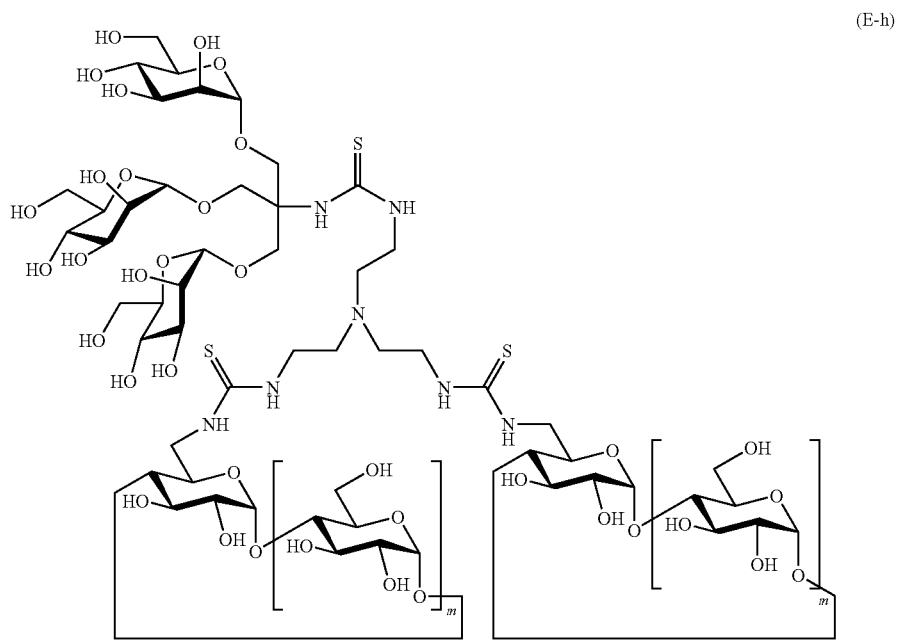

(E-h)

compound of formula (E) in which R represents the tris(β-lactosyloxymethyl)methyl group, of the abovementioned formula (IV-a):
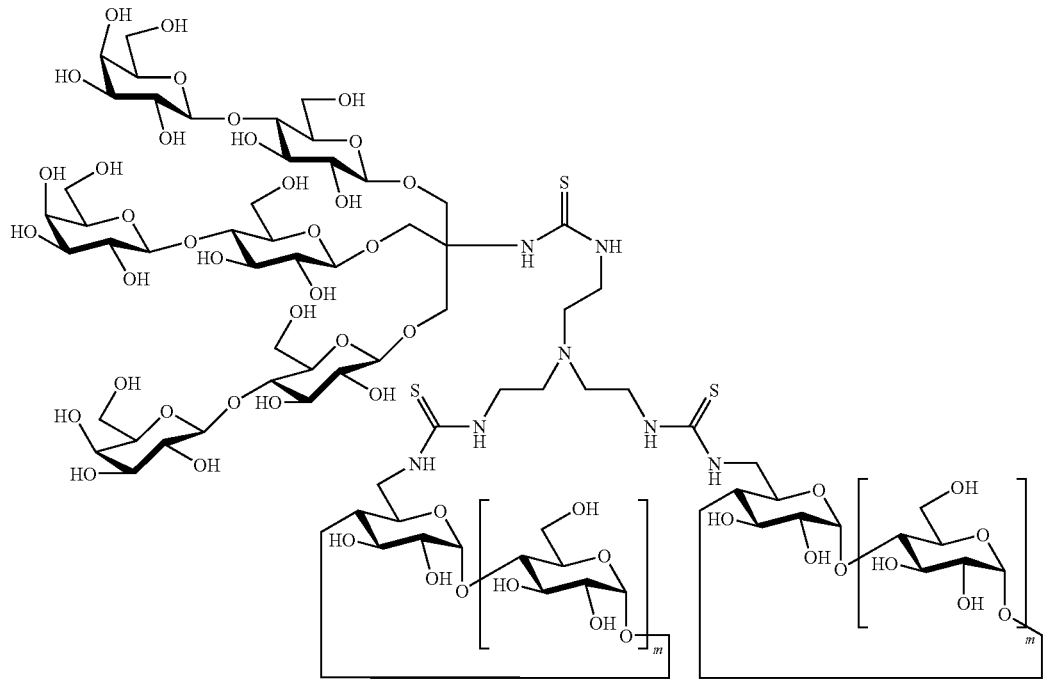
(E-i)
The present invention also relates to a compound as defined above, of formula (I), characterized in that R comprises a branching element derived from pentaerythritol, said compound corresponding to one of the following formulae:
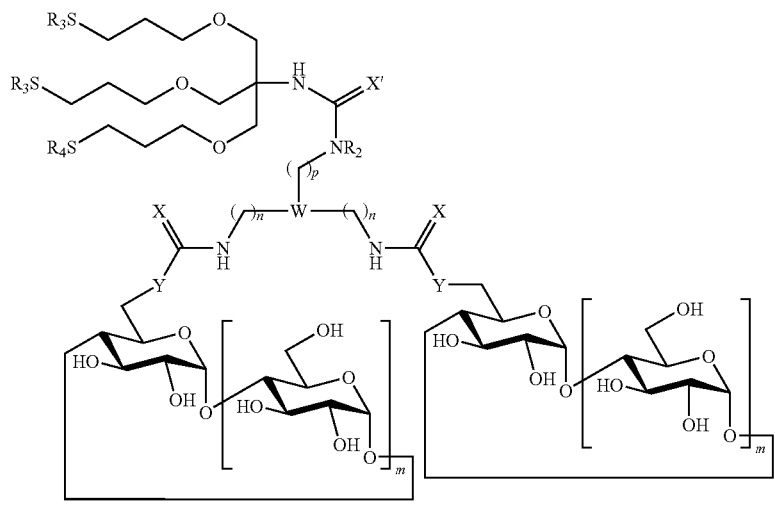
(II-a)

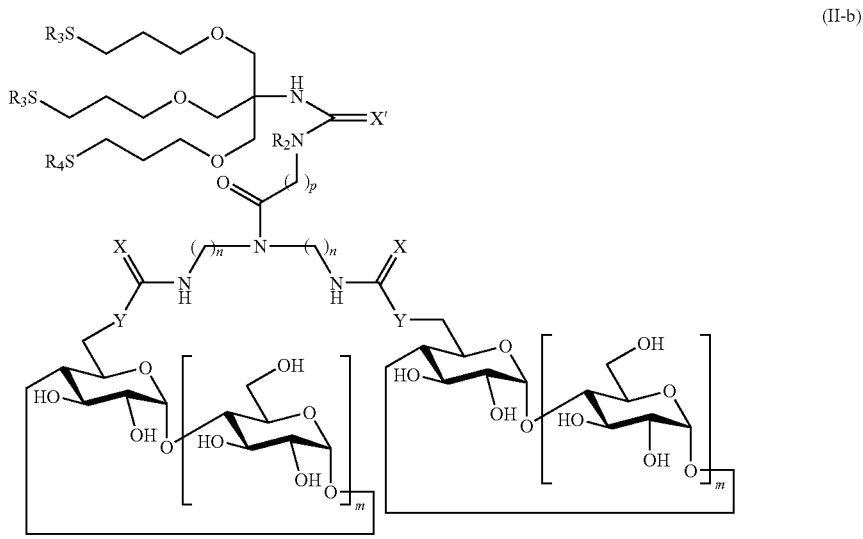

(II-b)

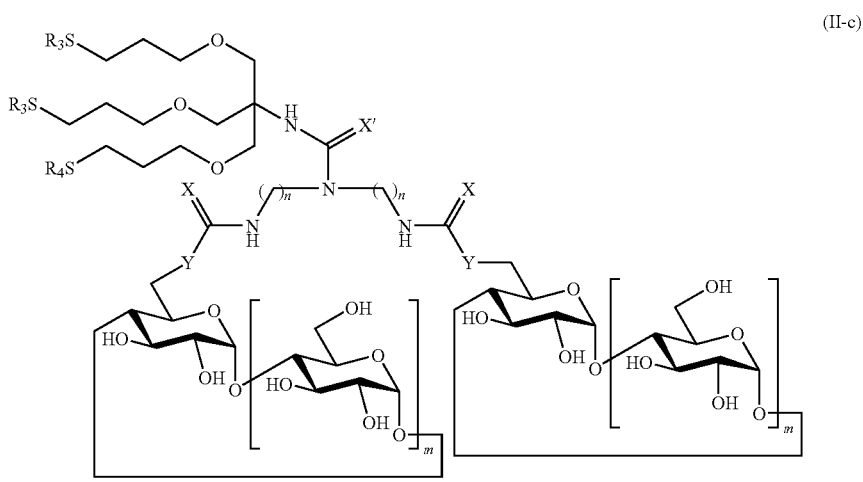

(II-c)

in which m, n, p, X, X', Y are as defined above, and R₃ and R₄ represent glucide derivatives which can be different or identical or also a fluorescent or radioactive probe.

The present invention also relates to a compound as defined above, corresponding to the abovementioned formulae (I-f), (I-i) or (I-j), characterized in that R comprises a branching element derived from pentaerythritol, said compound corresponding to one of the following formulae (II-a-a), (11-b-a) or (II-c-a):

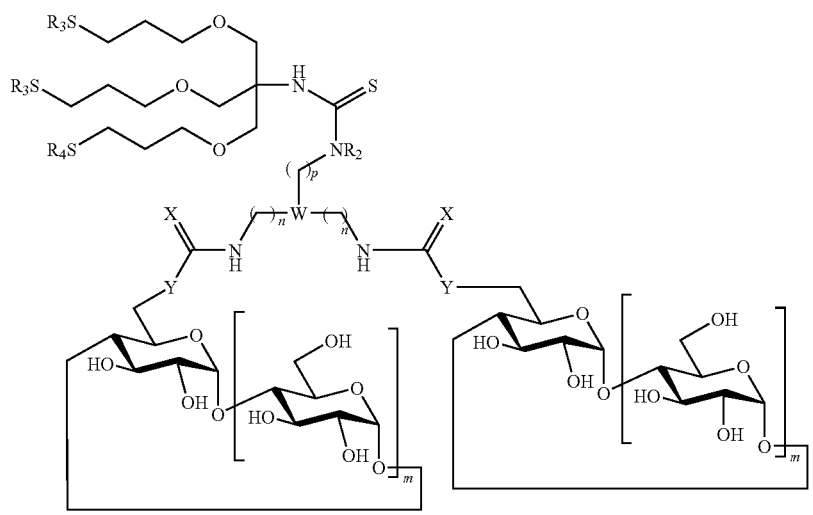
(II-a-a)
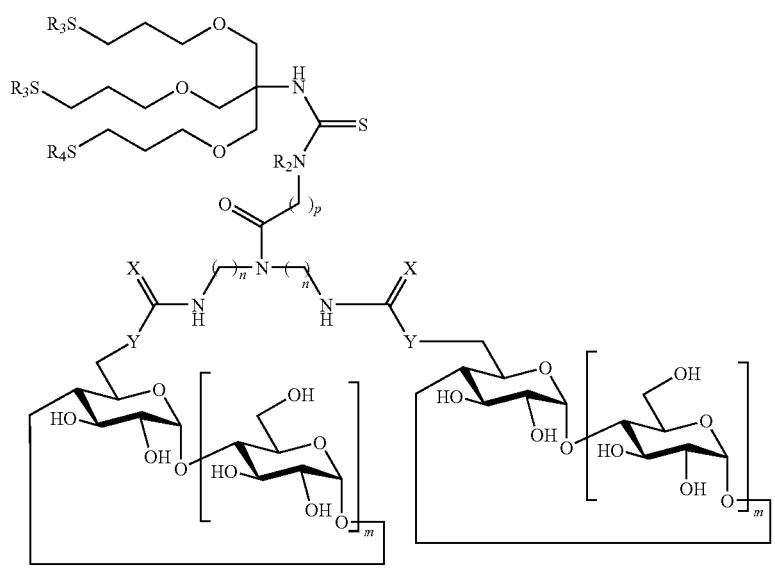
(II-b-a)

-continued

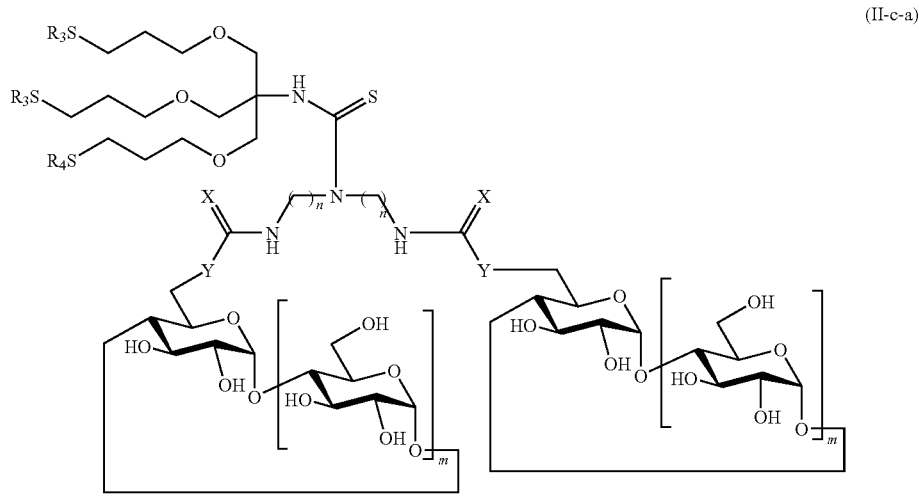

(II-c-a)

in which m, n, p, X, Y, $R_3$ and $R_4$ are as defined above.

An advantageous compound according to the present invention is a compound corresponding to the abovementioned formula (II-a), in which n and p are equal to 2, X and X' represent a sulphur atom, Y represents an NH group and $R_2$ represents a hydrogen atom. Such a compound corresponds to the following formula (G):

The present invention also relates to a compound as defined above, corresponding to one of the formulae (II-a), (II-b) or (II-c), characterized in that $R_3$ and $R_4$ represent one of the following groups:

the α-D-mannopyranosyl group, of formula (III) as defined above, or the β-lactosyl group, of formula (III-a) as defined above, or

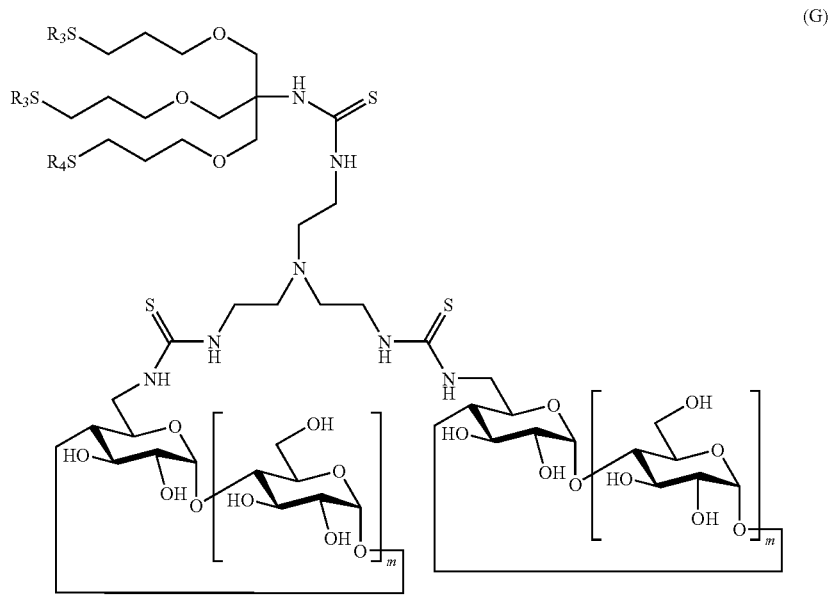

(G)

the β-D-glucopyranosyl group, of the following formula (VI):

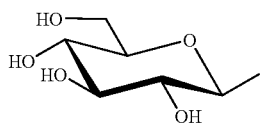

(VI)

$R^3$ and $R^4$ being able to be identical or different.

The preferred compounds of the invention are in particular compounds of formula (G) in which the substituents $R_3$ and $R_4$ are as defined above. Such compounds correspond to the following formulae:

compound of formula (G) in which $R_3$ and $R_4$ represent an α-D-mannopyranosyl group, of the abovementioned formula (III):

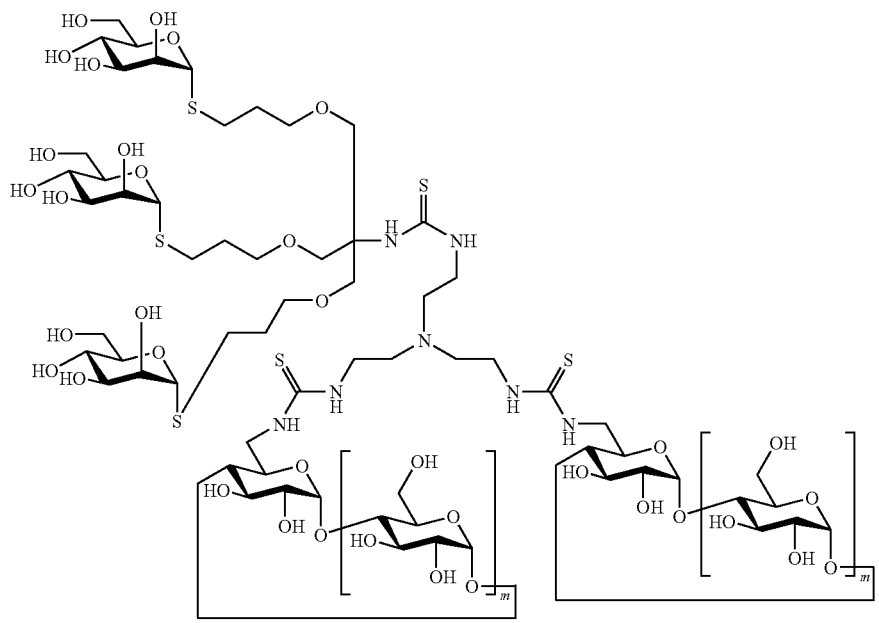

(G-a)

compound of formula (G) in which $R_3$ and $R_4$ represent a β-D-glucopyranosyl group, of the abovementioned formula (VI):

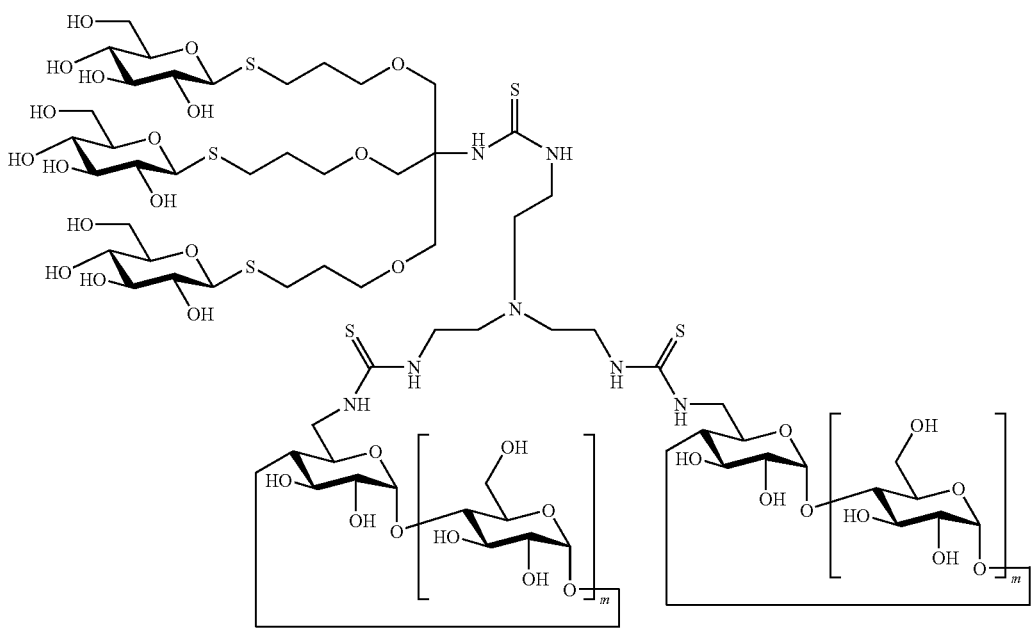

(G-b)

compound of formula (G) in which R₃ and R₄ represent a
β-lactosyl group, of the abovementioned formula (III-a):
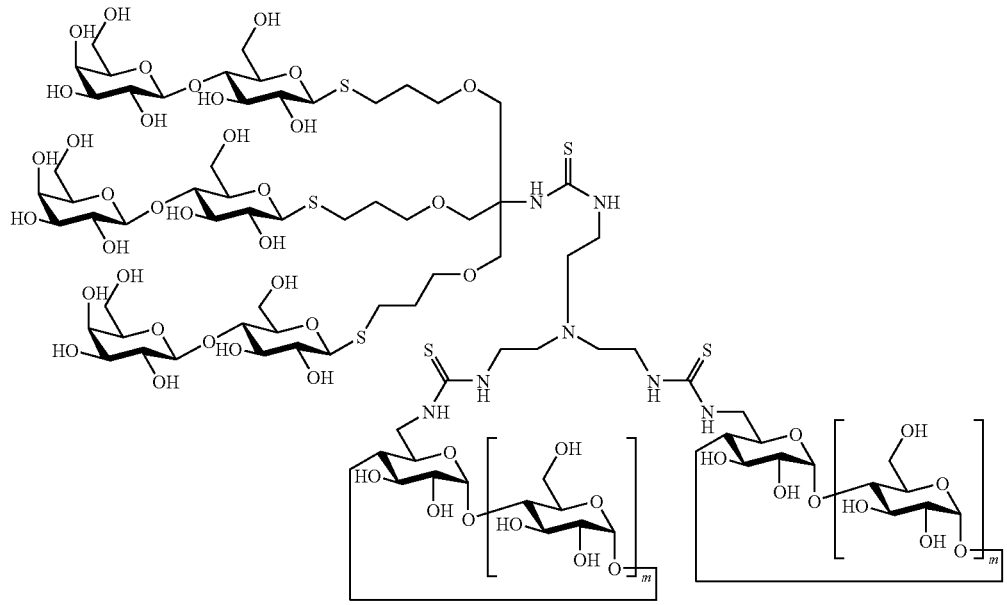
(G-c)
compound of formula (G) in which R₃ represents an α-D-
mannopyranosyl group of the abovementioned formula
(III), and R₄ represents a β-D-glucopyranosyl group, of
the abovementioned formula (VI):
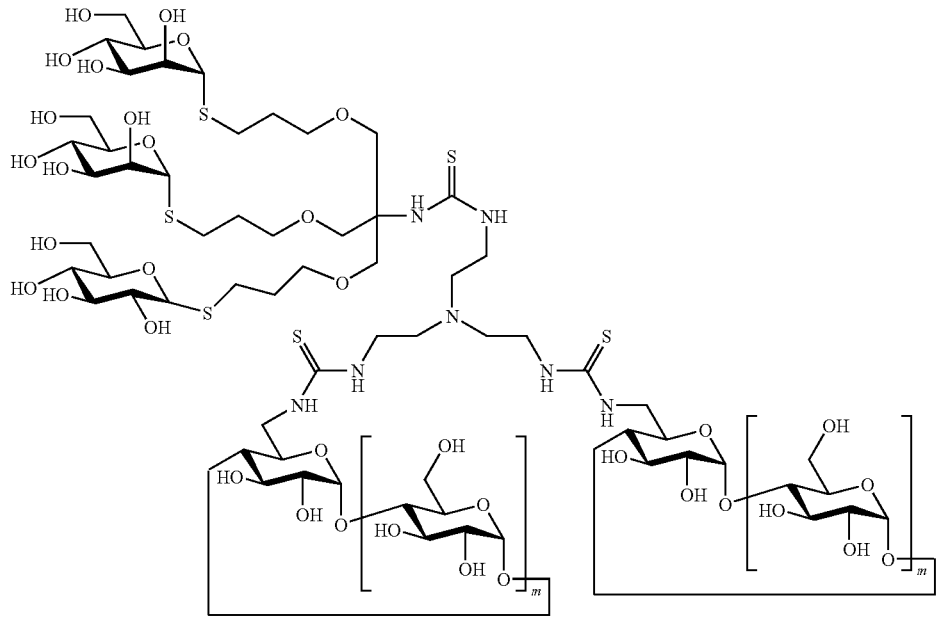
(G-d)

compound of formula (G) in which R₃ represents an α-D-mannopyranosyl group of the abovementioned formula (III), and R₄ represents a β-lactosyl group, of the abovementioned formula (III-a):

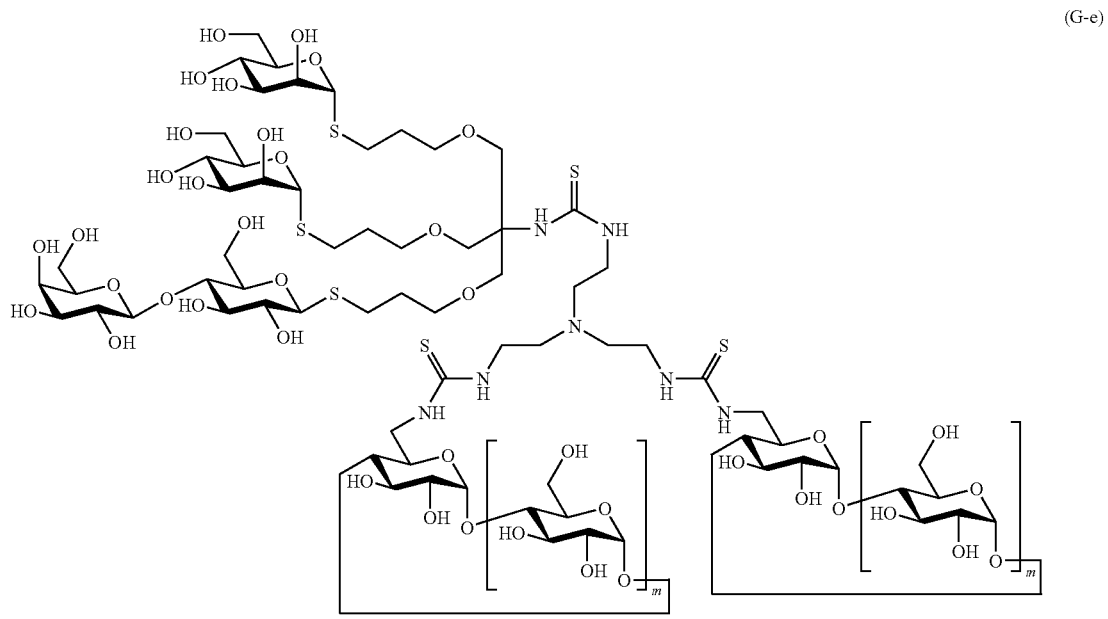

(G-e)

compound of formula (G) in which R₃ represents a β-D-glucopyranosyl group, of the abovementioned formula (VI), and R₄ represents an α-D-mannopyranosyl group, of the abovementioned formnula (III):

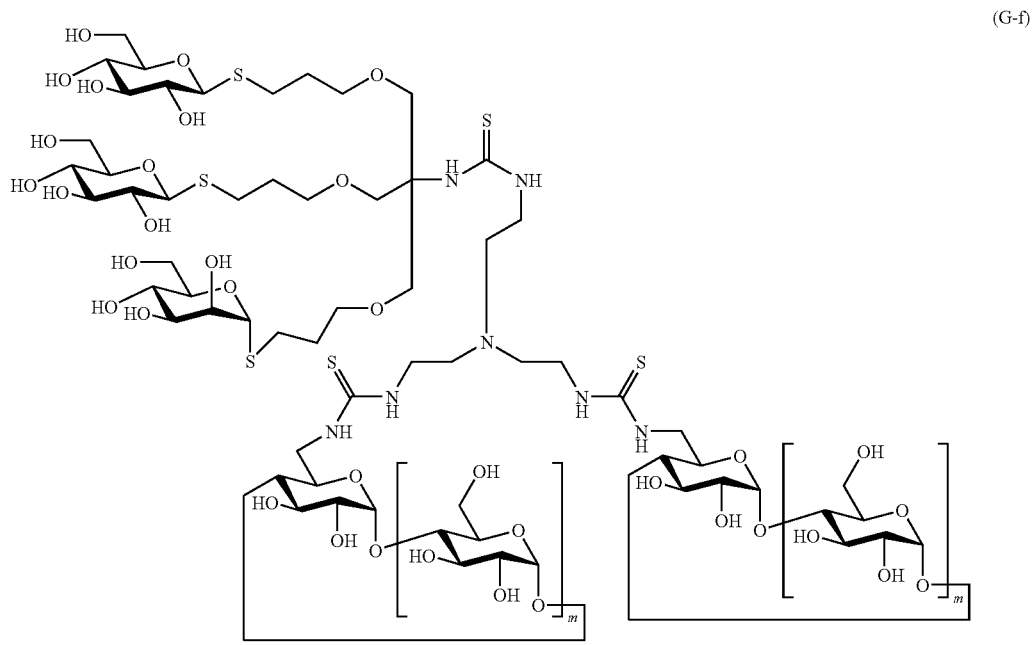

(G-f)

compound of formula (G) in which $R_3$ represents a β-D-glucopyranosyl group, of the abovementioned formula (VI), and $R_4$ represents a β-lactosyl group, of the abovementioned formula (III-a):

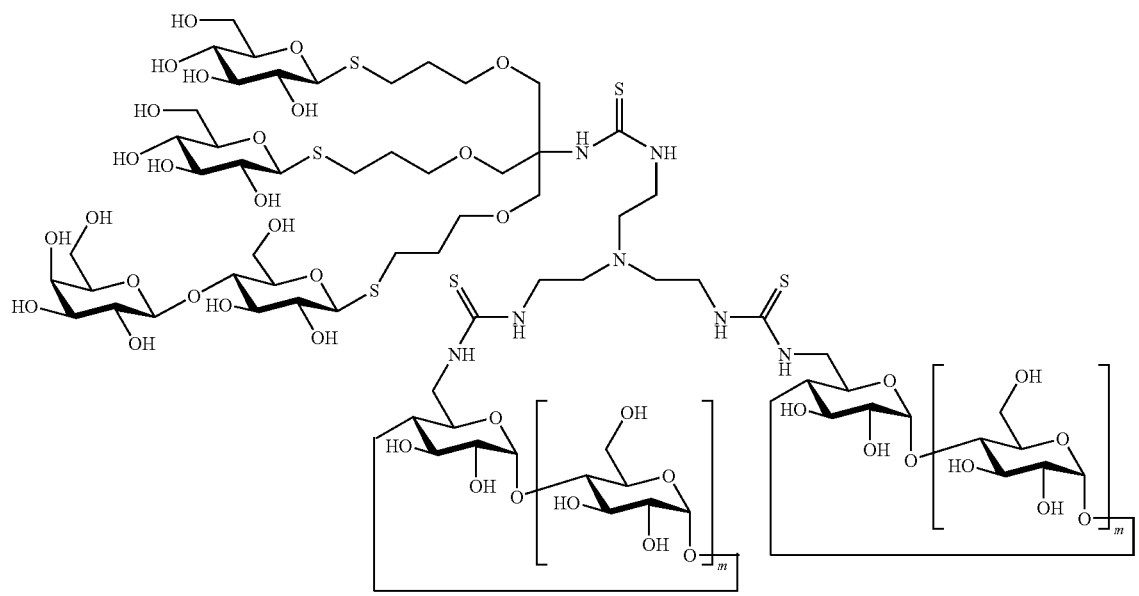

(G-g)

compound of formula (G) in which $R_3$ represents a β-lactosyl group, of the abovementioned formula (III-a), and $R_4$ represents an α-D-mannopyranosyl group, of the abovementioned formula (III):

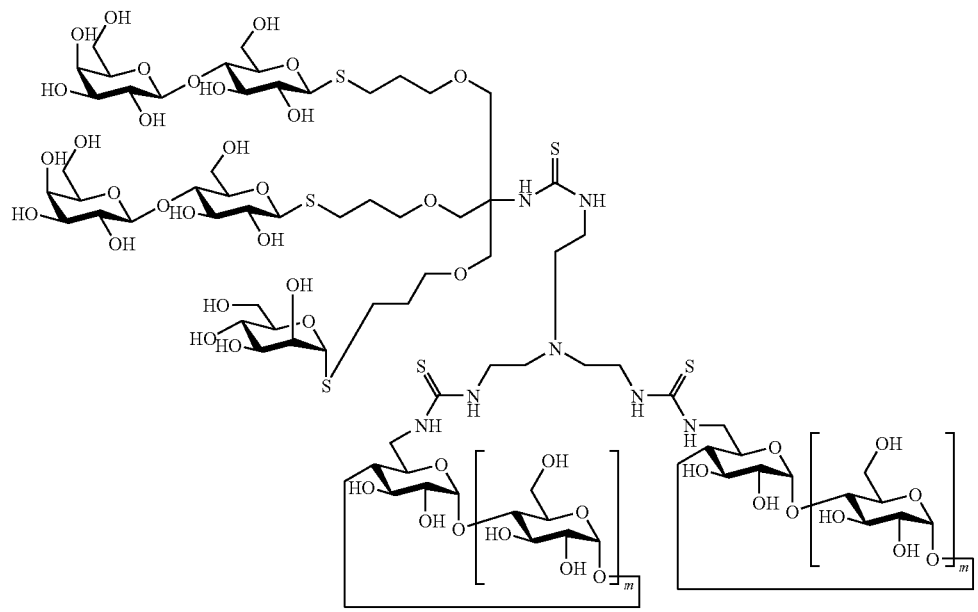

(G-h)

compound of formula (G) in which $R_3$ represents a β-lactosyl group, of the abovementioned formula (III-a), and $R_4$ represents an α-D-glucopyranosyl group, of the abovementioned formula (VI):

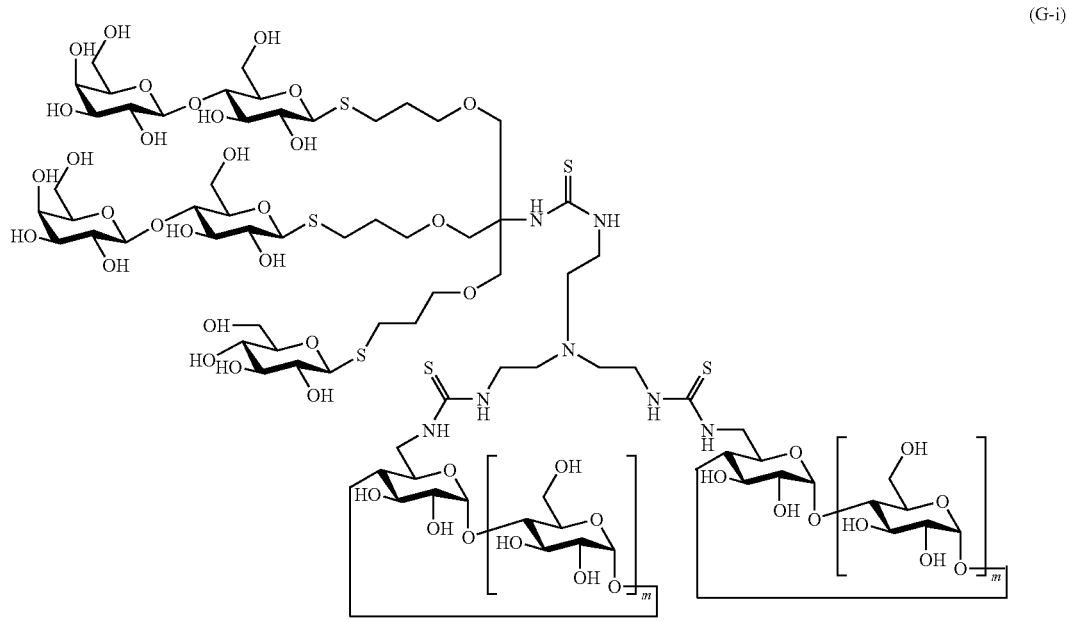

(G-i)

The present invention also relates to a compound as defined above, of formula (I), characterized in that R comprises a branching element derived from tris(2-aminoethyl)amine (TREN), said compound corresponding to one of the following formulae:

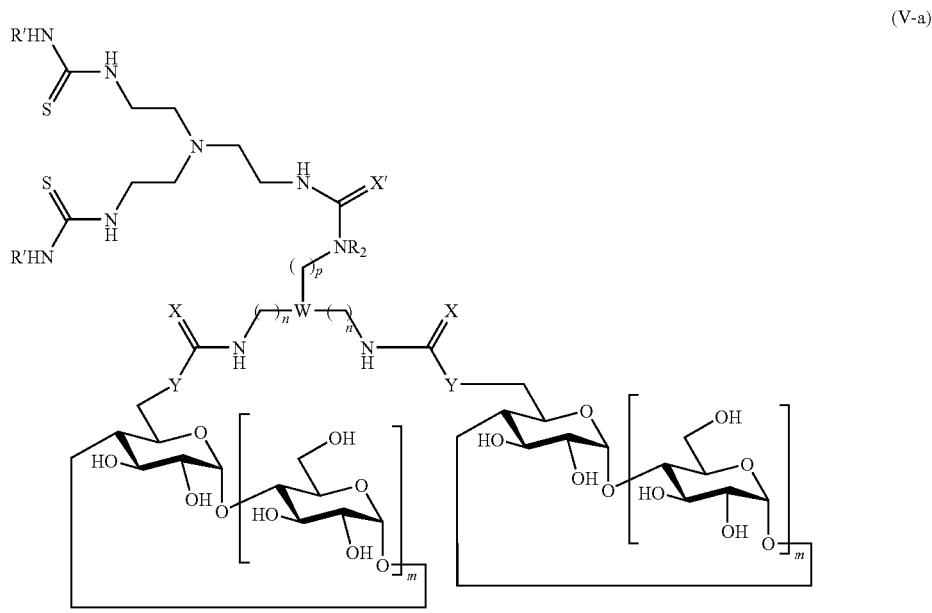

(V-a)

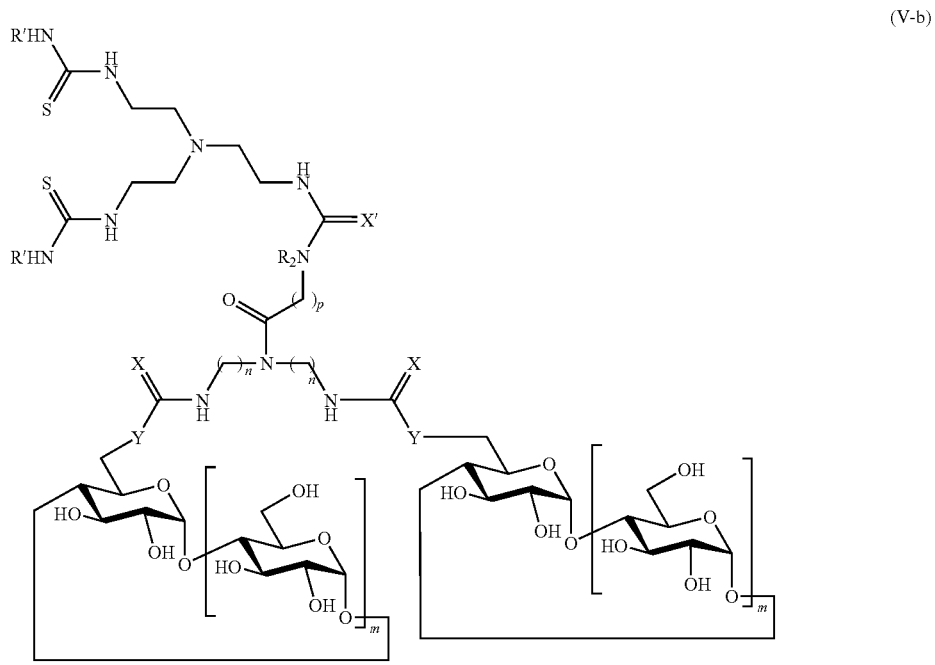

(V-b)

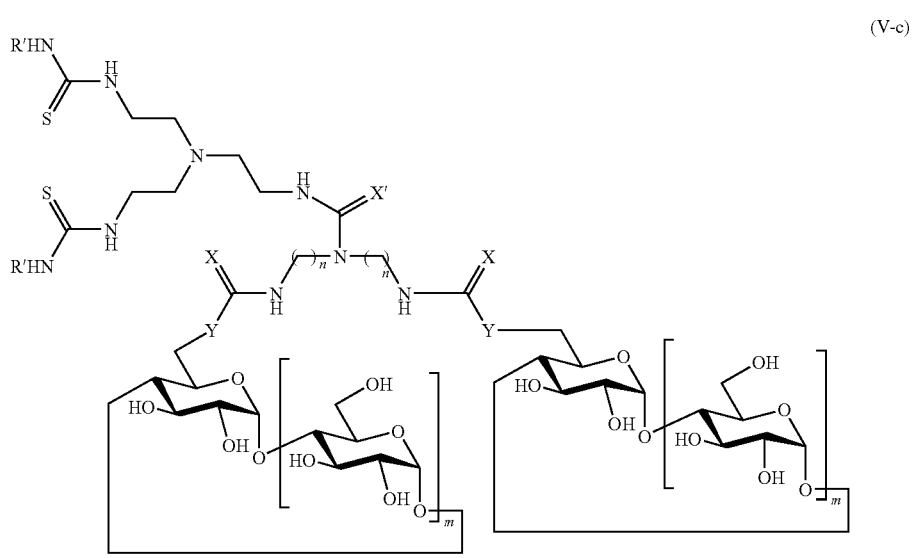

(V-c)

m, n, p, X, X', Y being as defined above, and R' having the definition given previously for R.

The present invention also relates to a compound as defined above, corresponding in particular to formula (I-f), (I-i) or (I-j), characterized in that R comprises a branching element derived from tris(2-aminoethyl)amine (TREN), said compound corresponding to one of the following formulae (V-a-a), (V-b-a) or (V-c-a):

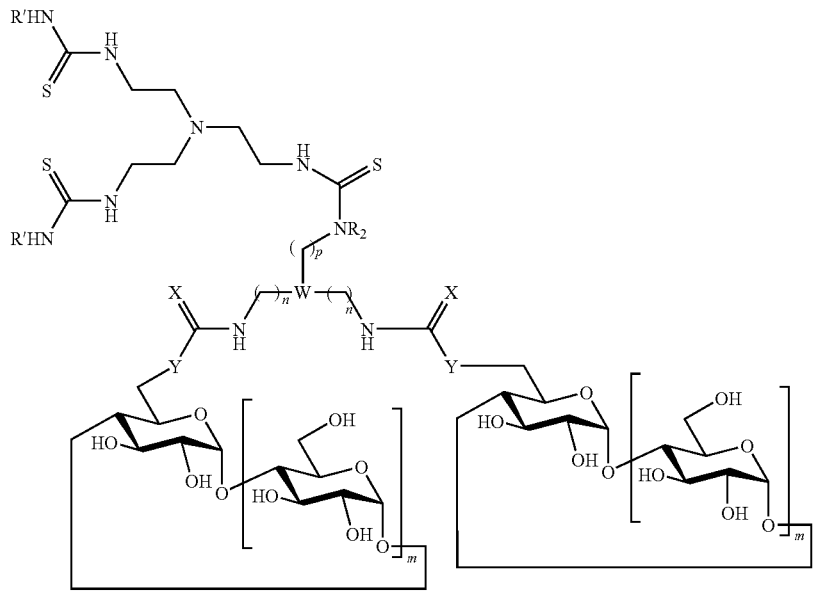
(V-a-a)
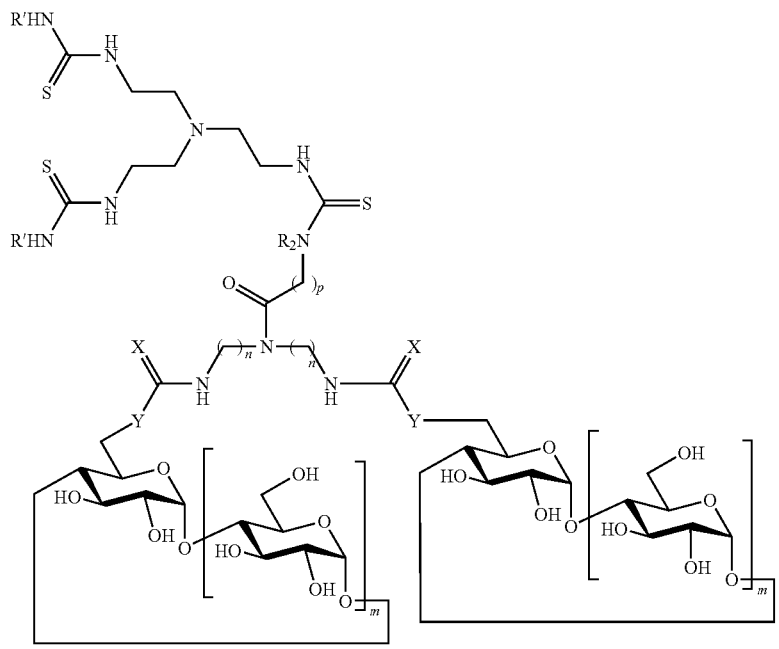
(V-b-a)

-continued

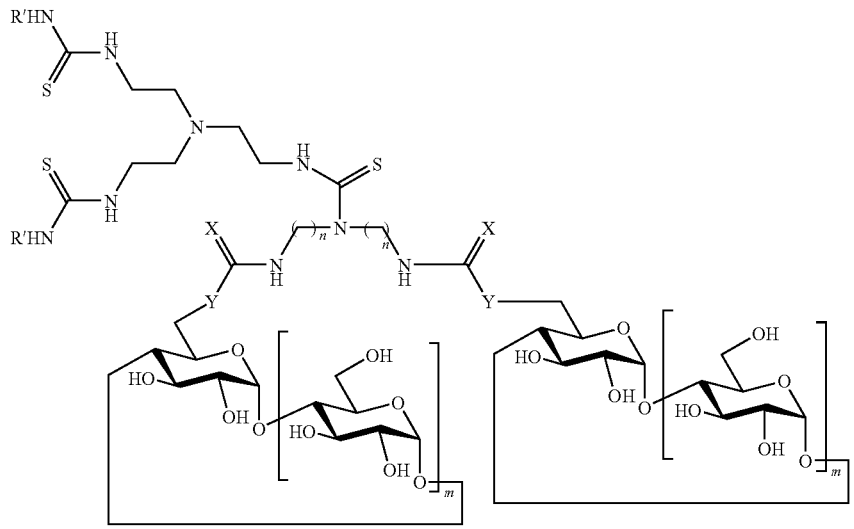

(V-c-a)

m, n, p, X, Y and R' being as defined above.

An advantageous compound according to the present invention is a compound as defined above, of formula (V-a), characterized in that Y represents NH, X and X' represent a sulphur atom, W represents a nitrogen atom, $R^2$ represents a hydrogen atom and in that n is equal to 2. Such a compound corresponds to the following formula:

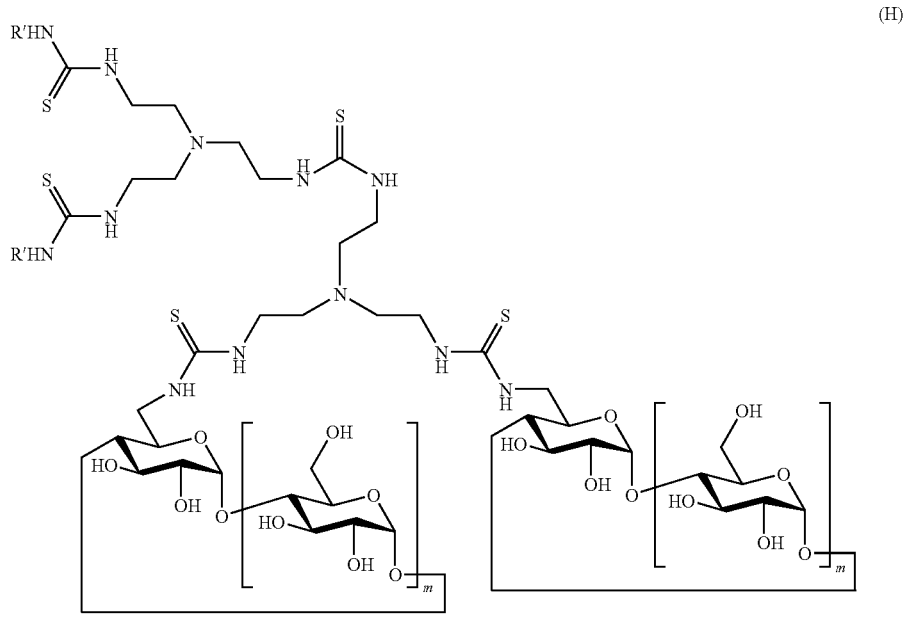

(H)

m and R' being as defined above.

The presence of two substituents R' in the compounds of formula (H) is particularly useful when R' represents a biological recognition element, and in particular when this recognition element is a glucide derivative, since in this case the affinity for the complementary biological receptors is improved due to the multivalent dendritic presentation of the ligand.

The present invention also relates to a compound as defined above, of formula (V-a), (V-b) or (V-c), characterized in that R' represents:

the α-D-mannopyranosyl group, of formula (III), or the β-lactosyl group of formula (III-a), or the tris(α-D-mannopyranosyloxymethyl)methyl group, of formula (IV), or the tris(β-lactyloxymethyl)methyl group, of formula (IV-a).

Thus, the present invention relates in particular to the compounds corresponding to one of the following formulae:
compound of formula (H) in which R' represents the α-D-mannopyranosyl group of formula (III):
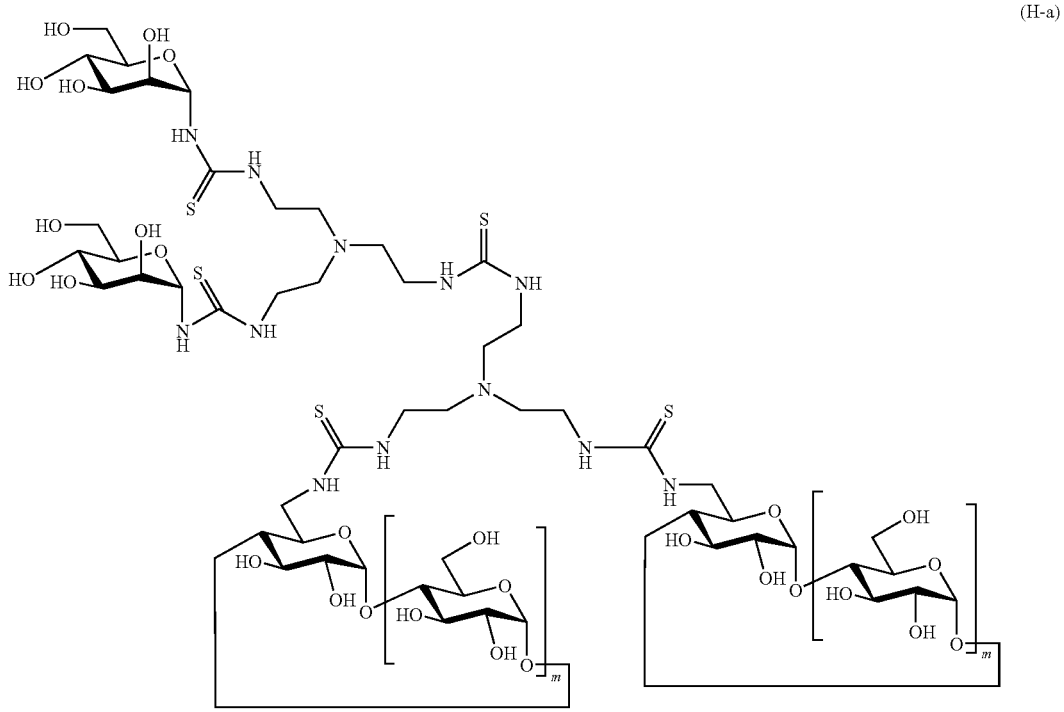
(H-a)
compound of formula (H) in which R' represents the β-lactosyl group of formula (III-a):
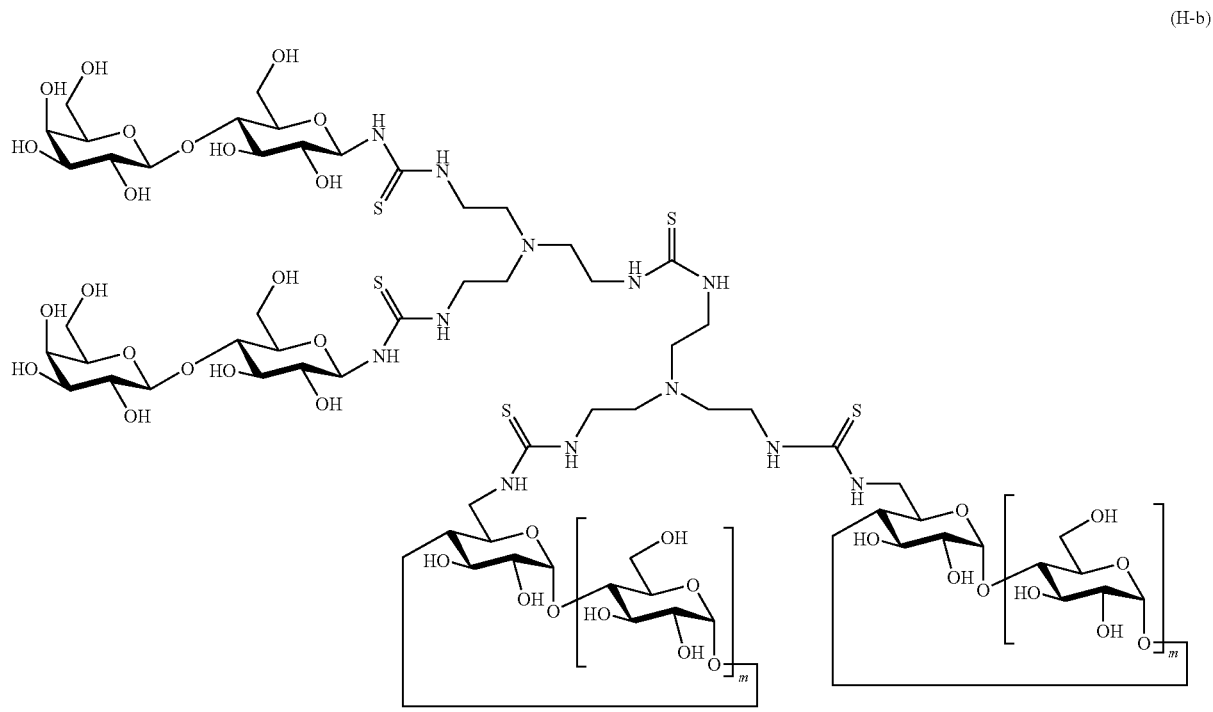
(H-b)

compound of formula (H) in which R' represents the tris (α-D-mannopyranosyloxymethyl)methyl group of formula (IV):
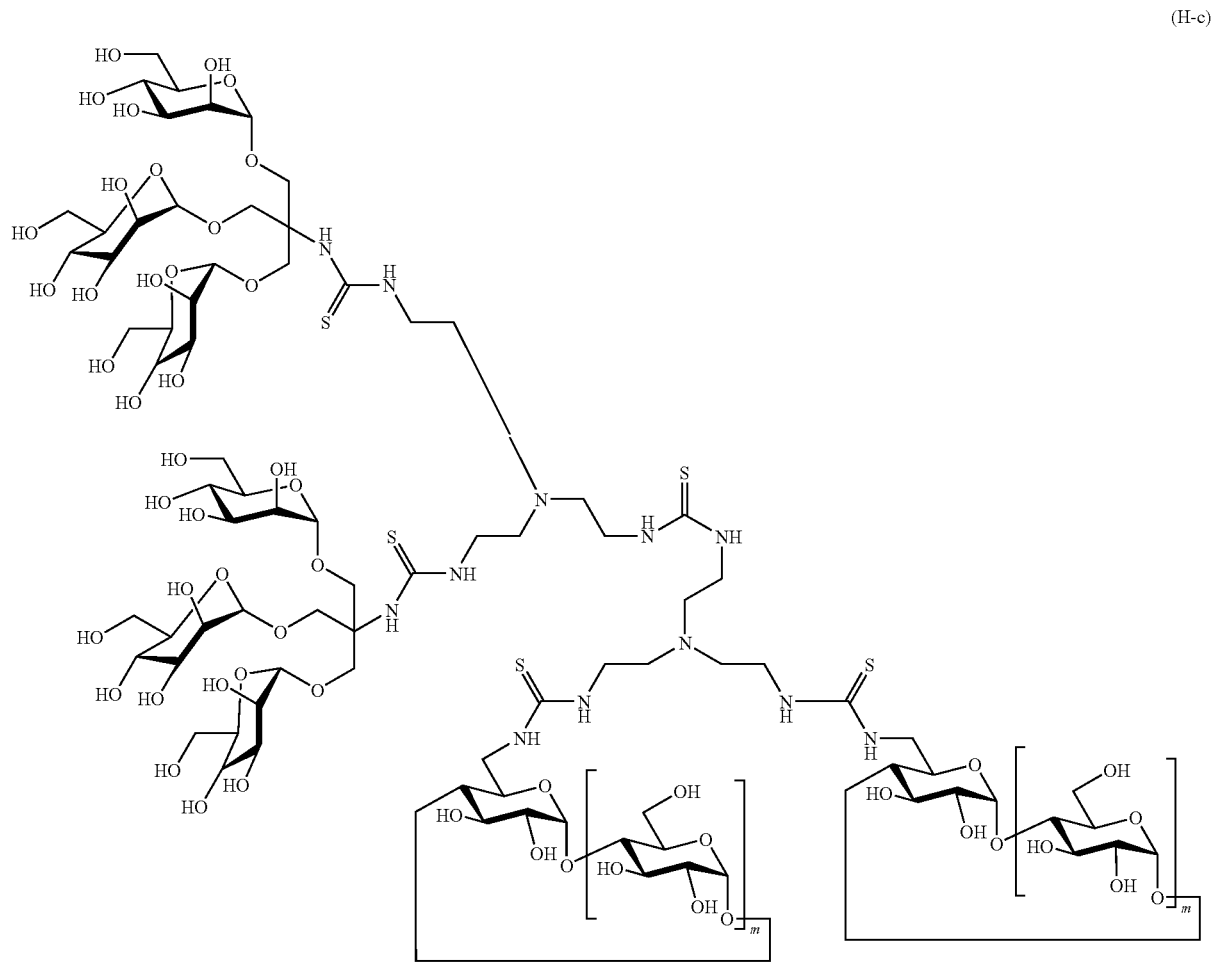
(H-c)
compound of formula (H) in which R' represent the tris(β-lactosyloxymethyl)methyl group, of formula (IV-a):
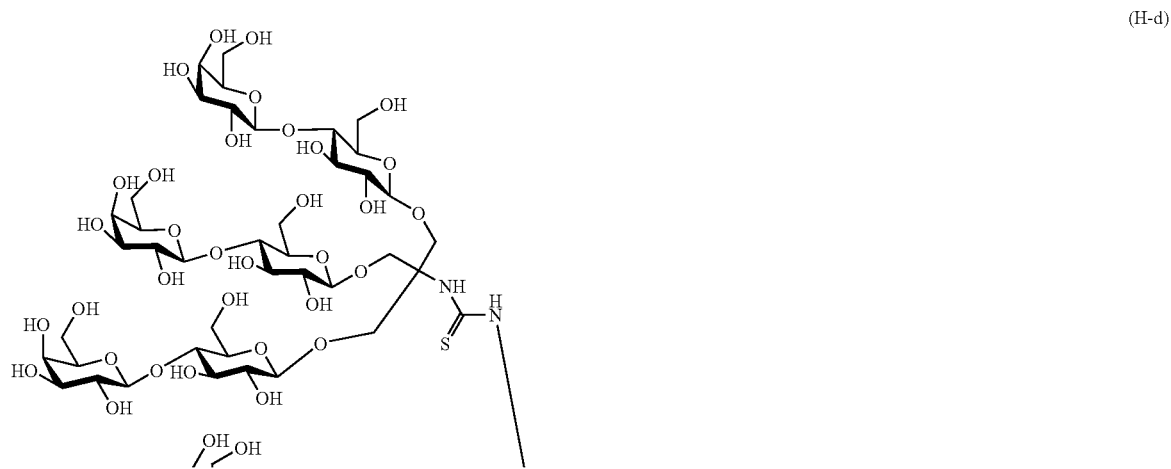
(H-d)

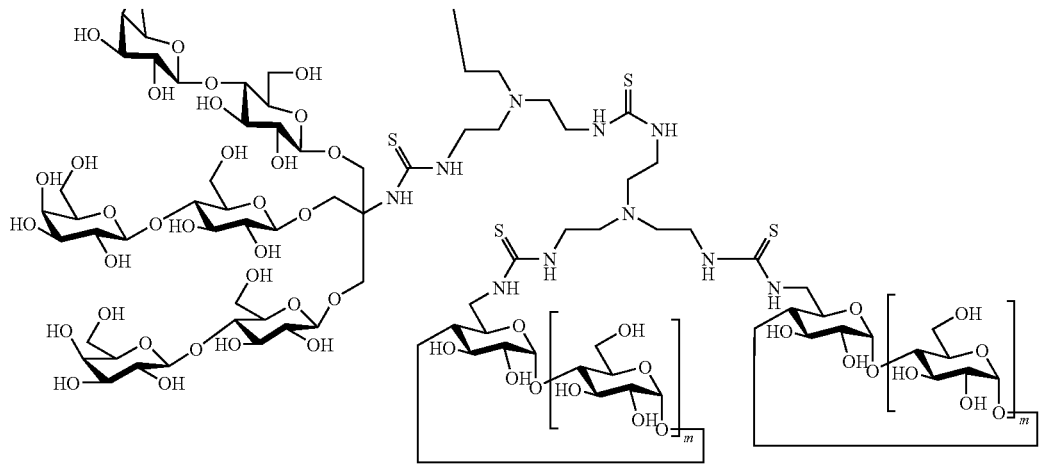

The present invention also relates to a compound as defined above, characterized in that m is equal to 6.

The use of cyclodextrin derivatives monosubstituted in primary alcohol position with a group carrying an amine functionality, as precursors for the preparation of the cyclodextrin dimers of the invention, has advantages in comparison with other previously described methods. In particular, the formation of two urea or thiourea type bonds by reaction with a dimerization element of diisocyanate or diisothiocyanate type has advantages from the point of view of operational simplicity, yields and purification of the final product which most often does not require chromatographic separation. Another useful feature of the present invention in comparison with other previously described methods is the use of dimerization elements possessing a protected amine functionality, which can be used for the incorporation of novel substituents on the cyclodextrin dimer derivative, such as a biorecognition element, in particular by formation of a novel urea or thiourea bond.

The present invention also relates to a method for preparing a compound as defined above, of formula (I), characterized in that it comprises the following stages:

the reaction of a compound selectively functionalized in primary alcohol position with an amine group, of the following formula (VII):

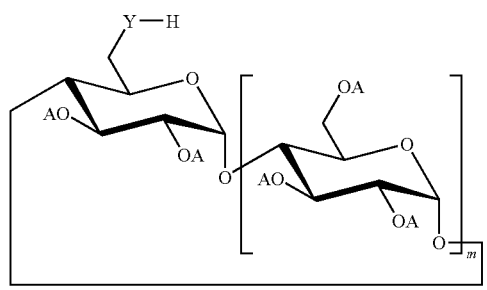

(VII)

m, A and Y being as defined above, and A preferably being a hydrogen atom, with a dimerization element of diisocyanate or diisothiocyanate type, in particular carrying a protected amine functionality in the form of a carbamate group or carrying a positively charged quaternary ammonium salt functionality, of the following forula (VIII):

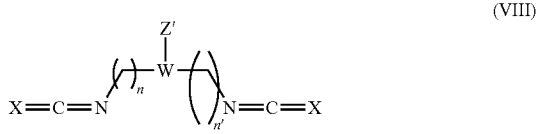

(VIII)

n and n' being as defined above, and preferably being equal,

W and X being as defined above,

Z' representing a group corresponding to one of the following formulae:

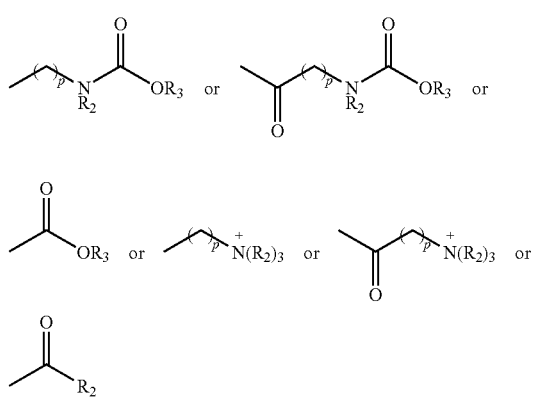

p, $R_2$ and $R_3$ being as defined above, in order to obtain a compound as defined above of formula (I), and corresponding to the following formula (IX):

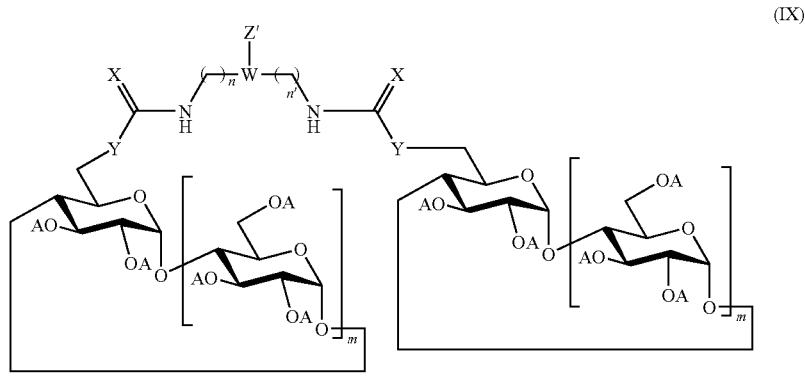

(IX)

and optionally the hydrolysis reaction of the

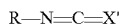

group as defined above, present in the compounds of the abovementioned formula (IX), in which Z' contains such group, in order to obtain a compound carrying a free amine functionality and corresponding to the following formula (X):

n, n,' A, X, Y, W and m being as defined previously, and Z" corresponding to the hydrolysate of the Z' group containing a —$COOR_3$ function, and representing a hydrogen atom or corresponding to one of the following formulae:

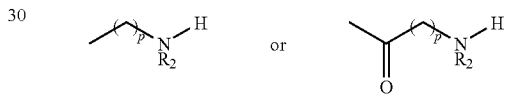

p and $R_2$ being as defined above, and optionally the reaction of a compound of formula (X) as obtained in the preceding stage, with an isocyanate or an isothiocyanate of the following formula (XI):

R—N═C═X'

R and X' being as defined above, in order to obtain a compound as defined above of formula (I), and corresponding to the following formula (XII):

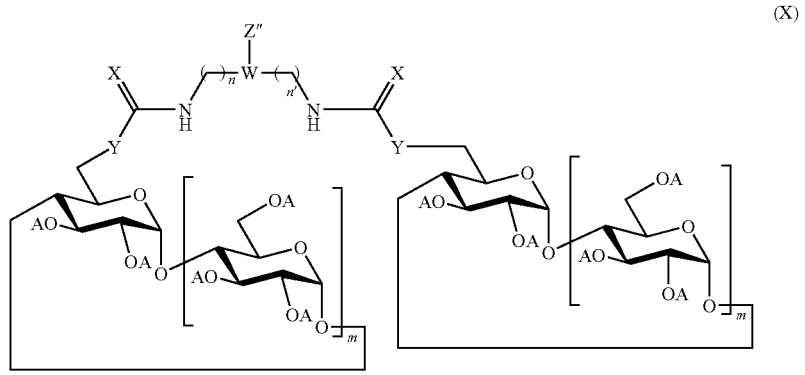

(X)

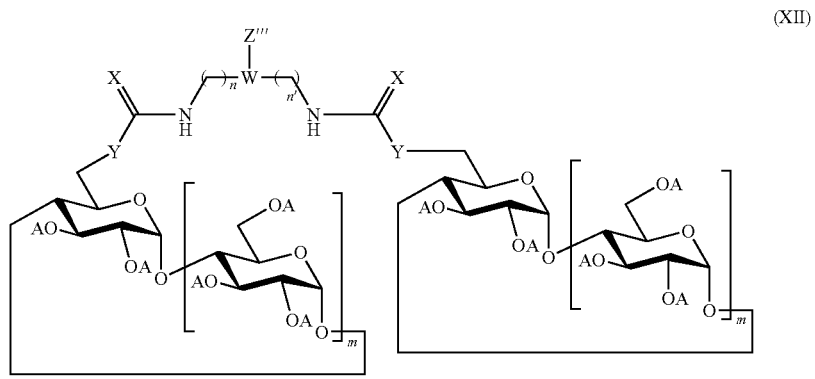
(XII)

n, n,' A, X, Y, W and m being as defined previously, and Z''' corresponding to one of the following formulae:

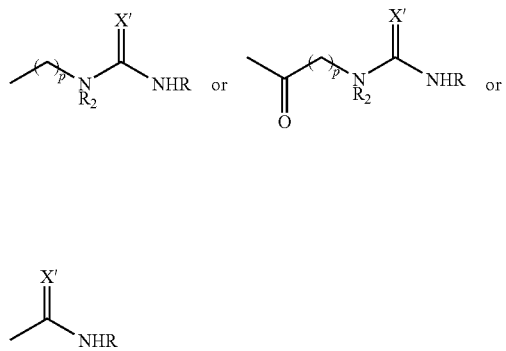

p, $R_2$, X' and R being as defined above.

The present invention also relates to a method for preparing a compound as defined above, of formula (I-a), characterized in that it comprises the following stages:

the reaction of a compound selectively functionalized in primary alcohol position with an amine group, of the following formula (VII-1):

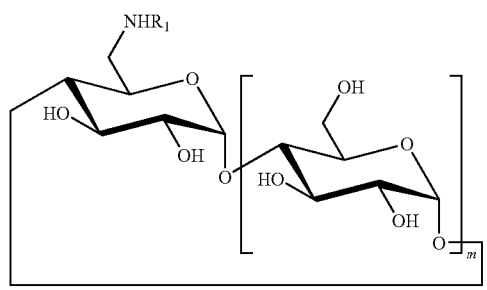

m being as defined above, with a dimerization element of diisocyanate or diisothiocyanate type, in particular carrying a protected amine functionality in the form of a carbamate group, of the following formulae (VIII-a), (VIII-b) or (VIII-c):

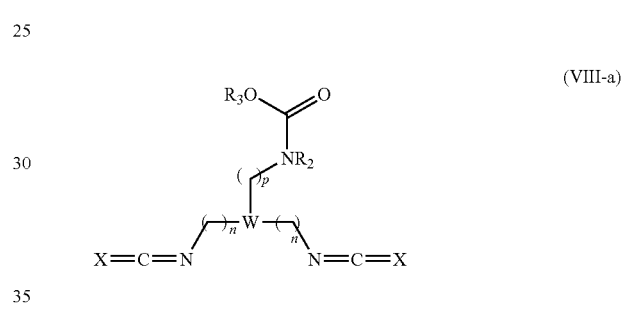

(VIII-a)

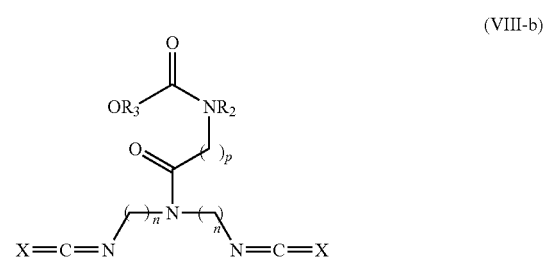

(VIII-b)

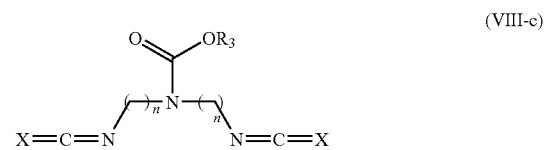

(VIII-c)

n, p, $R_2$, $R_3$, W and X being as defined above, in order to obtain a compound as defined above corresponding to the formulae (IX-1-a), (IX-1-b) or (IX-1-c) respectively:

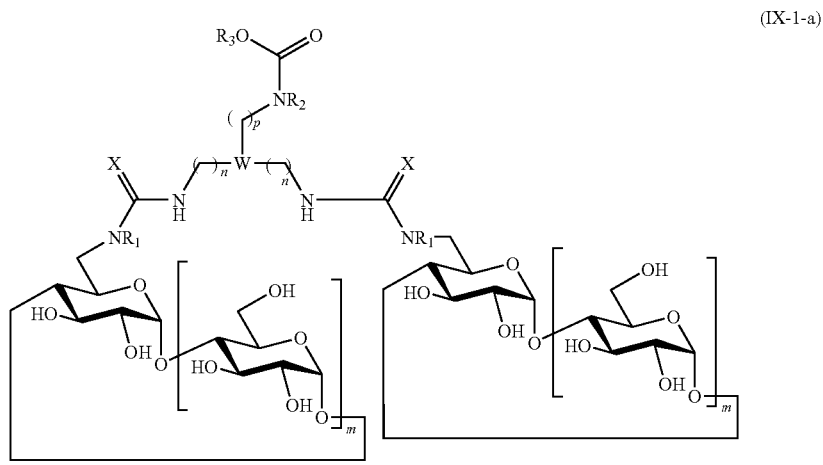
(IX-1-a)
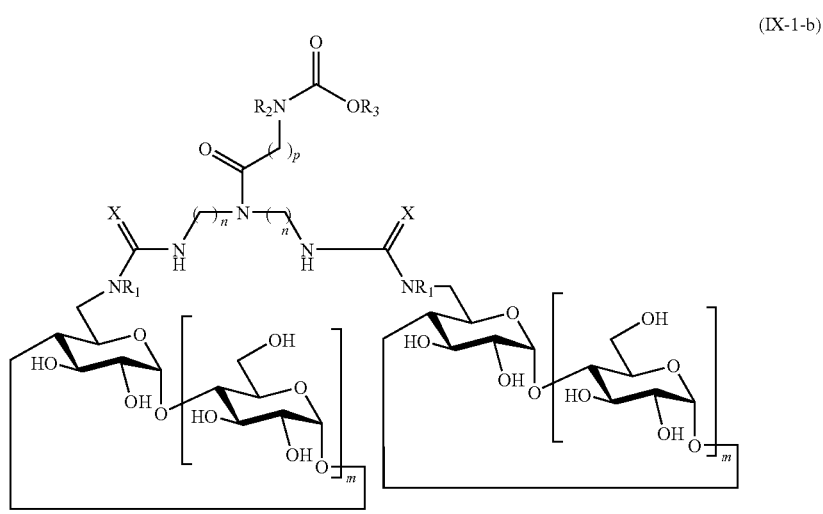
(IX-1-b)
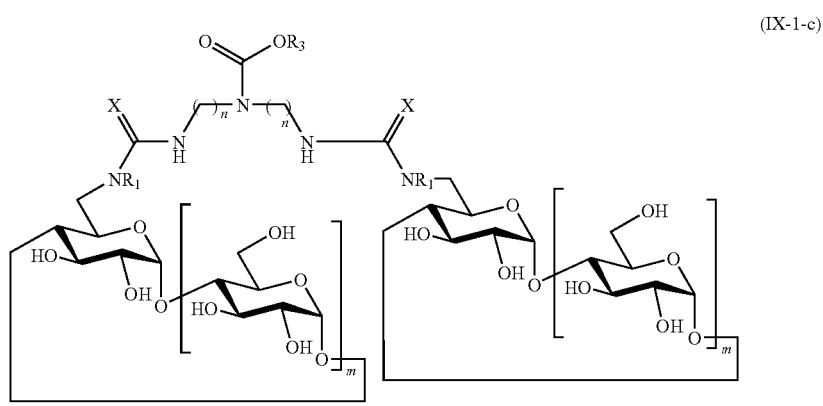
(IX-1-c)
and optionally the hydrolysis reaction of the
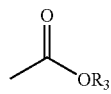
group as defined above, present in the compounds of the abovementioned formulae (IX-1-a), (IX-1-b) or (IX-1-c), in order to obtain a compound carrying a free amine functionality and corresponding to the following formulae (X-1-a), (X-1-b) or (X-1-c) respectively:

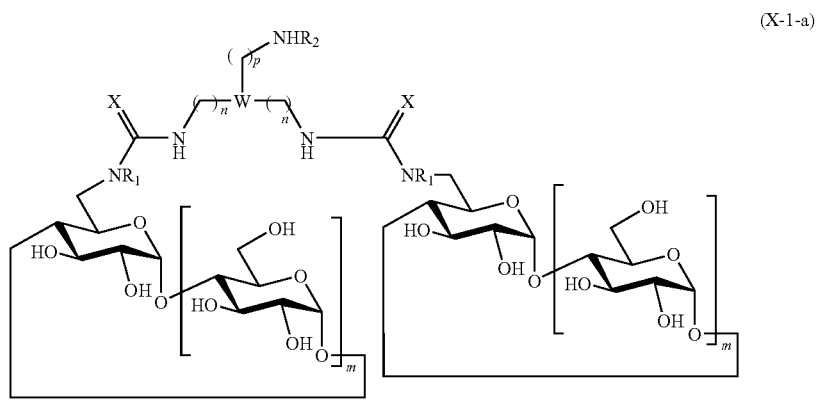
(X-1-a)
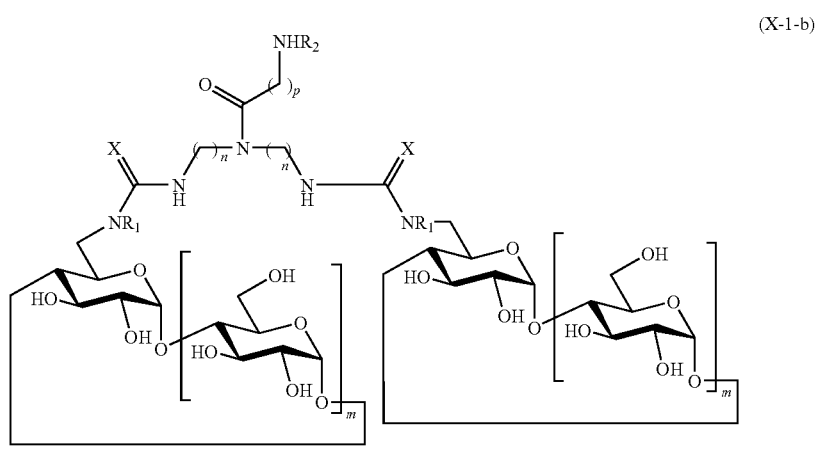
(X-1-b)
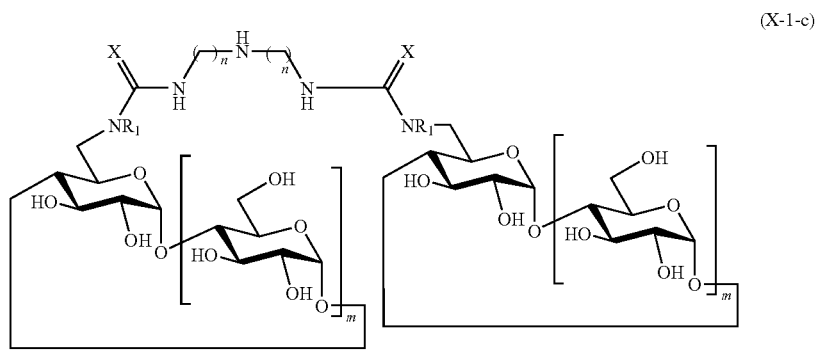
(X-1-c)
and optionally the reaction of a compound of formula (X-1-a), (X-1-b) or (X-1-c) as obtained in the preceding stage, with an isocyanate or an isothiocyanate of the following formula (XI):
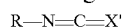
R and X' being as defined above,
in order to obtain a compound as defined above corresponding to formula (XII-1-a), (XII-1-b) or (XII-1-c) respectively:

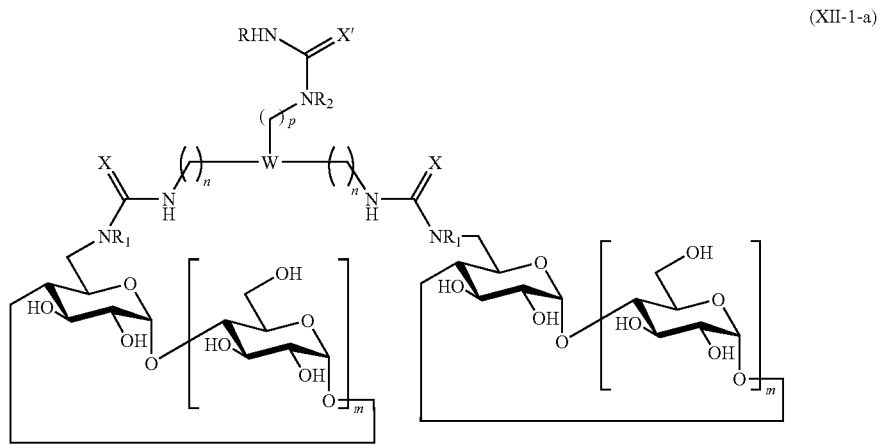
(XII-1-a)
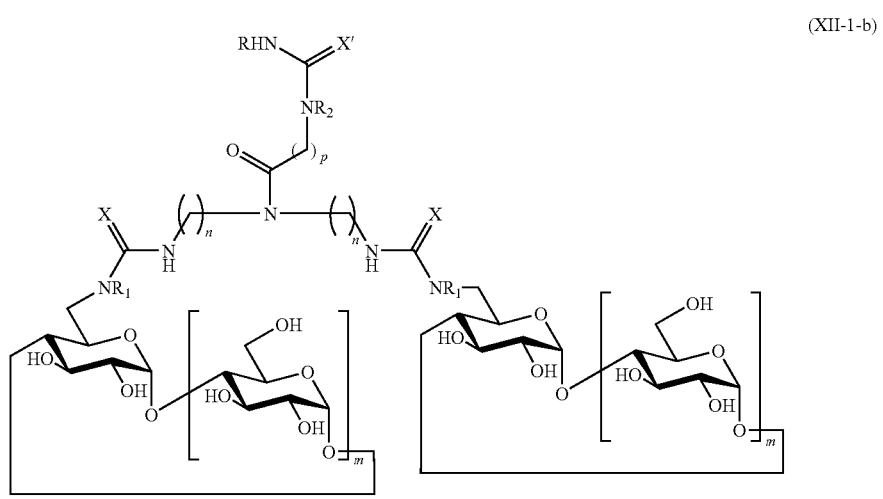
(XII-1-b)
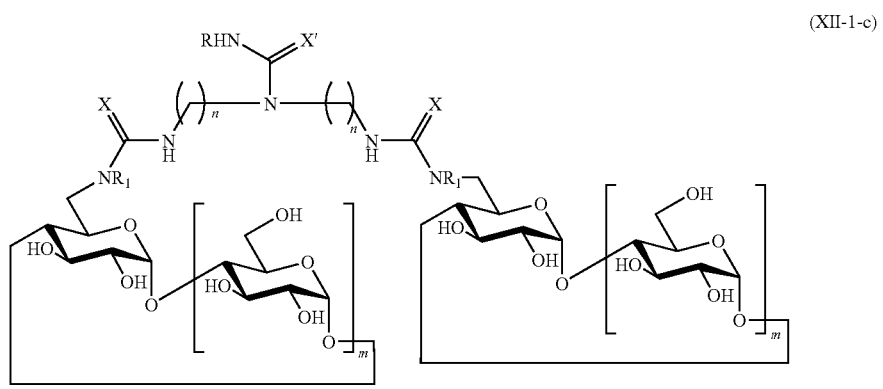
(XII-1-c)
The present invention also relates to a method for preparing a compound as defined above, of formula (I-b), characterized in that it comprises the following stages: the reaction of a compound selectively functionalized in primary alcohol position with an amine group, of the following formula (VII-2):

(VII-2)
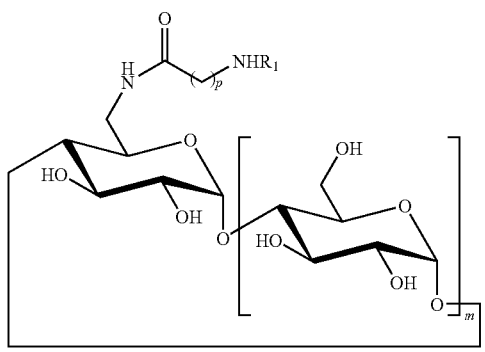
m, p and R₁ being as defined above,
with a dimerization element of diisocyanate or diisothiocyanate type, in particular carrying a protected amine functionality in the form of a carbamate group, of the abovementioned formulae (VII-a), (VIII-b) or (VIII-c),
in order to obtain a compound as defined above corresponding to the formulae (IX-2-a), (IX-2-b) or (IX-2-c) respectively:
(IX-2-a)
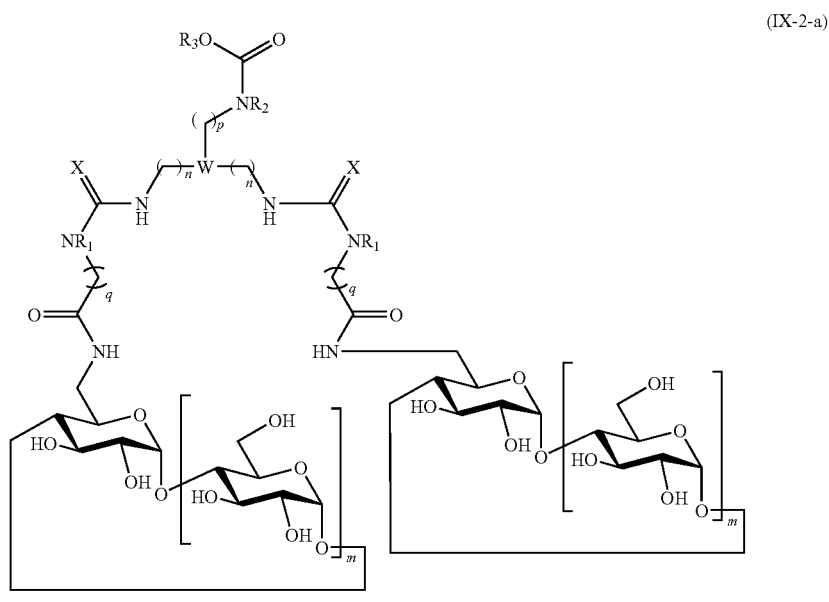
(IX-2-b)
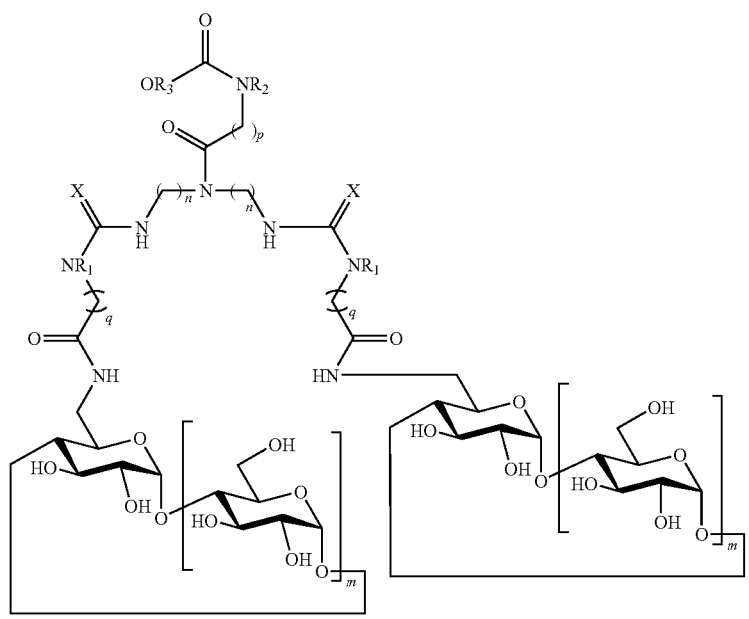

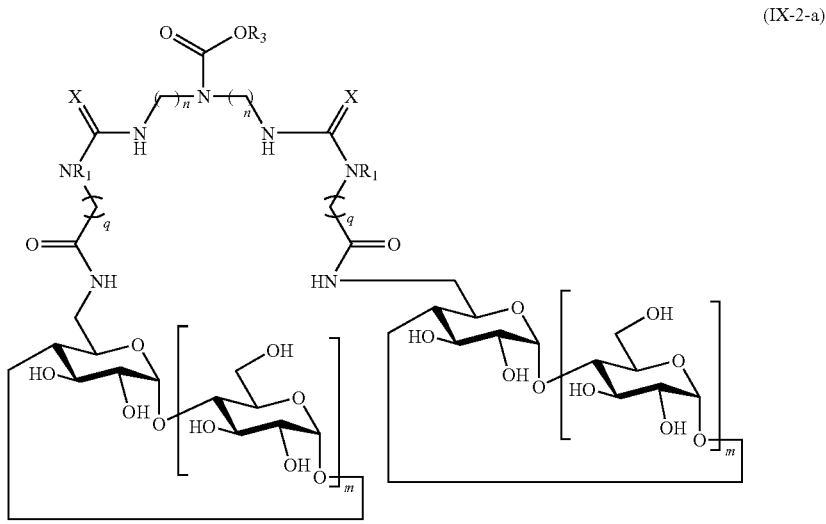
(IX-2-a)
and optionally the hydrolysis reaction of the
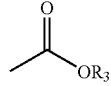
group as defined above, present in the compounds of the abovementioned formulae (IX-2-a), (IX-2-b) or (IX-2-c), in order to obtain a compound carrying a free amine functionality and corresponding to the following formulae (X-2-a), (X-2-b) or (X-2-c) respectively:
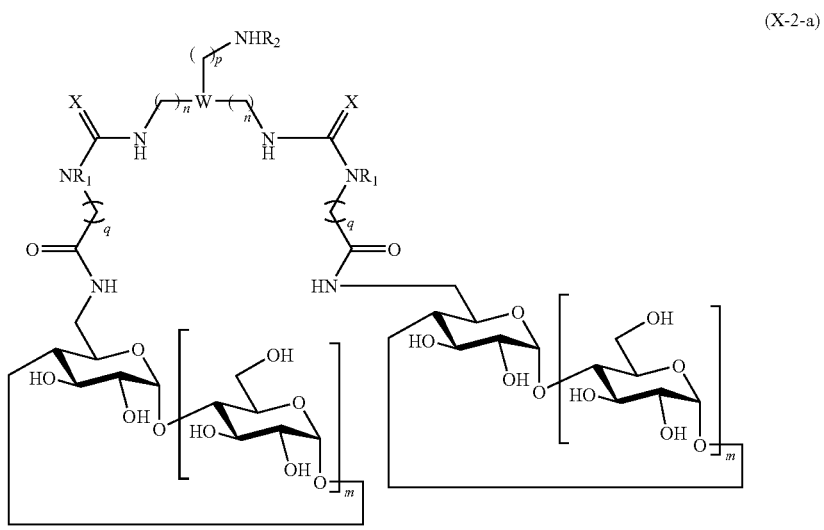
(X-2-a)

-continued
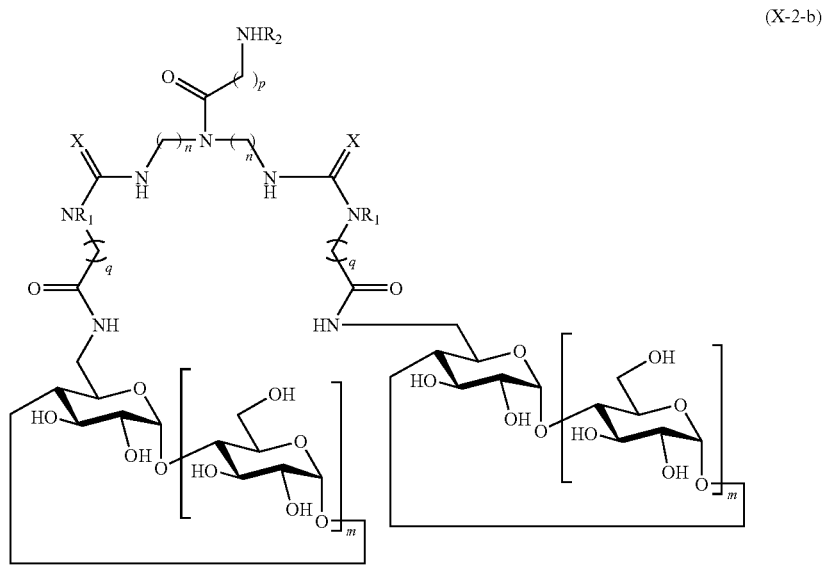
(X-2-b)
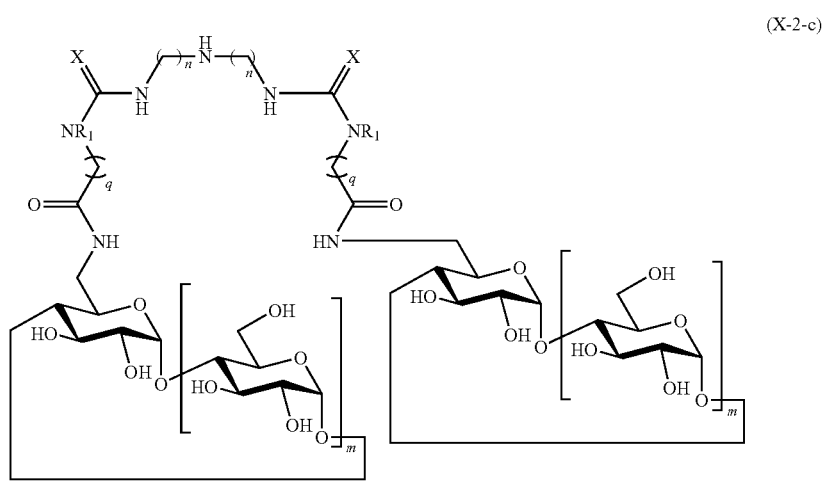
(X-2-c)
and optionally the reaction of a compound of formula (X-2-a), (X-2-b) or (X-2-c) as obtained in the preceding stage, with an isocyanate or an isothiocyanate of the following formula (XI):
R—N=C=X'
R and X' being as defined above,
in order to obtain a compound as defined above corresponding to the formulae (XII-2-a), (XII-2-b) or (XII-2-c) respectively:

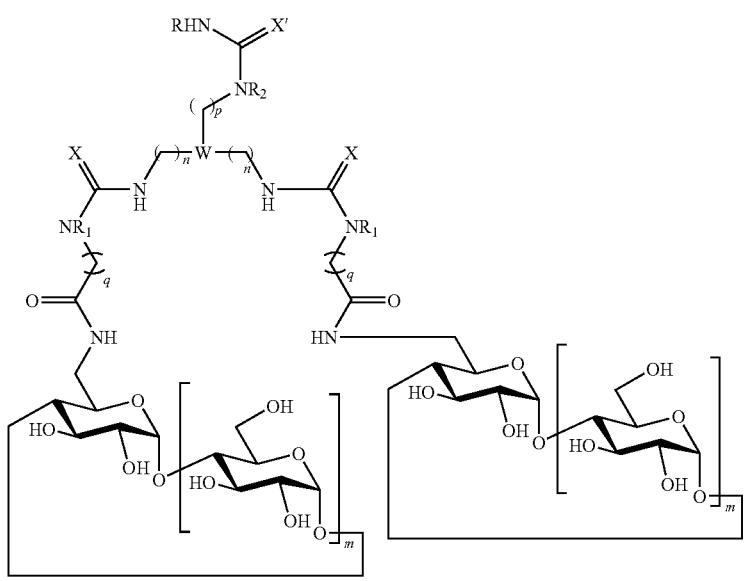
(XII-2-a)
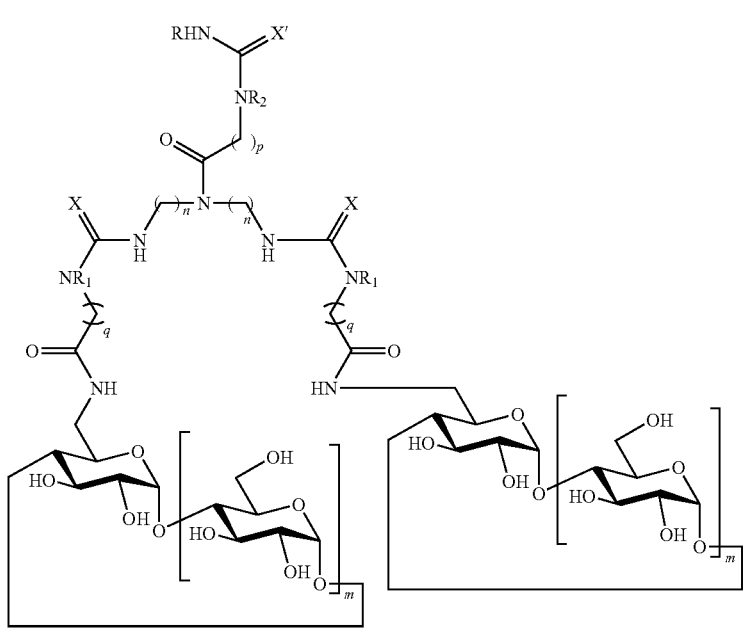
(XII-2-b)

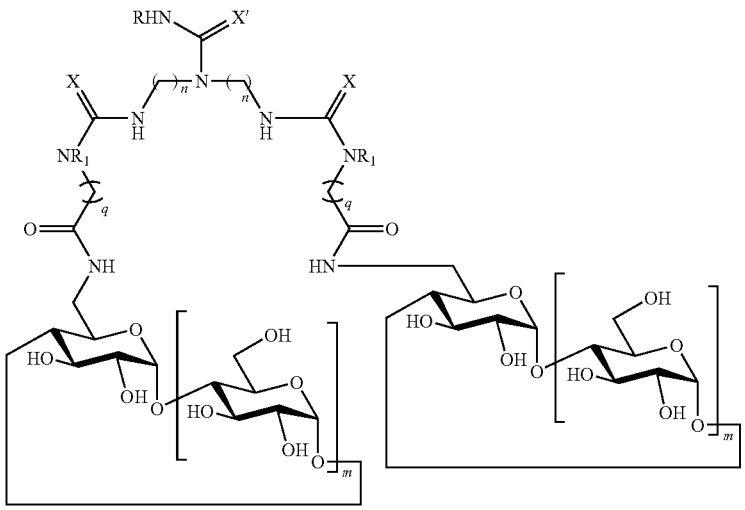

(XII-2-c)

The present invention also relates to a method for preparing a compound as defined above, of formula (I-c), characterized in that it comprises the following stages:

the reaction of a compound selectively functionalized in primary alcohol position with an amine group, of the following formula (VII-3):

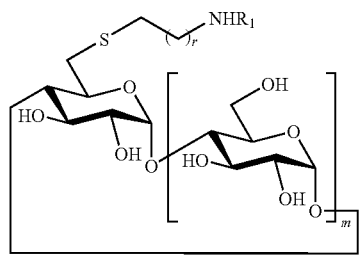

(VII-3)

$m$, $r$ and $R_1$ being as defined above, with a dimerization element of diisocyanate or diisothiocyanate type, in particular carrying a protected amine functionality in the form of a carbamate group, of the abovementioned formulae (VIII-a), (VIII-b) or (VIII-c), in order to obtain a compound as defined above corresponding to the formulae (IX-3-a), (IX-3-b) or (IX-3-c) respectively:

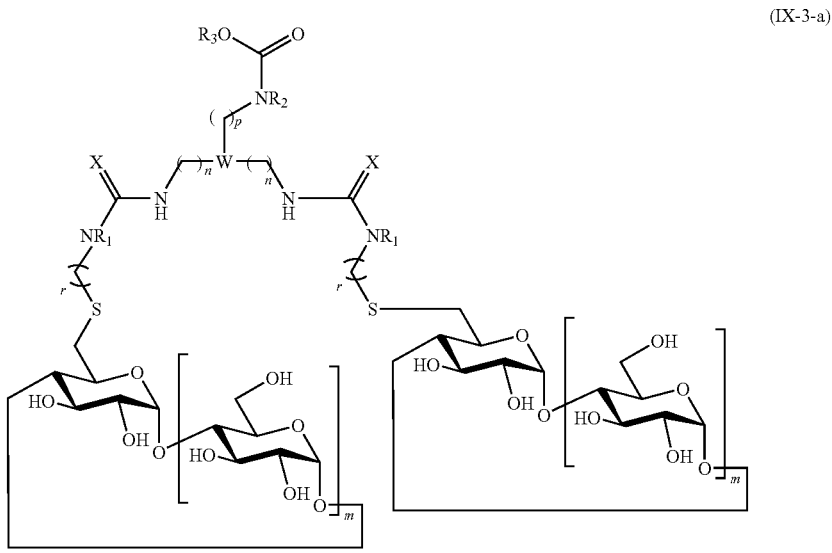

(IX-3-a)

-continued
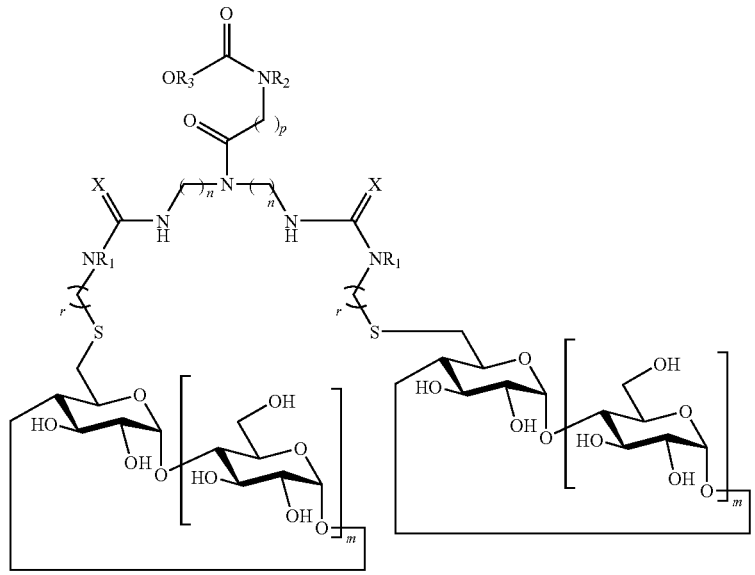
(IX-3-b)
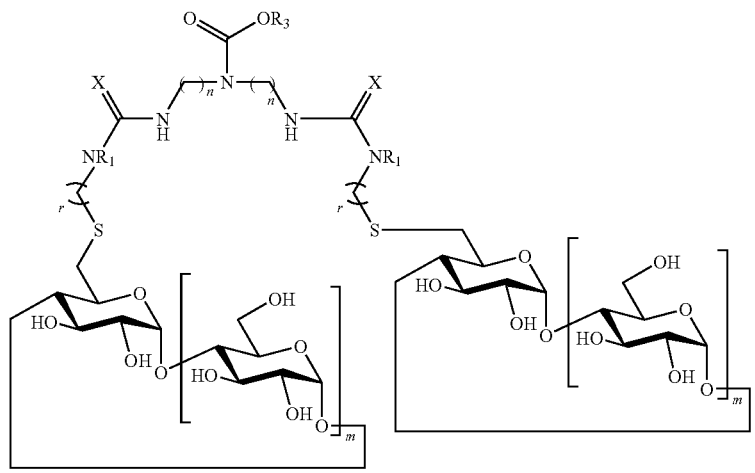
(IX-3-c)
and optionally the hydrolysis reaction of the
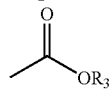
group as defined above, present in the compounds of the abovementioned formulae (IX-3-a), (IX-3-b) or (IX-3-c), in order to obtain a compound carrying a free amine functionality and corresponding to the following formulae (X-3-a), (X-3-b) or (X-3-c) respectively:

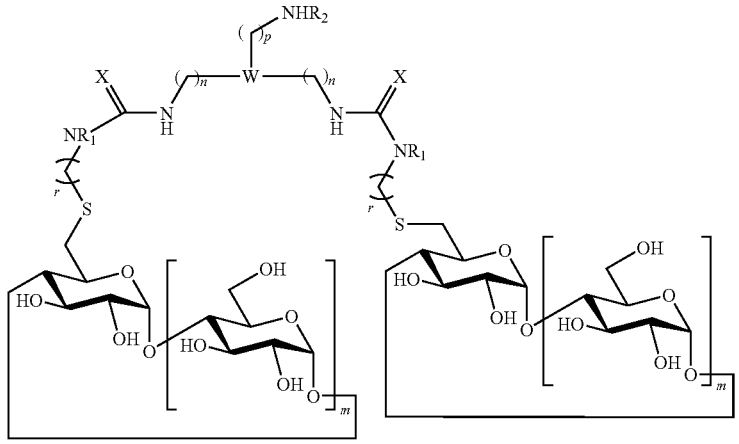
(X-3-a)
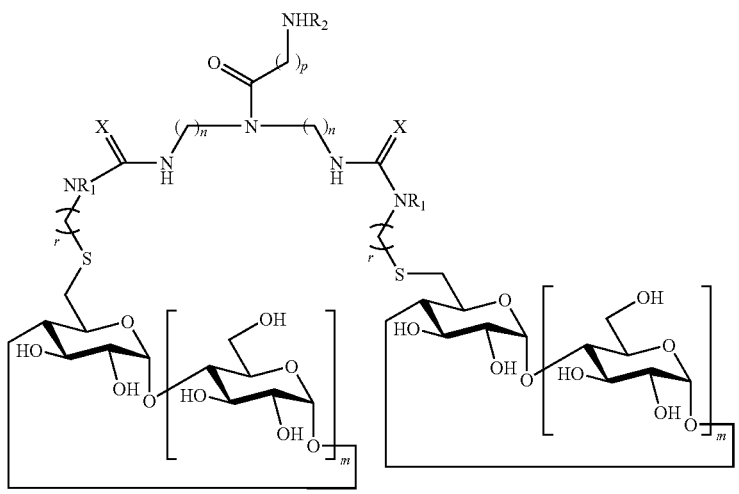
(X-3-b)
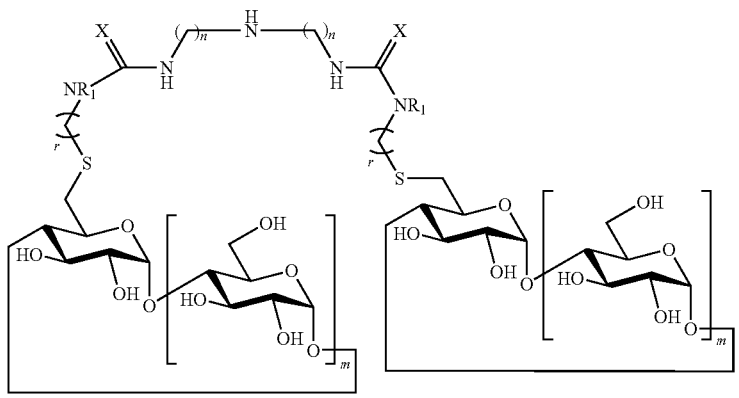
(X-3-c)
and optionally the reaction of a compound of formula (X-3-a), (X-3-b) or (X-3-c) as obtained in the preceding stage, with an isocyanate or an isothiocyanate of the following formula (XI):
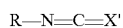
R and X' being as defined above,
in order to obtain a compound as defined above corresponding to the formulae (XII-3-a), (XII-3-b) or (XII-3-c) respectively:

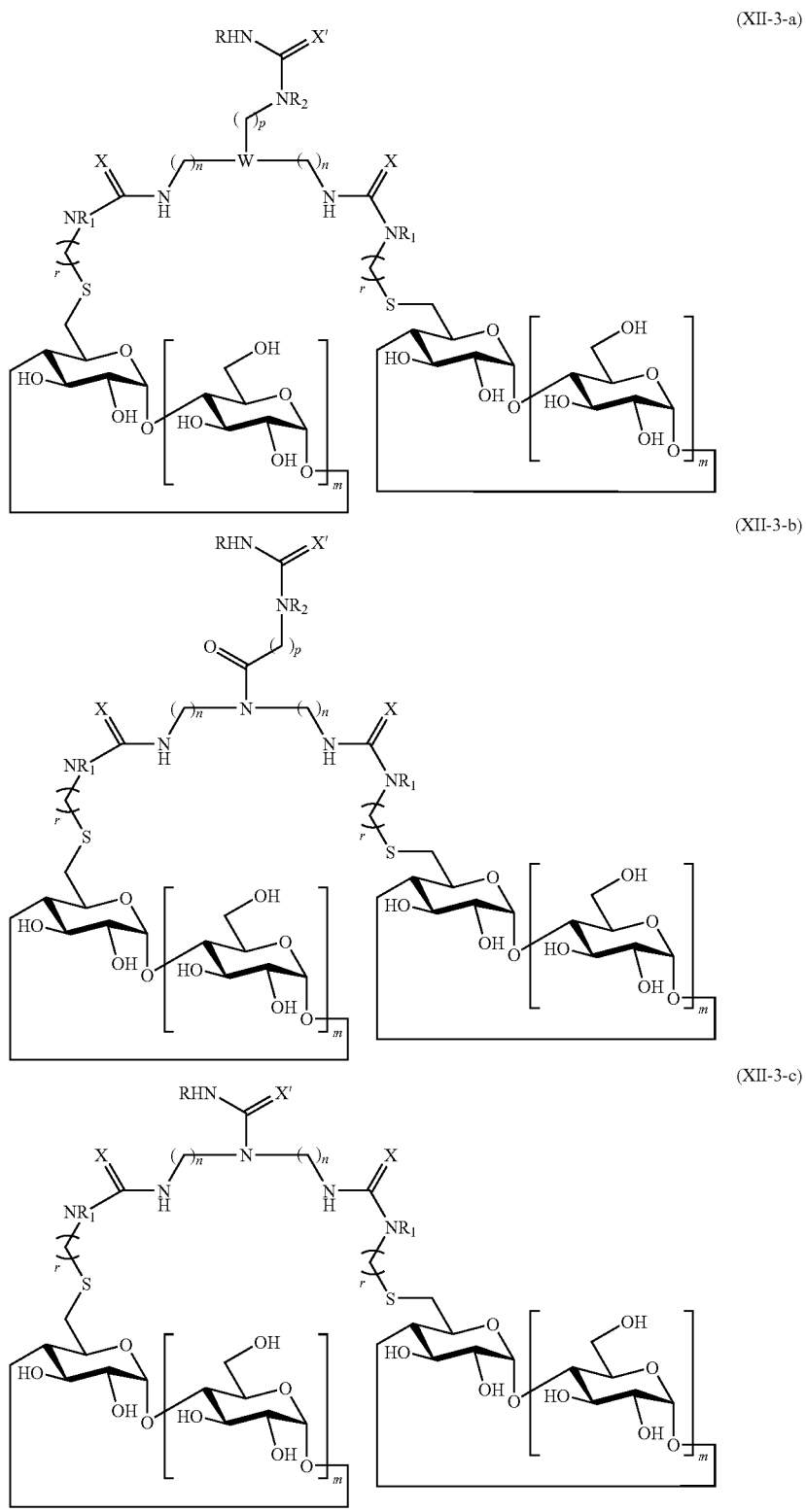

(XII-3-a)

(XII-3-b)

(XII-3-c)

It is to be noted moreover that the method of synthesis developed is very flexible as regards the nature of the spacer arm between the primary alcohol positions of the two cyclodextrin sub-units, in particular its length, which makes it possible to optimize the geometry of the cyclodextrin dimer receptor for the effective complexation of a determined guest molecule. This spacer arm can be constructed in particular from the $6^I$-amino-$6^I$-deoxy derivative of the corresponding cyclodextrin, from a derivative incorporating an amide substituent of 6$^I$-(ω-aminoalkanamido)-6$^I$-deoxy type, or also from a derivative incorporating a cysteaminyl substituent or, more generally, from a substituent derived from an co-aminoalkanethiol. These three families of precursors are simply accessible from the cyclodextrin derivatives monofunctionalized in primary alcohol position of 6$^I$-deoxy-6$^I$-p-toluenesulphonyl type, which can be prepared in one stage from commercial cyclodextrins. In this regard the method described by J. Defaye et al. in the international Patent Application WO 99/61483 or the methods described in the article by L. Jicsinszky et al. in *Comprehensive Supramolecular Chemistry*, Vol. 3 (Editors J. Szejtli and T. Osa), Pergamon, Oxford, 1996, pp. 57-198 can be followed. The nucleophilic substitution of the p-toluenesulphonate group either by the azide anion ($N_3^-$), followed by a reduction reaction, or also by a primary amine leads to the cyclodextrin derivatives of 6$^I$-amino-6$^I$-deoxy type. By way of example, for these conversions the method described by I. Baussanne et al. in the document *Chem. Commun,* 2000, pp. 1489-1490 or the methods described in the article by L. Jicsinszky et al. in *Comprehensive Supramolecular Chemistry*, Vol. 3 (Editors J. Szejtli and T. Osa), Pergamon, Oxford, 1996, pp. 57-198 can be used, or also for the alkylated cyclodextrin derivatives the method described by Jicsinszinsky et al. in *Carbohydr. Polym.* 2001, 45, 139-145. The selective acylation of the amine group in the 6$^I$-amino-6$^I$-deoxycyclodextrins by derivatives of ω-aminoalkanecarboxylic acids, the terminal amine group being protected in the form of a carbamate, and the release of the amine group at the end of the chain in the resulting product leads to the derivatives of 6$^I$-(ω-aminoalkanamido)-6$^I$-deoxycyclodextrin type. Finally, the cysteaminyl-type derivatives can be obtained by reaction of the corresponding 6$^I$-deoxy-6$^I$-p-toluenesulphonylcyclodextrin or of a derivative of 6$^I$-deoxy-6$^I$-halogenocyclodextrin type with cysteamine or, generally, with a ω-aminoalkanethiol. Optionally, the amine group in any one of the abovementioned precursors can carry an alkyl substituent such as a methyl, ethyl, propyl or butyl group.

The amine group in the cyclodextrin derivatives used as precursors of the cyclodextrin dimers of the invention, makes it possible to combine two cyclodextrin sub-units with a dimerization element possessing two complementary groups, in particular two isocyanate or isothiocyanate groups. The coupling reaction leads to a cyclodextrin dimer derivative with two urea or thiourea bonds, which are very stable and which give rise to well-defined structures. When the amine group in the precursor cyclodextrin derivative is an $NH_2$ primary amine, the ureas or thioureas obtained are N,N'-disubstituted, whereas when it is an $NHR_1$-type secondary amine group, $R_1$ representing an alkyl substituent, such as methyl, ethyl, propyl or butyl, the ureas or thioureas obtained are N,N',N''-trisubstituted.

The first and the last stage of the abovementioned method consist of coupling reactions between an amine derivative and a derivative of an isocyanate or isothiocyanate-type heterocummulene, carried out in a water-acetone mixture (2:1 to 1:2) at pH 8-9 (sodium acid carbonate at ambient temperature for 2-24 hours). The yield is comprised between approximately 60 and 90% for the first stage and between 50 and 85% for the last stage.

The second stage corresponds to the release of a protected amine group in the form of carbamate. Preferably, this carbamate group is a tert-butyloxycarbonyl-type derivative, and its deprotection is carried out by acid hydrolysis with a trifluoroacetic acid-water mixture 1:1 at ambient temperature or at 40° C. for 2 hours, the yield being quantitative.

The ureido- and thioureido-cyclodextrin dimer-type derivatives of the invention corresponding to formula (I) in which Y represents the $NR_1$ group (compounds of formula (I-a)), can be prepared by a method which consists of reacting a 6$^I$-amino-6$^I$-deoxycyclodextrin derivative with a diisocyanate or a diisothiocyanate of the abovementioned formula (VIII-a), (VIII-b) or (VIII-c). This reaction can be carried out in an organic solvent such as pyridine or also in a mixture of water with a miscible organic solvent such as acetone. For the preparation of the precursor cyclodextrin derivative selectively monofunctionalized in primary alcohol position, the method described by I. Baussanne et al. in the document *Chem. Commun,* 2000, pp. 1489-1490 or the methods described in the article by L. Jicsinszky et al. in *Comprehensive Supramolecular Chemistry*, Vol. 3 (Editors J. Szejtli and T. Osa), Pergamon, Oxford, 1996, pp. 57-198 can be used.

The ureido- and thioureido-cyclodextrin dimer-type derivatives of the invention corresponding to formula (I) in which Y represents the —NH—CO—$(CH_2)_q$—$NR_1$ group (compounds of formula (I-b)), can be prepared by a method which consists of reacting a 6$^I$-(ω-aminoalkyl-6$^I$-deoxycyclodextrin derivative with a diisocyanate or a diisothiocyanate of the abovementioned formula (VIII-a), (VIII-b) or (VIII-c). This reaction can be carried out in an organic solvent such as pyridine or also in a mixture of water with an organic solvent such as acetone. The precursor cyclodextrin derivative selectively monofunctionalized in primary alcohol position can be prepared from the corresponding 6$^I$-amino-6$^I$-deoxycyclodextrin derivative by selective N-acylation with a derivative of ω-(N-tert-butyloxycarbonyl-amino)alkylcarboxylic acid, such as N-tert-butyloxycarbonylglycine (Boc-glycine), followed by acid hydrolysis of the N-Boc group by trifluoroacetic acid-water 1:1.

The ureidocysteaminyl- and thioureidocysteaminyl-cyclodextrin dimer-type derivatives of the invention corresponding to formula (I) in which Y represents the —S—$(CH_2)_r$—$NR_1$ group (compounds of formula (I-c)), can be prepared by a method which consists of reacting a derivative of 6$^I$-S-(ω-aminoalkyl)-6$^I$-deoxycyclodextrin with a diisocyanate or a diisothiocyanate of the abovementioned formula (VIII-a), (VIII-b) or (VIII-c). This reaction can be carried out in an organic solvent such as pyridine or also in a mixture of water with an organic solvent such as acetone.

The diisocyanate or diisothiocyanate of the abovementioned formula (VIII-a), (VIII-b) or (VIII-c) can be obtained from a precursor triamine derivative in which one of the amine groups is selectively protected in the form of a carbamate group, preferably the Boc group, by isocyanation or isothiocyanation of the two remaining free amine groups.

The invention also relates to the ureido-, thioureido-, ureidocysteaminyl- and thioureidocysteaminyl-cyclodextrins dimer-type derivatives corresponding to formula (I) in which Z represents a substituent comprising a ureido or thioureido-type group. The method of the invention consists of reacting a cyclodextrin dimer derivative carrying an amine group corresponding to one of the following abovementioned formulae (X-1-a), (X-1-b) or (X-1c), (X-2-a), (X-2-b) or (X-2-c), or (X-3-a), (X-3-b) or (X-3-c), obtained according to the method indicated above, with an isocyanate or isothiocyanate of formula R—NCX' in which R and X' have the meaning given above. This reaction can be carried out in an organic solvent such as pyridine or also in a mixture of water with an organic solvent such as acetone.

When R is a group derived from a monosaccharide or from an oligosaccharide, the isocyanate of formula R—NCO can be prepared by reaction of a phosgene derivative, such as triphosgene, on an aminodeoxyglycose or a glycosylamine or by reaction of a glycosylisocyanate with an oxidation agent. In order to do this, the methods described in the article by R. Richter and H. Ulrich in "The Chemistry of Cyanates and Their Thio Derivatives", Part 2, S. Patai (Ed.), Wiley, Chichester, 1977, pp. 619-818 or the method described by Y. Ichikawa et al. in Synlett, 2000, 1253-1256 can be followed. When R is a group derived from a monosaccharide or from an oligosaccharide, the isothiocyanate of formula R—NCS can be prepared by reaction of the thiophosgene on an aminodeoxyglycose or a glycosylamine. For this reaction the methods described by J. M. Garcia Fernández and C. Ortiz Mellet in *Adv. Carbohydr. Chem. Biochem.* 1999, 55, pp. 35-135 can be followed.

When R comprises a branched multiplication element derived from tris(2-hydroxymethyl)methylamine (TRIS), the corresponding isocyanate or isothiocyanate can be prepared by reaction of a phosgene or thiophosgene derivative on the amine derivative carrying glucide substituents on the primary alcohol positions, as described in the document *Chem. Commun.*, 2000, pp. 1489-1490. The precursor aminated trivalent glycodendron can be obtained by glycosidation reaction of a TRIS derivative with the suitably protected amine function in the form of a carbobenzoxy derivative, as described by P. R. Ashton et al. in *J. Org. Chem.* 1998, 63, pp. 3429-3437.

When R comprises a branched multiplication element derived from pentaerythritol, the glycodendrons suitably functionalized with an isothiocyanate group can be prepared from commercial pentaerythritol by a sequence of reactions which involves:

(i) selective triallylation by treatment with allyl bromide, which leaves a single free hydroxyl group;

(ii) the radical addition of a 1-thiosugar to the double bond of the allyl groups; this reaction can be carried out, either by activation by ultraviolet light, or in the presence of a free radical initiator such as azobis(isobutyronitrile) or p-nitroperbenzoic acid. By way of example, the reaction conditions described by D. A. Fulton and J. F. Stoddart in *Org. Lett.* 2000, 2, pp. 1113-1116 or by X.-B. Meng et al. in *Carbohydr. Res.* 2002, 337, pp. 977-981 can be adapted. This reaction allows, in particular, the sequential addition of the different glucide branchings. It is thus possible to arrive at both the homogeneous and heterogeneous glycodendrons in which the glucide substituents correspond to the structures mentioned above. This approach also allows the incorporation in the structure of a substituent other than a glucide derivative, in particular a fluorescent-type probe such as a fluorescein derivative. The precursor 1-thiosugars can be prepared, either from the corresponding glycosyl halides by reaction with thiourea followed by hydrolysis of the resulting isothiouronium salt, or from glycals by radical addition of thioacetic acid to the double bond. For these reactions the methods described in the articles published by J. Defaye and J. Gelas in *Studies in Natural Products Chemistry*, Vol. 8 (Editor Atta.ur Rahman), Elsevier, Amsterdam, 1991, pp. 315-357 and by H. Driguez in *Top. Curr. Chem.*, 1997, 187, pp. 85-116 can be followed.

(iii) the conversion of the remaining primary alcohol group to an isothiocyanate group. This conversion can be carried out for example by conversion of the hydroxyl group to a good parting group such as p-toluenesulphonate or trifluoromethanesulphonate, followed by nucleophilic displacement by the azide anion and isocyanation or isothiocyanation of the resulting azide by reaction with triphenylphosphine and carbon dioxide or disulphide. For this conversion, the method described in the document *Chem. Commun.*, 2000, pp. 1489-1490 can be followed.

When R comprises a branched multiplication element derived from tris(2-aminoethyl)amine (TREN), the glycodendrons suitably functionalized with an isothiocyanate group can be prepared from commercial bis(2-aminoethyl)amine by a sequence of reactions which involves:

(i) the selective protection of the two primary amine groups in the form of tert-butyloxycarbonyl derivatives, by reaction with 2-(tert-butyloxycarbonyloximino)-2-phenylacetonitrile (Boc-ON) in tetrahydrofuran (THF); this reaction can be carried out according to the method described in *Synthesis*, 2002, 2195-2202, (ii) the reaction of nucleophilic displacement of the bis(2-tert-butyloxycarbonylaminoethyl)amine, resulting from the preceding stage, on 2-azidoethyl p-toluenesulphonate, the latter compound being obtained from commercial 2-bromoethanol by reaction with sodium azide in N,N-dimethylformamide (DMF), followed by reaction of the resulting 2-azidoethanol with p-toluenesulphonyl chloride, (iii) hydrolysis of the Boc groups by trifluoroacetic acid-water 1:1, (iv) coupling of the diamine resulting from the preceding stage with an isocyanate or isothiocyanate of formula R—NCX', X' and R having the meaning indicated above, and (v) conversion of the azide group on the derivative resulting from the preceding stage to an isothiocyanate group by reaction with triphenylphosphine and carbon dioxide or disulphide, according to the methods indicated above.

It is interesting to note that the use of the TREN derivative as a multiplication element is compatible with the incorporation of other multiplication elements such as those derived from TRIS or pentaerythritol, which makes it possible, in particular, to construct a dendritic-type architecture. This approach makes it possible to multiply the number of substituents and, consequently, to increase the multivalence in the case of biological recognition substituents. In the case of the glucide substituents, this makes it possible in particular to increase the affinity vis-a-vis a complementary biological receptor (lectin).

The methods described above for obtaining the ureido-, thioureido-, ureidocysteaminyl- and thioureidocysteaminyl-cyclodextrins of the invention are very useful as they make it possible to obtain the desired derivatives in a reduced number of stages and with high yields. Moreover, these methods make it possible to introduce a very great molecular diversity into the structure, with the possibility of incorporating different substituents, both homogeneous and heterogeneous, which is compatible with the preparation of libraries of compounds which are not readily accessible by other routes. The derivatives which incorporate multivalent oligosaccharide substituents are very effectively recognized by specific membrane lectins, as a function of the incorporated glucide substituents.

The compounds of the abovementioned formula (F) can be obtained from a cyclodextrin precursor of 6$^I$-amino-6$^I$-deoxy type and a multiplication element derived from TREN. According to molecular modelling studies, the distance between the two cyclodextrin rings is particularly well-suited to the formation of sandwich-type complexes with taxane derivatives, and in particular with docetaxel (Taxotere). This hypothesis has been confirmed experimentally (see below). Moreover, the fact of having a trisubstituted nitrogen atom in the dimerization element (i.e., W=N in formula (I) instead of a methyne group (W=CH) facilitates the characterization of the molecule by NMR.

The compounds corresponding to the abovementioned formula (D) can easily be obtained by acid hydrolysis of the Boc protective group in the derivatives of formula (F).

The compounds of the abovementioned formula (E) can be prepared from the compounds of formula (F) above by reaction with an isothiocyanate derivative, as described below.

The present invention also relates to an inclusion complex of a compound as defined. above, of formula (I), with a pharmacologically active molecule, the molar ratio between the compound as defined above and the pharmacologically active molecule being approximately 10:1 to approximately 1:2.

The expression "inclusion complex" designates the supramolecular entity formed by the compound according to the invention (host molecule) and the pharmacologically active molecule (guest molecule), in which the guest molecule is maintained in the hydrophobic cavity of the host molecule by means of non-covalent interactions.

The expression "pharmacologically active molecule" designates an active ingredient provided with therapeutic activity, such as an anticoagulant, antidiabetic, anti-inflammatory, antibiotic, antineoplastic agent, etc.

The present invention also relates to a complex as defined above, characterized in that the pharmacologically active molecule is a ditopic molecule, capable of interacting simultaneously with two cyclodextrin sub-units, such as a molecule having two aromatic rings, such as for example a Taxol derivative, or a sufficiently large size, such as for example a steroid.

The present invention also relates to a complex as defined above, characterized in that the pharmacologically active molecule is an antineoplastic agent, belonging in particular to the taxol family.

There can in particular be mentioned as antineoplastic agents, those of non-biological synthesis approved by the FDA (Food and Drug Administration) such as:
  alkylating agents: nitrosoureas such as: lomustine, carmustine and streptozocin; mustard oils such as: mechlorethamine, melphalan, uracil nitrogen mustard, chlorambucil, cyclophosphamide and iphosphamide; other alkylation agents such as: cisplatin, carboplatin, mitomycin, thiotepa, decarbazine, procarbazine, hexamethyl melamine, triethylene melamine, bisulphan, pipobroman, and mitotane;
  antimetabolites: methotrexate, trimetrexate, pentostatin, cytarabine, ara-CMP, fludarabine phosphate, hydroxyurea, fluorouracil, floxuridine, chlorodeoxyadenosine, gemcitabine, thioguanine and 6-mercaptopurine;
  DNA cleavage agents: bleomycin; topoisomerase I poisons such as: topotecan, irinotecan, camptothecin sodium salt and topotecan and irinotecan analogues; topoisomerase II poisons such as: daunorubicin, doxorubicin, idarubicin, mitoxantrone, teniposide and etoposide;
  DNA-intercalating agents: dactinomycin and mithramycin;
  mitosis inhibitors: vinblastine, vincristine, navelbine, paclitaxel and docetaxel.

A preferred antineoplastic agent, belonging to the taxol family, is docetaxel (Taxotere®).

A significant increase is generally observed in the solubilization ability of antineoplastic agents by the ureido-, thioureido-, ureidocysteaminyl- and thioureidocysteaminyl-cyclodextrin dimers of the invention in comparison with the monomer derivatives of the prior art.

The affinity of the ureido-, thioureido-, ureidocysteaminyl- and thioureidocysteaminyl-cyclodextrin dimers of the invention which incorporate glucide substituents for specific membrane lectins in vitro is evaluated according to the ELLA ("Enzyme-Linked Lectin Assay") protocol. Numerous examples of application of this protocol can be found in the article by J. J. Lundquist and E. J. Toon in *Chem. Rev.* 2002, 102, pp. 555-578. This technique measures the ability of a soluble mono- or oligosaccharide ligand to inhibit the association between a complementary lectin and another reference ligand bound to a plastic support microplate. Thus, the ureido-, thioureido-, ureidocysteaminyl- and thioureidocysteaminyl-cyclodextrin dimers carrying $\alpha$-D-mannopyranosyl substituents are recognized by concanavalin A or by the mannose-specific lectin of the macrophages, the derivatives with $\beta$-lactosyl substituents are recognized by the lactose-specific lectin of *Arachys hypogaea* or hepatocytes, and the derivatives comprising the tetrasaccharide sialyl-Lewis X substituent are recognized by the selectins of the endothelium involved in the inflammation method.

A significant increase is generally observed in the affinity of the cyclodextrin dimer-type derivatives which incorporate glucide substituents with a multivalent presentation vis-à-vis the specific lectins, in comparison with the monovalent-type conjugates or with the thioureido-cyclodextrin-type derivatives persubstituted in primary alcohol position described in the document *ChemBioChem* 2001.

The ureido-, thioureido-, ureidocysteaminyl- and thioureidocysteaminyl-cyclodextrin dimers of the invention comprising cell recognition elements with a multivalent presentation can be used in particular for the vectorized transport of pharmacologically active ingredients towards the complementary membrane receptors and also to mask these complementary membrane receptors. Thus, the polymannosylated ureido-, thioureido-, ureidocysteaminyl- and thioureidocysteaminyl-cyclodextrin dimers make it possible to target or block the mannose-specific receptor of the macrophages, the polylactosylated derivatives, the lactose-specific receptor of the hepatocytes and the derivatives incorporating substituents derived from sialyl Lewis X tetrasaccharide, endothelial selectins. In this context, these derivatives can be used as active molecules in the prevention and treatment of infection and cancerization methods involving adhesion phenomena and also for the prevention and treatment of diseases linked with disturbance of the inflammation method.

These inclusion compounds can be prepared by standard methods, for example by dispersion of the active molecule in solution or in the pure state in a solution of the cyclodextrin derivative, in the presence or absence of a cosolvent, as described in the document WO 97/33919.

These inclusion complexes can be prepared for example by adding to a solution or to a suspension of the compound of the invention of formula (I) the pharmacologically active molecule in solution or in the pure state. The inclusion complex thus formed can be isolated by lyophilization.

In the case where the pharmacologically active molecule is added in solution, for example an antineoplastic agent of the taxol family, a concentrated solution of the molecule in an organic solvent miscible with water is used, for example acetone, and the mixture obtained is stirred, and inert gas such as nitrogen is bubbled through, in order to eliminate the organic solvent.

In the case of the compounds of the taxol family, such as Taxotere®, it is also possible to disperse this product in the pure state in a sterile solution of a compound according to the invention.

The present invention also relates to a pharmaceutical composition comprising a compound as defined above, or an inclusion complex as defined above, with a pharmacologically acceptable vehicle.

The present invention relates to a pharmaceutical composition as defined above, in the form of aqueous solution.

The present invention relates to a pharmaceutical composition as defined above, characterized in that it contains per unit dose approximately 50 mg to approximately 500 mg of one of the compounds as defined above, or in that it contains per unit dose approximately 100 mg to approximately 750 mg of one of the complexes as defined above.

These pharmaceutical compositions, which can be administered by oral or parenteral route, are for example solutions, powders, suspensions, etc., in particular injectable solutions.

Other characteristics and advantages of the invention will became more clearly apparent on reading the following examples, provided of course by way of illustration and non-limitatively.

EXPERIMENTAL PART

EXAMPLE 1

Preparation of 2-tert-butoxycarbonylaminoethyl bis [2-[N'-(6$^I$-deoxycyclomaltoheptaos-6$^I$-yl)thioureido] ethyl]amine (compound no. 1)

This compound corresponds to formula (I) given above with A=H, n=n'=2, m=6, in which X represents a sulphur atom, Y represents NH, W represents a nitrogen atom and Z represents the (CH$_2$)$_2$NHBoc group (see also formula (F) given above with m=6). Compound no. 1 therefore corresponds to the following formula:

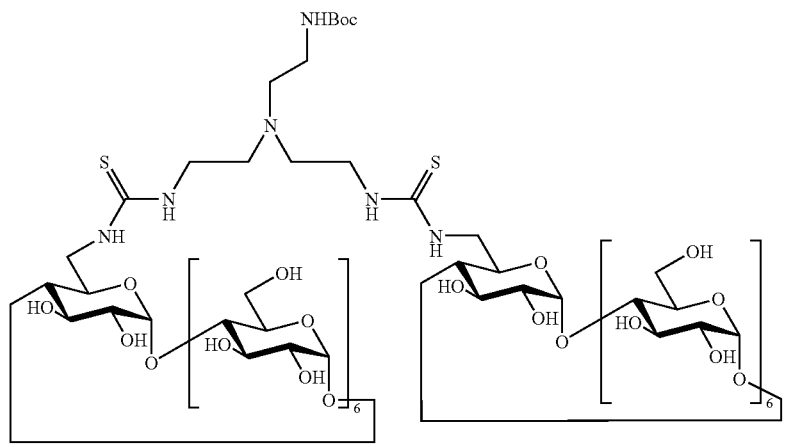

This compound is prepared by carrying out the following stages:

a) Preparation of bis(2-aminoethyl) 2-tert-butoxycarbonylaminoethyl amine.

A solution of di-tert-butyl carbonate (1.52 g; 7 mmoles) in dioxane (30 ml) is added dropwise to a stirred solution of tris(2-aminoethyl)amine (TREN: N(CH$_2$—CH$_2$—NH$_2$)$_3$) (5 g, 35 mmol) in dioxane (30 ml). The reaction mixture is stirred at ambient temperature for 16 hours, then evaporated under reduced pressure. The residue is taken up in water (10 ml) and extracted with dichloromethane (6×15 ml). Evaporation of the organic solvent leads to the compound bis(2-aminoethyl) 2-tert-butoxycarbonylaminoethyl amine in the form of an oil (1.19 g; 90%) having the following characteristics:

mass spectrum (FAB$^+$): m/z 247 [100, M+H]$^+$;

$^1$H NMR data (500 MHz, CD$_3$OD): δ 2.69 (t; 4 H; $^3J_{H,H}$ 6.3 Hz; CH$_2$NH$_2$); 2.67 (t; 2 H; $^3J_{H,H}$ 6.3 Hz; CH$_2$NHBoc); 2.50 (t; 6 H; CH$_2$N); 1.43 (s; 9 H; CMe$_3$);

$^{13}$C NMR data (125.7 MHz; MeOD): δ 158.5 (CO); 79.8 (CMe$_3$); 58.2 (NCH$_2$CH$_2$NH$_2$); 55.3 (NCH$_2$CH$_2$NHBoc); 40.2 (CH$_2$NH$_2$); 39.7 (CH$_2$NHBoc); 28.9 (CMe$_3$).

b) Preparation of bis(2-isothiocyanatoethyl) 2-tert-butoxycarbonylaminoethylamine.

Thiophosgene (0.58 ml; 7.5 mmol; 1.5 equiv) is added to a heterogeneous mixture of bis(2-aminoethyl) 2-tert-butoxycarbonylaminoethyl amine (1.19 g; 5 mmol) (compound as obtained in the preceding stage) and calcium carbonate (1.5 g; 15 mmol; 3 equiv) in water-dichloromethane (1:1, 16 ml). The reaction mixture is stirred at ambient temperature for 1 h, then concentrated. The organic phase is separated, dried by adding anhydrous magnesium sulphate, filtered and concentrated. The resulting residue is purified by silica gel column chromatography with ethyl acetate-petroleum ether 1:3. 0.99 g (60%) of the compound bis(2-isothiocyanatoethyl) 2-tert-butoxycarbonylaminoethylamine is thus obtained in the form of a colourless oil having the following characteristics:

mass spectrum (FAB$^+$): m/z 353 (100%, [M+Na]$^+$), 331 (80%, [M+H]$^+$)

$^1$H NMR data (400 MHz, CDCl$_3$): δ 5.06 (bs, 1 H, NHBoc); 3.52 (t, 4 H, $^3J_{H,H}$ 6.5 Hz, CH$_2$NCS); 3.14 (q, 2 H, $^3J_{H,H}$ 6.5 Hz, CH$_2$NHBoc); 2.83 (t, 4 H, CH$_2$CH$_2$NCS); 2.65 (t, 2 H, CH$_2$CH$_2$NHBoc); 1.40 (s, 9 H, CMe$_3$)

$^{13}$C NMR data (100.6 MHz, CDCl$_3$): δ 156.2 (CO); 132.8 (NCS); 79.4 (CMe$_3$); 54.3 (NCH$_2$CH$_2$NCS); 53.8

(NCH$_2$CH$_2$NHBoc); 43.9 (CH$_2$NCS); 38.7 (CH$_2$NHBoc); 28.4 (CMe$_3$).

c) Preparation of Compound No. 1

This compound is obtained by coupling reaction between bis(2-isothiocyanatoethyl) 2-tert-butoxycarbonylaminoethylamine (0.146 g; 0.44 mmol) and 6$^I$-amino-6$^I$-deoxycyclomaltoheptaose (1 g; 0.88 mmol) in pyridine (8 ml). The reaction mixture is stirred at 40° C. for 24 hours, then concentrated and the residue purified by silica gel column chromatography with acetonitrile-water-ammonium hydroxide at 28% 6:3:1. The reaction can also take place in water-acetone 1:1 at pH 8-9 (solid sodium acid carbonate) at ambient temperature for 12 hours. Compound no. 1 (0.86 g, 75%) is thus obtained in the form of a white solid having the following characteristics:

$[\alpha]_D$+97.1° (c 0.7; H$_2$O)

mass spectrum (MALDITOF$^+$): m/z 2629 (100%, [M+Na]$^+$)

$^1$H NMR (500 MHz, D$_2$O, 323 K): δ 5.26 (d, 2 H, J$_{1,2}$=3.5 Hz, H-1$^{II}$); 5,24-5.21 (m, 12 H, H-1$^{I,III-VII}$); 4.51 (m, 2 H, H-6a$^I$); 4.28 (m, 2 H, H-6a$^{II}$); 4.18 (m, 2 H, H-6b$^{II}$); 4.16 (bt, 2 H, J$_{4,5}$=J$_{5,6a}$=9.5 Hz, H-5$^I$); 4,11-4.00 (m, 50 H, H-3$^{I-VII}$, H-5$^{II-VII}$, H-6a$^{II-VII}$, H-6b$^{II-VII}$); 3.84-3.72 (m, 30 H, CH$_2$NHCS, H-2$^{I-VII}$, H-4$^{II-VII}$); 3.58 (m, 2 H, H-6b$^I$); 3.55 (t, 2 H, J$_{3,4}$=9.5 Hz, H-4$^I$); 3.28, 3.25 (2 m, 2 H, CH$_2$NHBoc); 2.95 (m, 4 H, CH$_2$CH$_2$NHCS); 2.94, 2.89 (2 m, 2 H, CH$_2$CH$_2$NHBoc); 1.68 (s, 9 H, CMe$_3$);

1D-TOCSY, units I and II (500 MHz, D$_2$O, 323 K): δ 5.21 (d, 1 H, J$_{1,2}$=3.5 Hz, H-1$^I$); 4.08 (t, 2 H, J$_{2,3}$=J$_{3,4}$=10.0 Hz, H-3$^{II}$); 4.05 (t, 2 H, J$_{2,3}$=J$_{3,4}$ 9.5 Hz, H-3$^I$); 4.05 (m, 2 H, H-5$^{II}$); 3.82 (dd, 2 H, H-2$^I$); 3.81 (dd, 2 H, H-2$^{II}$); 3.80 (t, 2 H, H4$^{II}$);

$^{13}$C NMR (125.7 MHz, D$_2$O, 323 K): δ 184.3 (CS); 159.9 (CO); 105.2-104.6 (C-1$^{I-VII}$); 86.7 (C-4$^I$); 84.3-83.6 (C-4$^{II-VII}$); 82.9 (CMe$_3$); 76.1-75.9 (C-3$^{I-VII}$); 75.2-74.7 (C-2$^{I-VII}$, C-5$^{II-VII}$); 73.4 (C-5$^I$); 63.4-62.8 (C-6$^{II-VII}$); 55.8 (CH$_2$CH$_2$NHBoc); 55.4 (CH$_2$CH$_2$NHCS); 48.4 (CH$_2$NHCS); 45.8 (C-6$^I$); 41.6 (CH$_2$NHBoc); 31.7 (CMe$_3$).

An alternative method for the preparation of bis(2-isocyanatoethyl) 2-tert-butoxycarbonylaminoethylamine, precursor for the preparation of compound no. 1 and described in paragraph b) consists of the following stages:

2-(tert-butoxycarbonylamino)ethylamine

A solution of di-tert-butyl carbonate (2.18 g; 10 mmol; 0.25 equiv) in tetrahydrofuran (30 ml) is added dropwise over a period of 1 hour to a magnetically stirred solution of ethylenediamine (2.4 g; 40 mmol) in tetrahydrofuran (30 ml) at 0° C. Stirring of the reaction mixture continues for 2 hours followed by concentration under reduced pressure. The residue is dissolved in water (10 ml) and extracted with dichloromethane (3×15 ml) leading to 1.45 g (90%) of the title compound in the form of a syrup which is used directly in the following stage.

R$_f$ 0.40 (10:1:1 MeCN-water-NH$_4$OH)

$^1$H NMR (500 MHz; MeOD): δ 3.07 (t, 2 H, $^3$J$_{H,H}$ 6.3 Hz, CH$_2$NH$_2$); 2.65 (t, 2 H, CH$_2$NHBoc); 1.41 (s, 9H, CMe$_3$) $^{13}$C NMR (125.7 MHz; MeOD): δ 157.2 (CO); 78.6 (CMe$_3$); 42.6 (CH$_2$NH$_2$); 41.0 (CH$_2$NHBoc); 27.3 (CMe$_3$).

2-Azidoethyl p-toluenesulphonate

A solution of 2-bromoethanol (5.06 g; 40.4 mmol) and sodium azide (3.12 g; 48 mmol; 1.2 equiv) in water (15 ml) is stirred at 60° C. for 4 hours, extracted with dichloromethane (4×20 ml), dried over sodium sulphate, filtered and concentrated (it should be noted that 2-azidoethanol is too volatile to be dried under a vane pump vacuum). The oily crude product is dissolved in pyridine (20 ml) at 0° C. and tosyl chloride (7.2 g; 48 mmol; 1.2 equiv) is added in small portions. The solution is taken to ambient temperature and stirred overnight. Water (10 ml) is then added and the product is extracted with dichloromethane (3×20 ml), dried over sodium sulphate and concentrated under reduced pressure in order to produce the title compound (7 g; 29 mmol; 72%).

$^1$H NMR (500 MHz, CDCl$_3$): δ 7.79; 7.34 (2 d, 4H, $^3$J$_{H,H}$ 8.0 Hz, CH—Ar); 4.13 (t, 2 H, $^3$J$_{H,H}$ 6 Hz, CH$_2$OTs); 3.46 (t, 2 H, CH$_2$N$_3$); 2.43 (s, 3 H, Me)

13C NMR (125.7 MHz; MeOD): δ 145.2; 132.6; 130.0; 128.0 (Ar); 68.0 (CH$_2$OTs); 49.6 (CH$_2$N$_3$); 21.6 (Me).

2-(tert-Butoxycarbonylamino)ethyl bis(2-azidoethyl)amine

A mixture of 2-(tert-butoxycarbonylamino)ethylamine (10 mg; 0.6 mmol), 2-azidoethyl p-toluenesulphonate (370 mg; 1.5 mmol; 1.25 equiv) and potassium carbonate (2.4 mmol, 2 equiv) is taken to reflux in nitromethane for 16 hours. The solution is then concentrated and the residual product dissolved in dichloromethane (10 ml), washed with water (5 ml) and purified by column chromatography (EtOAc-hexane 1:3) leading to the title product (130 mg, 70%).

$^1$H NMR (500 MHz; CDCl$_3$): δ 5.06 (bs, 1 H, NH); 3.32 (t, 4 H, $^3$J$_{H,H}$ 6.6 Hz, CH$_2$N$_3$); 3.18 (q, 2 H, CH$_2$NHBoc); 2.72 (t, 4 H, CH$_2$CH$_2$N$_3$); 2.64 (t, 2 H, CH$_2$CH$_2$NHBoc); 1.44 (s, 9 H, CMe$_3$)

$^{13}$C NMR (125.7 MHz; MeOD): δ 157.2 (CO); 75.5 (CMe$_3$); 54.5 (CH$_2$CH$_2$NHBoc); 54.2 (CH$_2$CH$_2$N$_3$); 50.0 (CH$_2$N$_3$); 38.9 (CH$_2$NHBoc); 28.8 (CMe$_3$).

Bis(2-isothiocyanatoethyl) 2-tert-butoxycarbonylaminoethylamine

Triphenylphosphine (0.48 mmol; 1.1 equiv) and carbon disulphide (4.4 mmol; 10 equiv) are added to a solution of 2-(tert-butoxycarbonylamino)ethyl bis(2-azidoethyl)amine (130 mg; 0.44 mmol) in dioxane (5 ml). The mixture is stirred under nitrogen at ambient temperature for 1 day, the solution is concentrated and the residue purified by silica gel column chromatography (EtOAc-petroleum ether 1:3) leading to the title product (102 mg, 70%) identical to that described in the preceding paragraph b).

EXAMPLE 2

Preparation of 2-aminoethyl bis[2-[N'-(6$^I$-deoxycyclomalto-heptaos-6$^I$-yl)thioureido]ethyl]amine (compound no. 2)

This compound corresponds to formula (I) given above with A=H, n=n'=2, m=6, in which X represents a sulphur atom, Y represents NH, W represents a nitrogen atom and Z represents the group (CH$_2$)$_2$NH$_2$ (see also formula (D) given above with m=6).

Compound no. 2 therefore corresponds to the following formula:

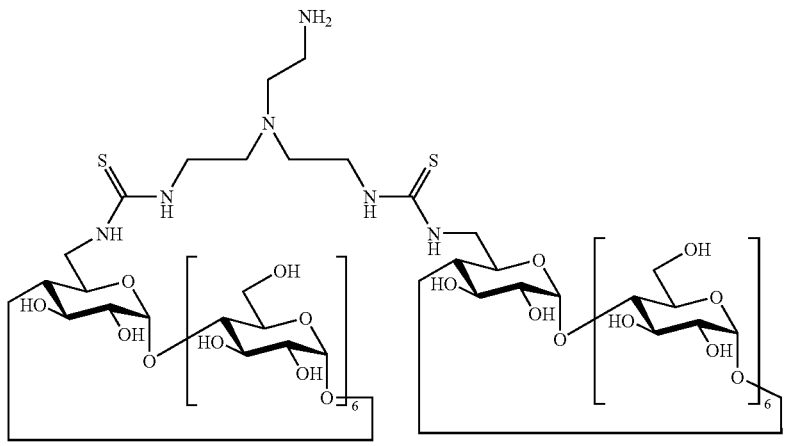

This compound is obtained from compound no. 1 (0.1 g; 0.14 mmol) by treatment with trifluoroacetic acid -water (1:1) at 40° C. for 2 hours. The evaporation of the solvents at reduced pressure, the coevaporation of the traces of acid with water and the lyophilization of the resulting residue leads to compound no. 2 in the form of a white hygroscopic solid (quantitative yield after NMR) having the following characteristics:

$[\alpha]_D$+126.1° (c 2.3; $H_2O$)

mass spectrum (MALDITOF$^+$): m/z 2498 (100%, [M +H]$^+$)

$^1$H NMR (500 MHz, $D_2O$, 333 K): δ 5,33-5.31 (m, 14 H, H-1$^{I\text{-}VII}$); 4.42 (m, 2 H, H-6a$^I$); 4.37 (m, 6 H, $CH_2N$); 4.27 (bt, 2 H, $J_{4,5}$=$J_{5,6a}$ 10.0 Hz, H-5$^1$); 4.21-4.07 (m, 50 H, H-3$^{I\text{-}VII}$, H-5$^{II\text{-}VII}$, H-6a$^{II\text{-}VII}$, H-6b$^{II\text{-}VII}$); 3.92-3.89 (m, 18 H, $CH_2NHCS$, H-2$^{I\text{-}VII}$); 3,83-3.81 (m, 14 H, $CH_2NH_2$, H-4$^{II\text{-}VII}$); 3.72 (m, 2 H, H-6b$^I$); 3.70 (t, 2H, $J_{3,4}$=10.0 Hz, H-4$^I$).

1D-TOCSY, unit I and ethylene bridges (500 MHz, $D_2O$, 323 K): δ 5.32 (d, 1 H, $J_{1,2}$=3.5 Hz, H-1$^I$); 4.19 (t, 2 H, $J_{2,3}$=$J_{3,4}$=10.0 Hz, H-3$^I$); 3.92 (dd, 2 H, H-2$^I$); 3.94 (m, 4 H, $CH_2NHCS$); 3.85 (m, 2 H, $CH_2NH_2$).

$^{13}$C NMR (125.7 MHz; $D_2O$; 333 K): δ 183.1 (CS); 102.5-101.8 (C-1$^{I\text{-}VII}$); 83.6 (C-4$^I$); 81.6-81.3 (C-4$^{I\text{-}VII}$); 73.6-73.3 (C-3$^{I\text{-}VII}$); 42.6-71.7 (C-2$^{I\text{-}VII}$, C-5$^{II\text{-}VII}$); 70.4 (C-5$^I$); 60.9-60.7 (C-6$^{II\text{-}VII}$); 54.8 ($CH_2CH_2NH_2$); 50.9 ($CH_2CH_2NHCS$); 45.8 (C-6$^I$, $CH_2NHCS$); 39.6 ($CH_2NH_2$).

Compound no. 2 is used directly as precursor for the preparation of cyclodextrin dimer derivatives corresponding to formula (I) given above with A=H, n=n'=2, m=6, in which X represents a sulphur atom, Y represents NH, W represents a nitrogen atom and Z represents the group —$(CH_2)_2$—NH—CX—NHR, R having the meaning given above, without additional purification.

EXAMPLE 3

Preparation of bis[2-[N'-(6$^I$-deoxycyclomaltoheptaos-6$^I$-yl)thioureido]ethyl] 2-(N'-methylthioureido) ethylamine (compound no. 3)

This compound corresponds to formula (I) given above with A=H, n=n'=2, m=6, in which X represents a sulphur atom, Y represents NH, W represents a nitrogen atom and Z represents the —$(CH_2)_2$—NH—CS—NHMe group (see also formula (E) with m=6, in which R represents the methyl group). This compound corresponds to the following formula: I This compound is obtained by coupling reaction between compound no. 2 (122 mg; 0.05 mmol) and commercial methyl isothiocyanate (4 mg; 0.055 mmol) in water-acetone (1:1; 4 ml) at pH 8-9 (solid sodium acid carbonate) at ambient temperature for 12 hours. Acetone is eliminated by evaporation at reduced pressure, the aqueous solution is then extracted with dichloromethane (2×5 ml) and lyophilized. The residue is taken up in water (5 ml) and demineralized by treatment with mixed ion exchange resin Duolite MB-6113 (H$^+$, OH$^-$). The resin is filtered and washed with water and the resulting aqueous solution is lyophilized again. Compound no. 3 (129 mg, 97%) is thus obtained in the form of a white solid having the following properties:

$[\alpha]_D$+85.4° (c 1.0; $H_2O$)

mass spectrum (MALDITOF$^+$): m/z 2594 (100%, [M+Na]$^+$)

solubility in water: 325 g·L$^{-1}$ (126 mmol·L$^{-1}$)

$^1$H NMR (500 MHz, $D_2O$, 353 K): δ 5,55-5.52 (m, 14 H, H-1$^{I\text{-}VII}$); 4.67 (m, 2 H, H-6a$^I$); 4.52 (m, 2 H, H-5$^I$); 4,44-4.35 (m, 50 H, H-3$^{I\text{-}VII}$, H-5$^{II\text{-}VII}$, H-6a$^{II\text{-}VII}$, H-6b$^{II\text{-}VII}$); 4.13-4.10 (m, 14 H, H-2$^{I\text{-}VII}$); 4,07-4.04 (m, 18 H, H4$^{II\text{-}VII}$, $CH_2NHCS$); 3.89 (m, 4 H, H4$^I$, H-6b$^I$); 3.52 (s, 3 H, MeN); 3.32 (m, 6 H, $NCH_2$)

$^{13}$C NMR (125.7 MHz; $D_2O$; 353 K): δ 182.2 (CS); 102.7-100.9 (C-1$^{I\text{-}VII}$); 83.9 (C-4$^I$); 81.8-81.4 (C-4$^{II\text{-}VII}$); 73.8-73.6 (C-3$^{I\text{-}VII}$); 72.8-72.4 (C-2$^{I\text{-}VII}$, C-5$^{II\text{-}VII}$); 70.6 (C-5$^I$); 61.4-61.0 (C-6$^{II\text{-}VII}$); 53.4 ($NCH_2$); 45.7 (C-6$^I$); 42.4 ($CH_2NH$); 31.9 (Me).

EXAMPLE 4

Preparation of bis[2-[N'-(6$^I$-deoxycyclomaltohep-taos-6$^I$-yl)thioureido]ethyl] 2-(N'-phenylthioureido) ethylamine (compound no. 4)

This compound corresponds to formula (I) given above with A=H, n=n'=2, m=6, in which X represents a sulphur atom, Y represents NH, W represents a nitrogen atom and Z represents the $(CH_2)_2NHC(=S)NHPh$ group (see also formula (E) with m=6, in which R represents the phenyl group). This compound corresponds to the following formula:

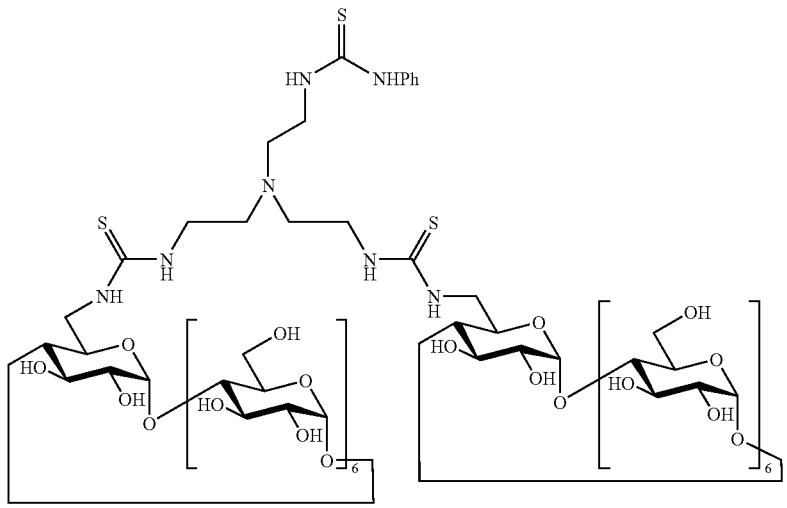

This compound is obtained by coupling reaction between compound no. 2 (122 mg; 0.05 mmol) and commercial phenyl isothiocyanate (7.4 mg; 0.055 mmol) in water-acetone (1:1, 4 ml) at pH 8-9 (solid sodium acid carbonate) at ambient temperature for 12 hours, as described above for the preparation of compound no. 3. After demineralization and lyophilization, compound no. 4 (101.4 mg; 77%) is obtained in the form of a white solid having the following properties:

$[\alpha]_D$ +97.4° (c 1.0; $H_2O$)

mass spectrum (MALDITOF$^+$): m/z 2655 (100%, [M+Na]$^+$)

solubility in water: 115 g·L$^{-1}$ (62 mmol·L$^{-1}$)

$^1$H NMR (500 MHz, $D_2O$, 353 K): δ 7.40-7.30 (m, 5 H, Ph); 5.55-5.52 (m, 14 H, H-1$^{I-VII}$); 4.66 (m, 2 H, H-6a$^I$); 4.51 (m, 2 H, H-5$^I$); 4.44-4.35 (m, 50 H, H-3$^{I-VII}$, H-5$^{II-VII}$, H-6a$^{II-VII}$, H-6b$^{II-VII}$); 4.13-4.10 (m, 14 H, H-2$^{I-VII}$); 4.07-4.04 (m, 18 H, H-4$^{II-VII}$, CH$_2$NHCS); 3.89 (m, 4 H, H-4$^I$, H-6b$^I$); 3.32 (m, 6 H, NCH$_2$);

$^{13}$C NMR (125.7 MHz; $D_2O$; 353 K): δ 182.2 (CS); 138.0; 128.9; 127.5; 127.1 (Ph); 102.7-100.9 (C-1$^{I-VII}$); 84.0 (C-4$^I$); 81.8-81.4 (C-4$^{II-VII}$); 73.8-73.6 (C-3$^{I-VII}$); 72.8-72.4 (C-2$^{I-VII}$, C-5$^{II-VII}$); 70.5 (C-5$^I$); 61.4-61.0 (C-6$^{II-VII}$); 53.3 (NCH$_2$); 45.6 (C-6$^I$); 42.3 (CH$_2$NH)

EXAMPLE 5

Preparation of bis[2-[N'-(6$^I$-deoxycyclomaltoheptaos-6$^I$-yl)thioureido]ethyl] 2-[N'-(α-D-mannopyranosyl)thioureido]ethylamine (compound no. 5)

This compound corresponds to formula (I) given above with A=H, n=n'=2, m=6, in which X represents a sulphur atom, Y represents NH, W represents a nitrogen atom and Z represents the (CH$_2$)$_2$NHC(=S)NHR group, R corresponding to formula (III) (see also formula (E-c) with m=6). This compound therefore corresponds to the following formula.

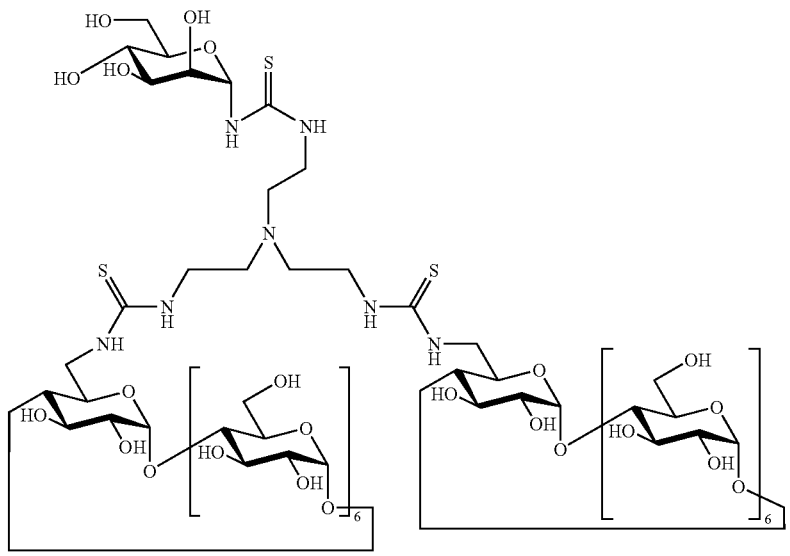

This compound is obtained according to the following stages:

a) Preparation of bis[2-[N'-($6^I$-deoxycyclomaltoheptaos-$6^I$-yl)thioureido]ethyl] 2-[N'-(2,3,4,6tetra-O-acetyl-α-D-mannopyranosyl)thioureidol ethylamine.

This compound is obtained by coupling reaction between compound no. 2 (122 mg; 0.05 mmol) and 2,3,4,6-tetra-O-acetyl-α-D-mannopyranosyl isothiocyanate (19 mg; 0.05 mmol) in water-acetone (1:1, 4 ml) at pH 8-9 (solid sodium acid carbonate) at ambient temperature for 4 hours. Acetone is eliminated under reduced pressure, the aqueous solution is lyophilized, and the residue is taken up in water (5 ml), demineralized and lyophilized again as described above for compound no. 3. The title compound (137 mg, 95%) is thus obtained in the form of a white solid having the following properties:

$[\alpha]_D$+99.6° (c 2.4; $H_2O$)

$^1$H NMR (500 MHz, $D_2O$, 343 K): δ 6.28 (bs, 1 H, H-1'); 5.81 (dd, 1 H, $J_{2,3}$ 3.5 Hz, $J_{3,4}$ 8.5 Hz, H-3'); 5.74 (t, 1 H, $J_{1,2}$ 3.5 Hz, H-2'); 5.60 (t, 1 H, $J_{4,5}$ 8.5 Hz, H-4'); 5.44-5.43 (m, 14 H, H-1$^{I\text{-}VII}$); 4.76 (dd, 1 H, $J_{5,6a}$ 4.5 Hz, $J_{6a,6b}$ 13.0 Hz, H-6a'); 4.66 (m, 2 H, H-6a$^I$); 4.55 (m, 2 H, H-6a$^{II}$); 4.54 (bd, 1 H, H-6b'); 4.43 (m, 1 H, H-5'); 4.42 (m, 4 H, H-5$^I$, H-6b$^{II}$); 4.38-4.13 (m, 50 H, H-3$^{I\text{-}VII}$, H-5$^{II\text{-}VII}$, H-6a$^{II\text{-}VII}$, H-6b$^{II\text{-}VII}$); 4.03-4.01 (m, 20 H, $CH_2NHCS$, H-2$^{I\text{-}VII}$); 4.00-3.93 (m, 12 H, H-4$^{II\text{-}VII}$); 3.84 (m, 2 H, H-6b$^I$); 3.77 (t, 2 H, $J_{3,4}$=9.5 Hz, H-4$^I$); 3.31 (m, 6 H, $NCH_2$); 2.62; 2.53; 2.52; 2.47 (4 s, 12 H, MeCO)

$^{13}$C NMR (125.7 MHz; $D_2O$; 343 K): δ 183.0 (CS); 173.8; 172.9 (CO); 102.5-101.9 (C-1$^{I\text{-}VII}$); 83.7 (C-4$^I$); 81.6-81.2 (C-4$^{II\text{-}VII}$, C-1'); 73.6-73.4 (C-3$^{I\text{-}VII}$); 72.6-71.7 (C-2$^{I\text{-}VII}$, C-5$^{II\text{-}VII}$); 70.3 (C-5$^I$, C-5'); 69.8-69.6 (C-2', C-3'); 67.1 (C-4'); 60.9-60.6 (C-6$^{II\text{-}VII}$); 60.3 (C-6'); 53.2 ($NCH_2$); 46.0 (C-6$^I$); 42.0 ($CH_2NHCS$); 20.4; 20.2; 20.1 (MeCO).

b) Preparation of Compound No. 5

A 1 N solution of sodium methylate in methanol (70 ml; 0.5 equiv) is added to a solution of bis[2-[N'-($6^I$-deoxycyclomaltoheptaos-$6^I$-yl)thioureido]ethyl] 2-[N'-(2,3,4,6-tetra-O-acetyl-α-D-mannopyranosyl)thioureido]ethylamine (50 mg, 17 μmol) in dry methanol (5 ml), and the solution is stirred at 0° C. for 10 minutes. The precipitation of a white solid is observed which is redissolved by addition of water (0.5 ml). The aqueous solution is stirred at 0° C. for 10 minutes, neutralized and demineralized by successive treatment with the acid exchange resin Amberlite IR-120 ($H^+$) and the mixed resin Duolite MB-6331 ($H^+$, $OH^-$), filtered and lyophilized. Compound no. 5 (46.2 mg; 100%) is thus obtained in the form of a white solid having the following characteristics:

$[\alpha]_D$+113.0° (c 1.0; $H_2O$)

mass spectrum (MALDITOF$^+$): m/z 2742 (100%, [M+Na]$^+$)

solubility in water: 375 g·$L^{-1}$ (138 mmol·$L^{-1}$)

$^{13}$C NMR (125.7 MHz; $D_2O$; 333 K): δ 183.8; 183.2 (CS); 102.6-101.9 (C-1$^{I\text{-}VII}$); 83.8 (C-4$^I$); 82.3-81.3 (C-4$^{II\text{-}VII}$); 77.9 (C-1'); 74.0-73.3 (C-3$^{I\text{-}VII}$);73.0-72.3 (C-2$^{I\text{-}VII}$, C-5$^{II\text{-}VII}$); 70.9 (C-5$^I$, C-5'); 70.7, 70.4 (C-3', C-2'); 67.1 (C-4'); 61.6 (C-6'); 61.4-60.6 (C-6$^{II\text{-}VII}$); 55.0; 54.7 ($CH_2N$); 46.2 (C-6$^I$); 40.0 ($CH_2NHCS$).

EXAMPLE 6

Preparation of bis[2-[N'-($6^I$-deoxycyclomaltoheptaos-$6^I$-yl)thioureido]ethyl] 2-[N'-[tris(2,3,4,6-tetra-O-acetyl-α-D-mannopyranosyloxy-methyl)methyl]thioureido]lethylamine (compound no. 6)

This compound corresponds to formula (I) given above with A=H, n=n'=2, m=6, in which X represents a sulphur atom, Y represents NH, W represents a nitrogen atom and Z represents the $(CH_2)_2NHC(=S)NHR$ group, R corresponding to formula (IV) as defined previously (see also formula (E-h) with m=6). This compound therefore corresponds to the following formula:

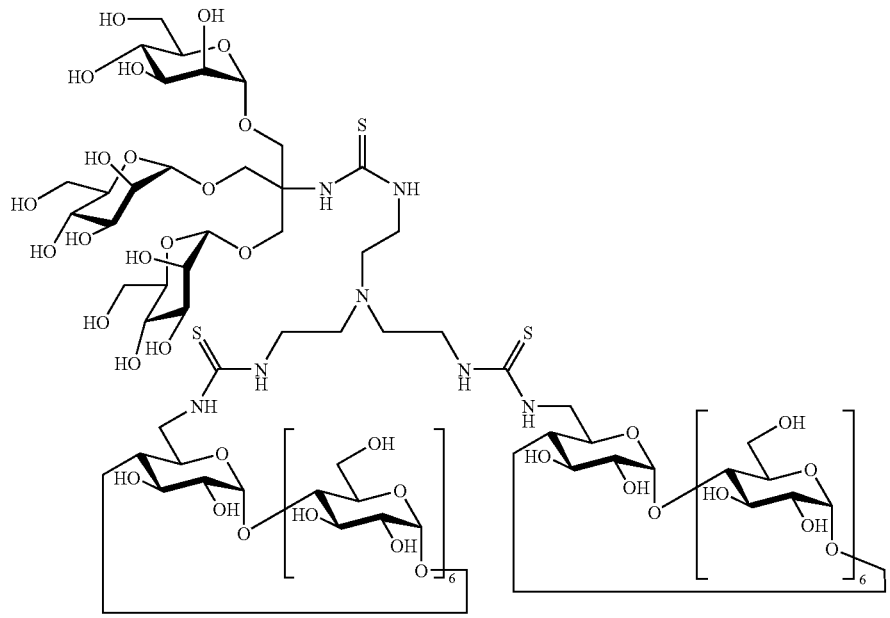

This compound is obtained by carrying out the following stages:

a) Preparation of bis[2-[N'-($6^I$-deoxycyclomaltoheptaos-$6^I$-yl)thioureido]ethyl] 2-[N'-[tris(2,3,4,6-tetra-O-acetyle-α-D-mannopyranosyloxymethyl)methyl]thioureido]ethylamine.

This compound is obtained by coupling reaction between compound no. 2 (122 mg; 0.05 mmol) and tris(2,3,4,6-tetra-O-acetyl-a-D-mannopyranosyloxymethyl)methyl isothiocyanate (57.7 mg; 0.05 mmol) in water-acetone (1:1, 4 ml) at pH 8-9 (solid sodium acid carbonate) at ambient temperature for 16 hours. Acetone is eliminated under reduced pressure, the aqueous solution is lyophilized, and the residue is taken up in water (5 ml), demineralized and lyophilized again as described above for compound no. 3. The title compound (155 mg, 85%) is thus obtained in the form of a white solid having the following properties:

$[\alpha]_D$+55.1° (c 1.0,$H_2O$)

$^1$H NMR (500 MHz, $D_2O$, 353 K): δ 5.80-5.74 (m, 9 H, H-2', H-3', H-4'); 5.55-5.52 (m, 14 H, H-$1^{I\text{-}VII}$); 5.50 (bs, 3 H, H-1'); 4.85 (bd, 3 H, $J_{6a,6b}$ 12.0 Hz, H-6a'); 4.71 (bd, 3 H, H-6b'); 4.65 (m, 5 H, H-5'); 4.67 (m, 2 H, H-$6a^I$); 4.52 (m, 2 H, H-$5^I$); 4,44-4.35 (m, 56 H, H-$3^{I\text{-}VII}$, H-$5^{II\text{-}VII}$, H-$6a^{II\text{-}VII}$, H-$6b^{II\text{-}VII}$, $OCH_2$); 4,134.10 (m, 14 H, H-$2^{I\text{-}VII}$); 4,07-4.04 (m, 18 H, $H4^{II\text{-}VII}$, $CH_2$NHCS); 3.89 (m, 4 H, $H4^I$, $H\text{-}6b^I$); 3.32 (m, 6 H, $NCH_2$); 2.65; 2.62; 2.57; 2.52 (4 s, 36 H, MeCO);

$^{13}$C NMR (125.7 MHz, $D_2O$, 353 K): δ 182.2 (CS); 173.9; 173.0 (CO); 102.7-100.9 (C-$1^{I\text{-}VII}$); 98.4 (C-1'); 83.9 ($C4^I$); 81.8-81.4 (C-$4^{II\text{-}VII}$); 73.8-73.6 (C-$3^{I\text{-}VII}$); 72.8-72.4 (C-$2^{I\text{-}VII}$, C-$5^{II\text{-}VII}$); 70.6 (C-$5^I$); 70.3 (C-2'); 70.0 (C-3'); 69.4 (C-5'); 66.8 (C-4', $OCH_2$); 62.9 (C-6'); 61.4-61.0 (C-$6^{II\text{-}VII}$); 53.4 ($NCH_2$); 45.7 (C-$6^I$); 42.4 ($CH_2$NH); 20.7 (Me).

b) Preparation of compound no. 6

A 1 N solution of sodium methylate in methanol (70 ml; 0.5 equiv) is added to a solution of bis[2-[N'-($6^I$-deoxycyclomaltoheptaos-$6^I$-yl)thioureido]ethyl] 2-[N'-[tris(2,3,4,6-tetra-O-acetyl-α-D-mannopyranosyloxymethyl)methyl]thioureido]ethyl amine (80 mg, 22 μmol) in dry methanol (5 ml), and the solution is stirred at ambient temperature for 1 hour. The precipitation of a white solid is observed which is redissolved in water (0.5 ml). The aqueous solution is stirred at 0° C. for 30 minutes, neutralized and demineralized by successive treatment with the acid exchange resin Amberlite IR-120 ($H^+$) and the mixed resin Duolite MB-6331 ($H^+$, $OH^-$), as indicated above for the preparation of compound no. 5, filtered and lyophilized. Compound no. 6 (68.5 mg; yield 99%) is thus obtained in the form of a white solid having the following characteristics:

$[\alpha]_D$+95.2° (c 1.0; $H_2O$)

solubility in water: 400 g·$L^{-1}$ (127 mmol·$L^{-1}$)

mass spectrum (MALDITOF$^+$): m/z 3170 (100%, [M+Na]$^+$)

$^1$H NMR (500 MHz, $D_2O$, 353 K): δ 5.54 (m, 14 H, H-$1^{I\text{-}VII}$); 5.35 (m, 9 H, H-2', H-3', H-4'); 5.31 (bs, 3 H, H-1'); 4.61 (d, 3 H, $^2J_{H,H}$ 10.0 Hz, $OCH_2$a); 4.50-4.32 (m, 63 H, H-$3^{I\text{-}VII}$, H-$5^{I\text{-}VII}$, H-$6a^{I\text{-}VII}$, H-$6b^{II\text{-}VII}$, $CH_2$N, $OCH_2$b); 4.14-4.10 (m, 14 H, H-$2^{I\text{-}VII}$); 4.10-4.03 (m, 18 H, H-$4^{II\text{-}VII}$, $CH_2$NH); 3.95 (m, 4 H, H-$4^I$, H-$6b^I$)

$^{13}$C NMR (125.7 MHz, $D_2O$, 353 K): δ 183.8 (CS); 1037-102.0 (C-$1^{I\text{-}VII}$); 101.2 (C-1'); 83.3 (C-$4^I$); 81.9-81.6 (C-$4^{II\text{-}VII}$); 74.2-73.5 (C-$3^{I\text{-}VII}$); 72.9-72.1 (C-$2^{I\text{-}VII}$, C-$5^{I\text{-}VII}$); 71.6 (C-$5^I$); 70.9-70.5 (C-3', C-2', C-5'); 67.5 (C-4', $OCH_2$); 61.7 (C-6'); 61.2-60.9 (C-$6I^{I\text{-}VII}$); 55.1 ($CH_2$N); 46.0 (C-$6^I$); 39.9 ($CH_2$NHCS).

EXAMPLE 7

Preparation of bis[2-[N'-($6^I$-deoxycyclomaltoheptaos-$6^I$-yl)thioureido]ethyl] 2-[N'-[2-[bis[2-[N'-(α-D-mannopyranosyl)thioureido]ethyl] amino]ethyl]thioureido]ethyl amine (compound no. 7)

This compound corresponds to formula (I) given above with A=H, n=n'=2, m=6, in which X represents a sulphur atom, Y represents NH, W represents a nitrogen atom and Z represents the $(CH_2)_2$NHC(=S)NH$(CH_2)_2$N[$(CH_2)_2$NHC(=S)NHR']$_2$ group, R' corresponding to formula (III) given above (see also formula (H-a) with m=6). This compound therefore corresponds to the following formula:

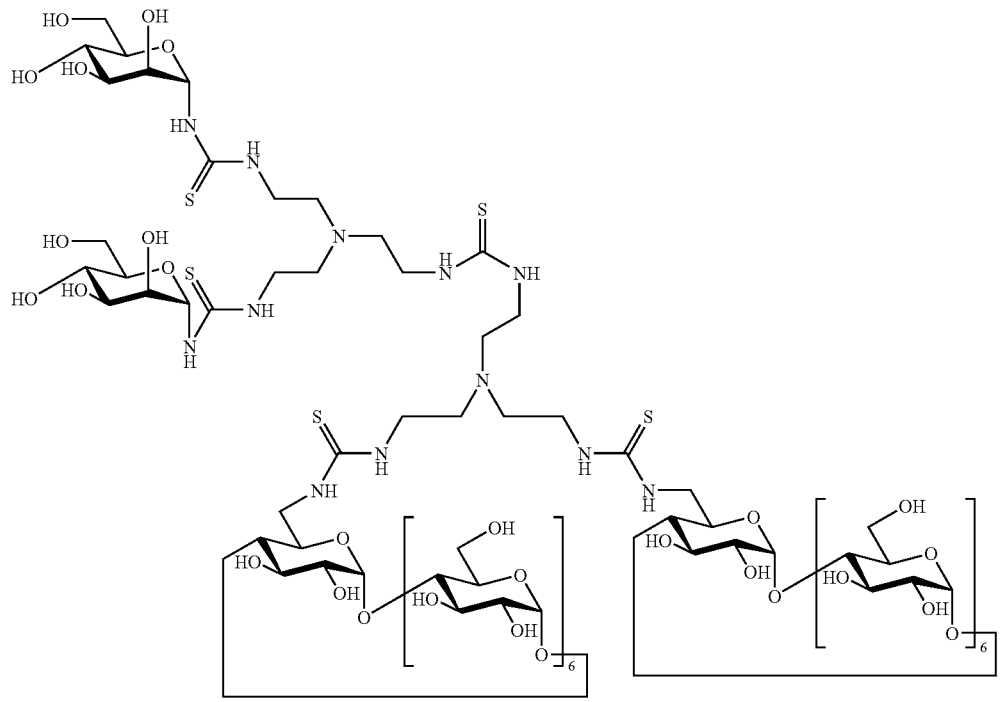

This compound is obtained by carrying out the following stages:

a) Preparation of bis(2-tert-butoxycarbonylaminoethyl) amine

A solution of diethylenetriamine (0.42 g; 4.1 mmol) in tetrahydrofuran (THF; 5 ml) is stirred at 0° C. under nitrogen for 20 minutes. A solution of 2-(tert-butoxycarbonyloxyimino)-2-phenylacetonitrile (Boc-ON; 2.04 g; 8.2 mmol) in THF (5 ml) is then added dropwise and the reaction mixture is stirred at 0° C. for 1 hour. The solvent is eliminated at reduced pressure and the resulting residue is purified by silica gel column chromatography with methanol-ammonium hydroxide 100:3. 1.2 g (yield 96%) of an oil having the following characteristics is thus obtained:

mass spectrum (CI$^+$): m/z 304 [M+H]$^+$ $^1$H NMR (500 MHz, CDCl$_3$, 313 K): δ 5.04 (bs, 2 H, NHBoc); 4.56 (bs, 1 H, NH); 3.19 (q, 4 H, $^3J_{H,H}$ 5.7 Hz, CH$_2$NHBoc); 2.71 (t, 4 H, CH$_2$NH); 1.41 (s, 18 H, CMe$_3$)

$^{13}$C NMR (125.7 MHz; CDCl$_3$, 313 K): δ 156.2 (CO); 79.2 (CMe$_3$); 48.7 (CH$_2$NH); 40.2 (CH$_2$NHBoc); 28.3 (CMe$_3$).

b) Preparation of 2-azido ethyl tosylate.

A mixture of 2-bromoethanol (3 g, 24 mmol) and sodium azide (3.12 g; 48 mmol) in acetonitrile (10 ml) is stirred at reflux for 24 hours, then filtered and the solvent is eliminated under reduced pressure. The residue is taken up in pyridine (10 ml) and tosyl chloride (4.57 g; 24 mmol) is added to the resulting solution, followed by stirring at ambient temperature for 2 hours. Dichloromethane (40 ml) is added and the organic phase is washed with a 2 N solution of sulphuric acid (3×40 ml), dried (anhydrous sodium sulphate) and concentrated. 4.63 g (yield 80%) of an oil having the following characteristics is thus obtained:

mass spectrum (CI$^+$): m/z 242 [M +H]$^+$ $^1$H NMR (300 MHz, CDCl$_3$): δ 7.81; 7.35 (2 d, 4 H, $^3J_{H,H}$ 8.3 Hz, Ph); 4.15 (t, 2 H, $^3J_{H,H}$ 5.0 Hz, CH$_2$OTs); 3.48 (t, 2 H, CH$_2$N$_3$)

$^{13}$C NMR (75.5 MHz; CDCl$_3$): δ 145.1; 132.4; 129.8; 127.8 (Ph); 67.9 (CH$_2$OTs); 49.4 (CH$_2$N$_3$); 21.5 (Me).

c) Preparation of 2-azidoethyl bis(2-tert-butoxycarbonylaminoethyl)] amine.

2-azidoethyl tosylate (0.24 g; 1.5 equiv; 1 mmol) is added to a solution of bis(2-tert -butoxycarbonylaminoethyl)amine (0.2 g; 0.66 mmol) in N,N-dimethylformamide (2 ml). The reaction mixture is stirred at 60° C. overnight, then concentrated at reduced pressure, the residue is taken up in dichloromethane (5 ml), the organic phase is washed with water (2×5 ml), dried over anhydrous sodium sulphate and concentrated. The residue is purified by silica gel column chromatography with ethyl acetate-petroleum ether. 0.125 g (yield 70%) of an oil having the following characteristics is thus obtained:

mass spectrum (CI$^+$): m/z 373 [M+H]$^+$ $^1$H NMR (500 MHz, CDCl$_3$): δ 5.05 (bs, 2 H, NHBOc); 3.29 (t, 2 H, $^3J_{H,H}$ 6.0 Hz, CH$_2$N$_3$); 3.15 (q, 4 H, $^3J_{H,H}$ 5.6 Hz, CH$_2$NHBoc); 2.67 (t, 2 H, CH$_2$CH$_2$N$_3$); 2.59 (t, 4 H, CH$_2$CH$_2$NHBoc); 1.43 (s, 18 H, CMe$_3$);

$^{13}$C NMR (125.7 MHz; CDCl$_3$): δ 156.0 (CO); 79.1 (CMe$_3$); 53.9 (CH$_2$CH$_2$NHBoc); 53.5 (CH$_2$CH$_2$N$_3$); 49.6 (CH$_2$N$_3$); 38.5 (CH$_2$NHBoc); 28.3 (CMe$_3$).

d) Preparation of bis(2-aminoethyl)-2-azidoethylamine.

This compound is obtained by hydrolysis of the two carbamate groups in 2-azidoethyl-bis(2-tert-butoxycarbonylaminoethyl)amine (0.16 g; 0.43 mmol) by treatment with trifluoroacetic acid-water 1:1 (3 ml) at 40° C. for 2 hours. The evaporation of the solvents under reduced pressure, the co-evaporation of the traces of acid with water and the lyophilization of the resulting residue leads to a white hygroscopic solid (quantitative yield after NMR) having the following characteristics:

mass spectrum (CI$^+$): m/z 173 [M+H]$^+$ $^1$H NMR (500 MHz, D$_2$O): δ 3.63 (t, 2 H, $^3J_{H,H}$ 6.0 Hz, CH$_2$N$_3$); 3.24 (t, 4 H, $^3J_{H,H}$ 6.6 Hz, CH$_2$NH$_2$); 3.08 (t, 4 H, CH$_2$CH$_2$NH$_2$); 2.99 (t, 2 H, CH$_2$CH$_2$N$_3$)

$^{13}$C NMR (75.5 MHz; D$_2$O): δ 52.7 (CH$_2$N$_3$); 50.3 (CH$_2$NH$_2$); 45.7 (CH$_2$CH$_2$N$_3$); 34.1 (CH$_2$CH$_2$NH$_2$).

This compound is used directly in the following stage without additional purification.

e) Preparation of 2-azidoethyl bis[2-[N'-(2,3,4,6-tetra-O-acetyl-α-D-mannopyranosyl)thioureido]ethyl]amine.

This compound is obtained by coupling reaction between bis(2-aminoethyl) 2-azidoethylamine (132 mg; 0.77 mmol) and 2,3,4,6-tetra-O-acetyl-α-D-manropyranosyl isothiocyanate (0.66 g; 1.1 equiv; 1.7 mmol) in water-acetone 4:7 (11 ml) at pH 8-9 (solid sodium acid carbonate) at ambient temperature for 16 hours. Acetone is eliminated at reduced pressure and the aqueous suspension is extracted with dichloromethane (2×5 ml), the organic phase is dried, concentrated and the residue is purified by silica gel column chromatography with ethyl acetate-petroleum ether 2:1. 0.68 g (yield 93%) of a white solid having the following characteristics is thus obtained:

[α]$_D$+52.0° (c 1.0; dichloromethane)

mass spectrum (FAB+): m/z 973 [M+Na]

$^1$H NMR (500 MHz, CDCl$_3$, 313 K): 8 7.83; 7.26 (2 bs, 4 H, NH); 5.66 (bs, 2 H, H-1); 5.49 (dd, 2 H, J$_{2,3}$ 2.2 Hz, J$_{3,4}$ 9.4 Hz, H-3); 5.31 (bd, 2 H, H-2); 5.26 (t, 2 H, J$_{4,5}$ 9.4 Hz, H-4); 4.26 (dd, 2 H, J$_{5,6a}$ 4.8 Hz, J$_{6a,6b}$ 12.4 Hz, H-6a); 4.10 (dd, 2 H, J$_{5,6b}$ 2.4 Hz, H-6b); 3.95 (ddd, 2 H, H-5); 3.74; 3.67 (2 bs, 4 H, CH$_2$NH); 3.34 (t, 2 H, $^3J_{H,H}$ 5.6 Hz, CH$_2$N$_3$); 2.75 (m, 6 H, CH$_2$N); 2.12; 2.05; 2.01; 1.97 (4 s, 6 H, 8 MeCO);

$^{13}$C NMR (125.7 MHz; CDCl$_3$; 313 K): δ 183.3 (CS); 170.5; 169.7; 169.6 (CO); 80.1 (C-1); 69.6 (C-5); 69.1 (C-3); 68.9 (C-2); 66.2 (C-4); 62.1 (C-6); 53.8 (CH$_2$CH$_2$NH); 52.9 (CH$_2$CH$_2$N$_3$); 49.5 (CH$_2$N$_3$); 43.4 (CH$_2$NH); 20.6; 20.4 (MeCO).

f) Preparation of 2-isothiocyanatoethyl bis[2-[N'-(2,3,4,6-tetra-O-acetyl-α-D-mannopyranosyl)thioureido]ethyl] amine.

Triphenylphosphine (0.22 g; 1.2 equiv; 0.85 mmol) and dicarbon disulphide (0.5 ml; 10 equiv; 7.1 mmol) is added to a solution of 2-azidoethyl-bis[2-(N'-(2,3,4,6-tetra-O-acetyl-α-D-mannopyranosyl)thioureido)ethyl]amine (0.68 g; 0.71 mmol) in dioxane (10 ml), and the reaction mixture is stirred at ambient temperature under argon for 24 hours. The solvent is eliminated at reduced pressure and the residue is purified by silica gel column chromatography with ethyl acetate-petroleum ether 3:1. 0.49 g (yield 71%) of a white solid having the following characteristics is thus obtained:

$[\alpha]_D$ +29.0° (c 1.0, dichloromethane)

mass spectrum (FAB$^+$): m/z 989 [M+Na]$^+$ $^1$H NMR (300 MHz, CDCl$_3$, 313 K): δ 7.81; 7.26 (2 bs, 4 H, NH); 5.68 (bs, 2 H, H-1); 5.51 (dd, 2 H, $J_{2,3}$ 3.3 Hz, $J_{3,4}$ 9.5 Hz, H-3); 5.36 (dd, 2 H, $J_{1,2}$ 2.1 Hz H-2); 5.27 (t, 2 H, $J_{4,5}$ 9.5 Hz, H-4); 4.27 (dd, 2 H, $J_{5,6a}$ 4.7 Hz, $J_{6a,6b}$ 12.3 Hz, H-6a); 4.11 (dd, 2 H, $J_{5,6b}$ 2.7 Hz, H-6b); 4.03 (ddd, 2 H, H-5); 3.76 (m, 4 H, CH$_2$NH); 3.61 (t, 2 H, $^3J_{H,H}$ 5.4 Hz, CH$_2$NCS); 2.73 (m, 6 H, CH$_2$N); 2.13; 2.07; 2.02; 1.99 (4 s, each 6 H, 8 MeCO);

$^{13}$C NMR (125.7 MHz, CDCl$_3$, 313 K): δ 183.4 (CS); 170.4; 170.1; 169.5; 169.4 (CO); 132.0 (NCS); 80.3 (C-1); 69.4 (C-5); 69.0 (C-3); 68.8 (C-2); 66.2 (C-4); 62.1 (C-6); 53.3 (CH$_2$CH$_2$NH); 52.6 (CH$_2$CH$_2$NCS); 42.9 (CH$_2$NH, CH$_2$NCS); 20.6; 20.3 (MeCO).

g) Preparation of compound no. 7.

This compound is obtained by coupling reaction between compound no. 2 (58 mg, 23 μmol) and 2-isothiocyanatoethyl bis[2-[N'-(2,3,4,6-tetra-O-acetyl-α-D-mannopyranosyl) thioureido]ethyl]amine (25 mg, 26 μmol) in water-acetone 1:1 (2 ml) at ambient temperature for 4 days, followed by deacetylation as described above for compound no. 5. The resulting residue is purified by gel filtration chromatography (Sephadex G-25, water). Compound no. 7 (36 mg, yield 50%) is thus obtained in the form of a white solid having the following characteristics:

$[\alpha]_D$ +99.6° (c 2.4; H$_2$O)

solubility in water: 375 g·L$^{-1}$ (120 mmol·L$^{-1}$)

mass spectrum (MALDITOF$^+$): m/z 3151 (100%, [M+Na]$^+$)

$^{13}$C NMR (125.7 MHz D$_2$O, 343 K): δ 181.8 (CS); 102.3-101.0 (C-1$^{I\text{-}VII}$); 83.9 (C4$^I$); 82.2-81.3 (C-4$^{II\text{-}VII}$); 78.1 (C-1'); 74.0-73.6 (C-3$^{I\text{-}VII}$); 72.8-72.1 (C-2$^{I\text{-}VII}$, C-5$^{II\text{-}VII}$); 71.2; 70.9; 70.5 (C-5$^I$, C-5', C-3', C-2'); 67.4 (C-4'); 61.7 (C-6'); 61.2-61.0 (C-6$^{II\text{-}VII}$); 53.2, 52.6 (CH$_2$N); 45.7 (C-6$^I$); 42.3 (CH$_2$NHCS).

EXAMPLE 8

Preparation of the bis[2-[N'-(6$^I$-deoxycyclomalto-heptaos-6$^I$-yl)thioureido]ethyl] 2-[N'-[2-[bis[2-[N'-[tris(α-D-mannopyranosyloxymethyl) methyl]thio-ureido]ethyl] amino]ethyl]thioureido]ethylamine (compound no. 8)

This compound corresponds to formula (I) given above with A=H, n=n'=2, m=6, in which X represents a sulphur atom, Y represents NH, W represents a nitrogen atom and Z represents the (CH$_2$)$_2$NHC(=S)NH(CH$_2$)$_2$N[(CH$_2$2NHC(=S)NHR]$_2$ group, R corresponding to formula (IV) given above (see also formula (H-c) with m=6). This compound therefore corresponds to the following formula:

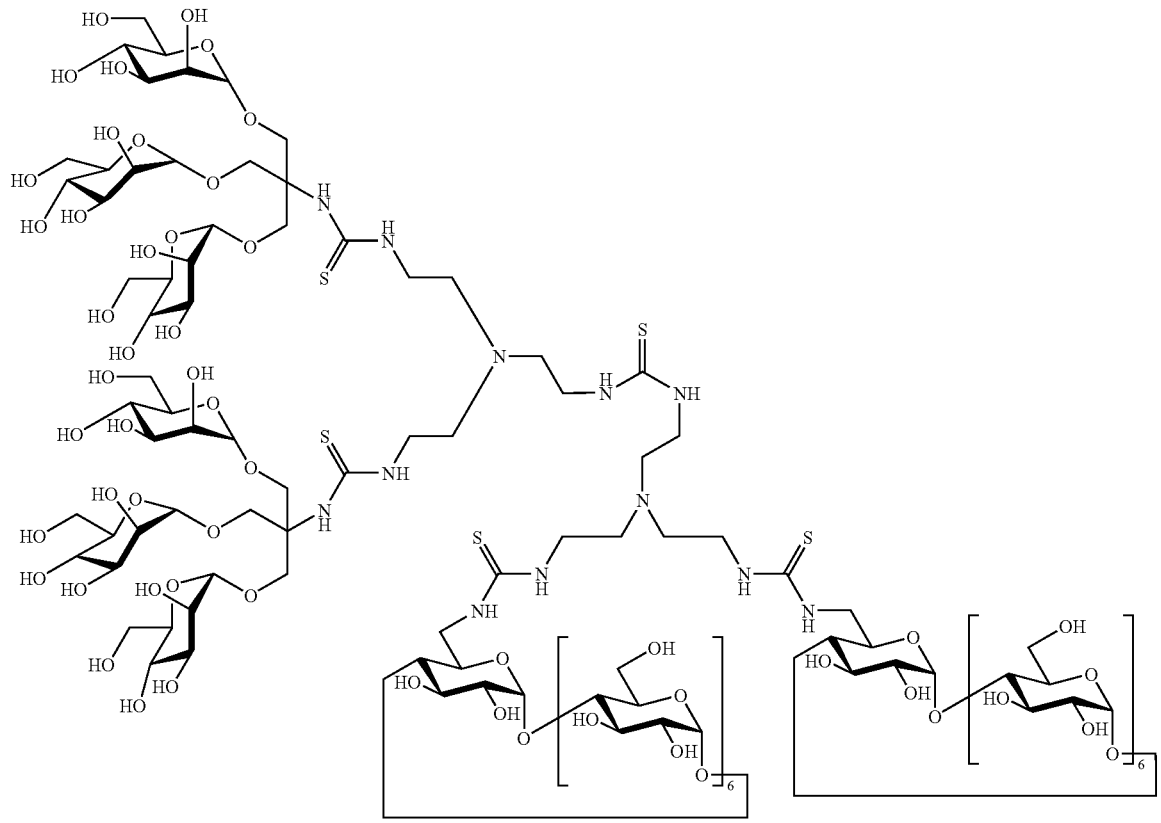

This compound is obtained by carrying out the following stages:

a) Preparation of 2-azidoethyl bis[2-[N'-[tris(2,3,4,6-tetra-O-acetyl-α-D-mannopyranosyloxymethyl)methyl]thioureido]ethyl]amine.

This compound is obtained by coupling between bis(2-aminoethyl)-2-azidoethylamine (45 mg; 0.26 mmol), obtained as indicated above, and tris(2,3,4,6-tetra-O-acetyl-α-D-mannopyranosyloxymethyl)methyl isothiocyanate (0.6 g; 0.52 mmol) in water-acetone 1:5 (6 ml) at ambient temperature for 24 hours. Acetone is eliminated at reduced pressure and the aqueous suspension is extracted with dichloromethane (2×5 ml), the organic phase is dried, concentrated and the residue is purified by silica gel column chromatography with dichloromethane-methanol 30:1. 0.51 g (yield 79%) of a white solid having the following characteristics is thus obtained:

$[\alpha]_D$+47.20 (c 1.0; $CH_2Cl_2$);

mass spectrum ($FAB^+$): m/z 2503 [M+Na]$^+$ $^1$H NMR (500 MHz, $CDCl_3$, 313 K): δ 6.87; 6.13 (2 bs, 4 H, NH); 5.27 (t, 6 H, $J_{3,4}=J_{4,5}$ 9.6 Hz, H-4); 5.18 (dd, 6 H, $J_{2,3}$ 3.3 Hz, H-3); 5.18 (bs, 6 H, H-2); 4.88 (bs, 6 H, H-1); 4.31 (dd, 6 H, $J_{5,6a}$ 4.7 Hz, $J_{6a,6b}$ 12.4 Hz, H-6a); 4.28 (d, 6 H, $^2J_{H,H}$ 10.0 Hz, $OCH_2$a); 4.10 (dd, 6 H, $J_{5,6b}$ 2.3 Hz, H-6b); 4.03 (d, 6 H, $OCH_2$b); 4.00 (ddd, 6 H, H-5); 3.52 (m, 4 H, $CH_2NH$); 3.36 (m, 2 H, $CH_2N_3$); 2.77 (m, 6H, $CH_2N$); 2.11; 2.08; 2.00; 1.94 (4 s, each 18 H, 24 MeCO);

$^{13}$C NMR (125.7 MHz; $CDCl_3$; 313 K): δ 182.1 (CS); 170.6; 169.8; 169.6; 169.4 (CO); 98.3 (C-1); 69.1; 68.9 (C-2, C-3, C-5); 66.5 ($OCH_2$); 65.8 (C-4); 62.1 (C-6); 60.8 ($C_q$); 52.2 ($CH_2N$); 49.2 ($CH_2N_3$); 41.6 ($CH_2NH$); 20.6; 20.5; 20.4 (MeCO).

b) Preparation of 2-isothiocyanatoethyl-bis[2-[N'-[tris(2,3,4,6-tetra-O-acetyl-α-D-mannopyranosyloxymethyl)methyl]thioureido]ethyl]amine.

Triphenylphosphine (59 mg; 1.1 equiv; 0.22 mmol) and dicarbon disulphide (0.13 ml; 10 equiv; 2.0 mmol) is added to a solution of 2-azidoethyl-bis[2-[N'-[tris(2,3,4,6-tetra-O-acetyl-α-D-mannopyranosyloxymethyl)methyl]thioureido]ethyl]amine (0.51 g; 0.20 mmol) in dioxane (5 ml), and the reaction mixture is stirred at ambient temperature under argon for 24 hours. The solvent is eliminated under reduced pressure and the residue is purified by silica gel column chromatography with the eluent dichloromethane-methanol 50:1. 0.36 g (yield 73%) of a white solid having the following characteristics is thus obtained:

$[\alpha]_D$+45.9° (c 1.0; $CH_2Cl_2$)

mass spectrum ($FAB^+$): m/z 2519 [M+Na]$^+$ $^1$H NMR (500 MHz, $CDCl_3$, 313 K): δ 6.88; 6.18 (2bs, 4 H, NH); 5.27 (t, 6 H, $J_{3,4}=J_{4,5}$ 9.8 Hz, H-4); 5.21 (dd, 6 H, $J_{2,3}$ 3.2 Hz, H-3); 5.19 (bs, 6 H, H-2); 4.89 (bs, 6 H, H-1); 4.31 (dd, 6 H, $J_{5,6a}$ 5.1 Hz, $J_{6a,6b}$ 12.4 Hz, H-6a); 4.30 (d, 6 H, $^2J_{H,H}$ 10.0 Hz, $OCH_2$a); 4.11 (dd, 6 H, $J_{5,6b}$ 2.0 Hz, H-6b); 4.09 (d, 6 H, $OCH_2$b); 4.01 (ddd, 6 H, H-5); 3.61 (m, 6 H, $CH_2NH$, $CH_2NCS$); 2.77 (m, 6 H, $CH_2N$); 2.11; 2.08; 2.01; 1.96 (4 s, each 18 H, 24 MeCO);

$^{13}$C NMR (125.7 MHz; $CDCl_3$; 313 K): δ 182.1 (CS); 170.6; 169.8; 169.6; 169.4 (CO); 133.0 (NCS); 98.3 (C-1); 69.2; 69.1; 68.9 (C-2, C-3, C-5); 66.4 ($OCH_2$); 65.5 (C-4); 61.9 (C-6); 60.9 ($C_q$); 51.6 ($CH_2N$); 45.8 ($CH_2NCS$); 41.3 ($CH_2NH$); 20.7; 20.6; 20.5 (MeCO).

c) Preparation of Compound No. 8.

This compound is obtained by coupling reaction between compound no. 2 (58 mg, 23 µmol) and 2-isothiocyanatoethyl-bis[2-[N'-[tris(2,3,4,6-tetra-O-acetyl-α-D-mannopyranosyloxymethyl)methyl]thioureido]ethyl]amine (65 mg, 26 µmol) in water-acetone 1:1 (2 ml) at ambient temperature for 4 days, followed by deacetylation as described above for compound no. 6. The resulting residue is purified by gel filtration chromatography (Sephadex G-25, water). Compound no. 8 (49 mg, yield 51%) is thus obtained in the form of a white solid having the following characteristics:

$[\alpha]_D$+62.0° (c 1.0; $H_2O$)

solubility in water: 400 g·L$^{-1}$ (100 mmol·L$^{-1}$)

mass spectrum (MALDITOF$^+$): m/z 4008 (100%, [M+Na]$^+$)

$^1$H NMR (500 MHz, $D_2O$, 333 K): δ 5.34 (m, 14 H, H-1$^{I-VII}$); 5.15 (m, 18 H, H-2', H-3', H-4'); 5.09 (bs, 6 H, H-1'); 4.37 (d, 6 H, $^2J_{H,H}$ 10.5 Hz, $OCH_2$a); 4.31-4.10 (m, 72 H, H-3$^{I-VII}$, H-5$^{I-VII}$, H-6a$^{I-VII}$, H-6b$^{II-VII}$, $CH_2N$, $OCH_2$b); 4.09-4.04 (m, 14 H, H-2$^{I-VII}$); 4,03-3.88 (m, 24 H, H-4$^{II-VII}$, $CH_2NH$); 3.67 (m, 4 H, H-4$^I$, H-6b$^I$);

$^{13}$C NMR (125.7 MHz; $D_2O$; 333 K): δ 181.5 (CS); 102.2 (C-1$^{I-VII}$); 100.8 (C-1'); 81.4 (C-4$^{I-VII}$); 74.2-73.9-72.3 (C-2$^{I-VII}$, C-3$^{I-VII}$, C-5$^{I-VII}$); 71.3; 70.5 (C-3', C-2', C-5'); 67.3 (C-4',$OCH_2$); 61.6 (C-6'); 60.8 (C-6$^{II-VII}$); 52.8 ($CH_2N$); 42.6 (C-6$^I$); 37.6 ($CH_2NHCS$).

EXAMPLE 9

Evaluation of the Affinity of Thioureidocysteaminyl-cyclodextrins Compounds No. 5 to 8 for the Mannose-specific Lectin Concanavalin A (ConA)

The affinity of compounds no. 5 to 8 for the mannose-specific lectin concanavalin A (ConA) was evaluated according to the test ELLA protocol. The concentration of compounds no. 5 to 8 necessary to inhibit the combination of ConA with a reference ligand (yeast mannan in this case) fixed to a microtitration plate cell ($IC_{50}$) to 50% is thus obtained. The $IC_{50}$ values are inversely proportional to the respective affinities.

The microtitration plate cells (Nunc-Immuno™ plates MaxiSorp™) are charged with 100 µl of a yeast mannan stock solution (Sigma, 10 µg/l$^{-1}$) in a saline phosphate buffer solution (PBS; pH 7.3 containing $Ca^{2+}$ 0.1 mM and $Mn^{2+}$ 0.1 mM) overnight at ambient temperature. The cells are washed (3×300 µl) with a buffer solution containing 0.05% (v/v) Tween 20 (PBTS). This washing protocol is repeated after each incubation during the test. A bovine serum albumin solution (BSA, 1%) in PBS (150 µg/cell) is then added to the cells, followed by incubation for 1 h at 37° C. and then washing.

To determine the optimum lectin concentration for the inhibition studies, 100 µl of a series of Con A solutions labelled with 10$^{-1}$ to 10$^{-5}$ mg.ml$^{-1}$ horse-radish peroxidase in PBS is added to the cells charged with the mannan, followed by treating as indicated above. After incubation at 37° C. for 1 hour, the plates are washed (PBST) and a solution (50 µl) of the diammonium salt of 2,2'-azinobis(3-ethylbenzothiazoline-6-sulphonic) acid (ABTS, 1 mg in 4 ml) in citrate buffer is added (0.2 M; pH 4.0 with 0.015% of oxygenated water). The reaction is stopped after 20 minutes by adding 50 µl/cell sulphuric acid 1 M and the absorbances are measured at 415 nm using an ELISA reader. The sample cells contain the citrate-phosphate buffer. The concentration of lectin marked with peroxidase giving an absorbance value between 0.8 and 1.0 (typically between 10$^{-2}$ and 10$^{-3}$ mg/ml$^{-1}$) was used in the inhibition assays.

For inhibition assays, stock solutions of compounds no. 5 to 8 were used at a concentration of 5 to 7 mg/ml$^{-1}$ in PBS. In a series of experiments, ConA marked with horse-radish peroxidase of suitable concentration as indicated above (60 µl/cell) is added to the solutions of each compound (60 µl/cell) in PBS, double-diluted in sequence, in a Nunclon™ (Delta) microtitration plate which is incubated at 37° C. for 1 hour. The solutions (100 µl/cell) are then transferred to a microtitration plate charged with mannan and treated as indicated above, then being incubated at 37° C. for 1 hour. The cells are washed (PBST) and ABTS solution added (50 µl/cell). After 20 minutes, the reaction is stopped (sulphuric acid) and the absorbances are measured.

The inhibition percentage is calculated by the formula:

$$\% \text{ inhibition} = \frac{A_{in\ the\ absence\ of\ inhibitor}}{A_{in\ the\ presence\ of\ inhibitor}} \times 100$$

Table 1 below gives the $IC_{50}$ values for compounds no. 5 to 8 (average of three independent experiments) compared with the corresponding value for methyl-α-D-glucopyranoside, used as monovalent reference ligand. A significant increase in the affinity for lectin is observed in the case of the trivalent derivative and the hexavalent derivative comprising mannopyranosyl substituents. Thus compound no. 8 with a hexavalent dendritic presentation of the mannopyranosyl ligand is recognized up to 25 times more effectively by the mannose-specific lectin ConA compared with the monovalent cyclodextrin dimer derivative, compound no. 5.

TABLE 1

ELLA data for the inhibition of the combination of yeast mannan and ConA lectin labelled with horse-radish peroxidase by compounds no. 5 to 8.

| | Compound | | | |
|---|---|---|---|---|
| | Me-α-D-Glcp | no. 5 | no. 6 | no. 7 | no. 8 |
| $IC_{50}$ (µM) | 865 | 1288 | 1130 | 265 | 49 |
| Relative affinity | 1 | 0.67 | 0.76 | 3.3 | 17.7 |
| Relative molar affinity | 1 | 0.67 | 0.38 | 1.1 | 2.9 |

EXAMPLE 10

Inclusion of Taxotere® into bis[2-[N'-(6$^I$-deoxycyclomaltoheptaos-6$^I$-yl)thioureido]ethyl] 2-(N'-methylthioureido)ethyl amine (compound no. 3)

Taxotere in the pure state is used to start with and 8.3 mg (9.7 µmol) of this product is dispersed in 1 ml of a solution containing 10 mmol.l$^{-1}$ of compound no. 3 in sterile water, then the obtained suspension is stirred at 70° C. until a clear solution is obtained which signals the complexation of the Taxotere. Once formed, the complex remains in solution at ambient temperature. An increase in the solubility of the Taxotere (8.3 g·l$^{-1}$) of the order of 2075 times relative to that of Taxotere in the absence of cyclodextrin (0.004 g·L$^{-1}$) is thus obtained.

EXAMPLE 11

Inclusion of Taxotere® into bis[2-[N'-(6$^I$-deoxycyclomaltoheptaos-6$^I$-yl)thioureido]ethyl] 2-[N'-[tris(2,3,4,6-tetra-O-acetyl-α-D-mannopyranosyloxymethyl)methyl]thioureido]ethylamine (compound no. 6).

Taxotere in the pure state is used to start with and 6.6 mg (7.7 µmol) of this product is dispersed in 1 ml of a solution containing 8 mmol/l$^{-1}$ of compound no. 6 in sterile water, then the obtained suspension is stirred at 70° C. until a clear solution is obtained which signals the complexation of the Taxotere. Once formed, the complex remains in solution at ambient temperature. An increase in the solubility of the Taxotere (6.6 g·L$^{-1}$) of the order of 1650 times relative to that of Taxotere in the absence of cyclodextrin (0.004 g·L$^{-1}$) is thus obtained.

EXAMPLE 12

Bis[2-[N'-(6$^I$-deoxycyclomaltoheptaos-6$^I$-yl)thioureido]ethyl] 2-[N'-[2-[bis[2-[N'-[tris(α-D-mannopyranosyloxymethyl)methyl]thioureido]ethyl] amino] ethyl]thioureido]ethyl amine (compound no. 8)

Taxotere in the pure state is used to start with and 5.8 mg (68 µmol) of this product is dispersed in 1 ml of a solution containing 7 mmol/l$^{-1}$ of compound no. 6 in sterile water, then the obtained suspension is stirred at 70° C. until a clear solution is obtained which signals the complexation of the Taxotere. Once formed, the complex remains in solution at ambient temperature. An increase in the solubility of the Taxotere (5.8 g·l$^{-1}$) of the order of 1450 times relative to that of Taxotere in the absence of cyclodextrin (0.004 g/l$^{-1}$) is thus obtained.

The invention claimed is:

1. An inclusion complex of a compound according to formula I with a pharmacologically active molecule, the molar ratio between the compound and the pharmacologically active molecule being approximately 10:1 to approximately 1:2, and said formula I being:

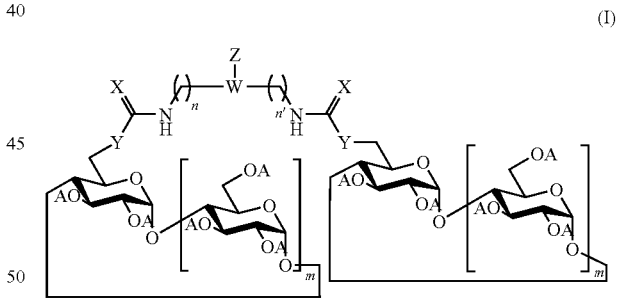

(I)

wherein, m represents an integer equal to 5, 6 or 7;

n and n' represent an integer from 1 to 5, n and n' being identical or different;

A represents a hydrogen atom, an acyl, an alkyl, a hydroxyalkyl or a sulphoalkyl group of 1 to 16 carbon atoms, each A being identical or different;

X represents O or S,

Y represents a group selected from the group consisting of:

(i) an —NR$_1$— group, wherein R$_1$ represents a hydrogen atom or an alkyl group comprising from 1 to 6 carbon atoms, such that said compound corresponds to formula (I-a):

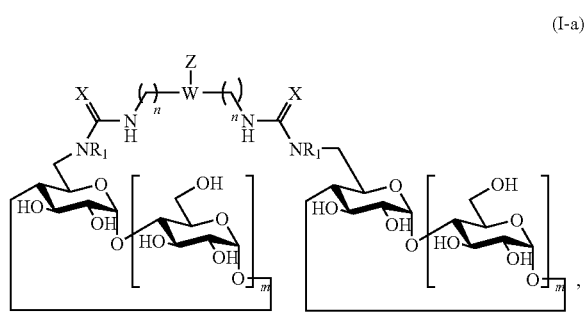

(I-a)

(ii) an amide group of formula —NH—CO—(CH$_2$)$_q$—NR$_1$—, wherein q represents an integer from 1 to 5 and R$_1$ represents a hydrogen atom or an alkyl group comprising from 1 to 6 carbon atoms, such that said compound corresponds to formula (I-b):

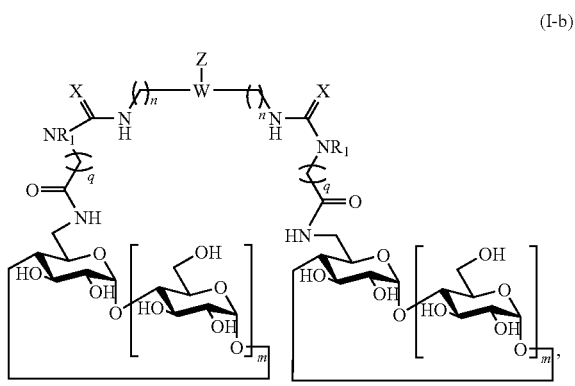

(I-b)

and (iii) a cysteaminyl group of formula —S—(CH$_2$)$_r$—NR$_1$—, wherein r represents an integer from 2 to 5 and R$_1$ represents a hydrogen atom or an alkyl group comprising from 1 to 6 carbon atoms, so that said compound corresponds to formula (I-c):

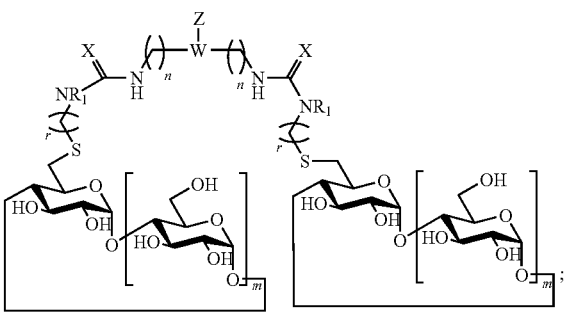

(I-c)

W represents CH or N; and

Z represents a group selected from the group consisting of:

a carbamate substituent of formula

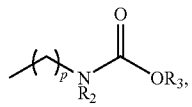

an amine substituent of formula

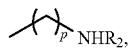

a quaternary ammonium group of formula

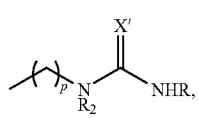

a urea or thiourea substituent of formula:

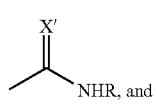

a group of formula one of a group according to formula C(=O)OR$_3$, a group according to formula C(=O)R$_2$, and a group carrying the amine, ammonium quaternary urea or thiourea functionalities, of respective formulae:

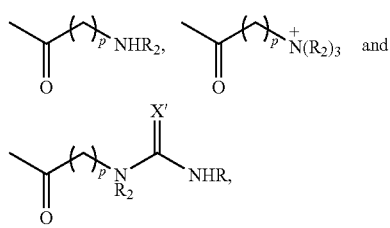

p representing an integer from 0 to 5, when W represents CH, and from 2 to 5, when W represents N, X' representing O or S, R$_2$ representing a hydrogen atom or an alkyl group comprising from 1 to 6 carbon atoms, R$_3$ representing a substituent allowing the hydrolysis of the carbamate group in order to release the amine function, and R representing one of:

(i) a substituent selected from the group consisting of a hydrogen atom, a linear or branched alkyl group of 1 to 12 carbon atom, an aromatic group, and an aromatic group carrying at least one substituent on the aromatic ring, said at least one substituent selected from the group consisting of methyl, ethyl, chlorine, bromine, iodine, nitro, hydroxyl, methoxyl and acetamido substituents, and (ii) a biological recognition element selected from the group consisting of an amino acid, a peptide, a monosaccharide, an oligosaccharide, and a multiplication element with sevaral branchings, said branchings selected from the group consisting of:
  (a) glucide groups, which can be identical or different, and
  (b) molecular structure allowing detection by fluorescent or radioactive visualization.

2. The inclusion complex according to claim 1 wherein the pharmacologically active molecule is a ditopic molecule.

3. The inclusion complex according to claim 1, wherein the pharmacologically active molecule is an antineoplastic agent.

4. A pharmaceutical composition comprising the inclusion complex according to claim 1, in association with a pharmacologically acceptable vehicle.

5. A pharmaceutical composition comprising the inclusion complex according to claim 1, in association with a pharmacologically acceptable vehicle, in the form of aqueous solution.

6. A pharmaceutical composition comprising the inclusion complex according to claim 1, in association with a pharmacologically acceptable vehicle, wherein said complex is approximately 100 mg to approximately 750 mg per unit dose of said pharmaceutical composition.

\* \* \* \* \*